US012760112B2

(12) United States Patent
Altarejos et al.

(10) Patent No.: US 12,760,112 B2
(45) Date of Patent: Oct. 13, 2026

(54) COMPOSITIONS AND METHODS FOR ENHANCING BODY WEIGHT AND LEAN MUSCLE MASS USING ANTAGONISTS AGAINST LEPTIN RECEPTOR, GDF8 AND ACTIVIN A

(71) Applicant: Regeneron Pharmaceuticals, Inc., Tarrytown, NY (US)

(72) Inventors: Judith Altarejos, Armonk, NY (US); Jesper Gromada, Concord, MA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 804 days.

(21) Appl. No.: 17/415,589

(22) PCT Filed: Dec. 17, 2019

(86) PCT No.: PCT/US2019/066908
§ 371 (c)(1),
(2) Date: Jun. 17, 2021

(87) PCT Pub. No.: WO2020/131910
PCT Pub. Date: Jun. 25, 2020

(65) Prior Publication Data

US 2022/0220213 A1 Jul. 14, 2022
US 2024/0247071 A2 Jul. 25, 2024

Related U.S. Application Data

(60) Provisional application No. 62/781,226, filed on Dec. 18, 2018.

(51) Int. Cl.

| | |
|---|---|
| ***C07K 16/28*** | (2006.01) |
| ***A61K 33/26*** | (2006.01) |
| ***A61K 39/395*** | (2006.01) |
| ***A61K 45/06*** | (2006.01) |
| ***A61P 21/00*** | (2006.01) |
| ***C07K 16/22*** | (2006.01) |

(52) U.S. Cl.
CPC .......... *C07K 16/2869* (2013.01); *A61K 33/26* (2013.01); *A61K 39/3955* (2013.01); *A61K 45/06* (2013.01); *A61P 21/00* (2018.01); *C07K 16/22* (2013.01); *C07K 2317/56* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,596,556 | A | 6/1986 | Morrow et al. |
| 4,790,824 | A | 12/1988 | Morrow et al. |
| 4,941,880 | A | 7/1990 | Burns |
| 4,946,778 | A | 8/1990 | Ladner et al. |
| 5,064,413 | A | 11/1991 | McKinnon et al. |
| 5,312,335 | A | 5/1994 | McKinnon et al. |
| 5,383,851 | A | 1/1995 | McKinnon, Jr. et al. |
| 5,399,163 | A | 3/1995 | Peterson et al. |
| 5,717,073 | A | 2/1998 | Wijdenes et al. |
| 5,932,448 | A | 8/1999 | Tso et al. |
| 5,965,521 | A | 10/1999 | Stephens et al. |
| 6,005,080 | A | 12/1999 | Snodgrass et al. |
| 6,096,002 | A | 8/2000 | Landau |
| 6,096,506 | A | 8/2000 | Lee et al. |
| 6,129,914 | A | 10/2000 | Weiner et al. |
| 6,329,511 | B1 | 12/2001 | Vasquez et al. |
| 6,380,363 | B1 | 4/2002 | Tartaglia et al. |
| 6,620,135 | B1 | 9/2003 | Weston et al. |
| 6,977,240 | B1 | 12/2005 | Tartaglia et al. |
| 7,067,472 | B1 | 6/2006 | Feng et al. |
| 7,067,477 | B2 | 6/2006 | Macleod |
| 7,183,254 | B2 | 2/2007 | Depaoli et al. |
| 7,261,893 | B2 | 8/2007 | Veldman et al. |
| 7,294,754 | B2 | 11/2007 | Poueymirou et al. |
| 7,307,142 | B2 | 12/2007 | Gertler et al. |
| 7,320,789 | B2 | 1/2008 | Aghajanian et al. |
| 7,521,048 | B2 | 4/2009 | Gliniak et al. |
| 7,524,937 | B2 | 4/2009 | Carter et al. |
| 7,575,878 | B2 | 8/2009 | Tavernier et al. |
| 7,576,259 | B2 | 8/2009 | Poueymirou et al. |
| 7,632,499 | B2 | 12/2009 | Davies et al. |

(Continued)

FOREIGN PATENT DOCUMENTS

| | | | |
|---|---|---|---|
| AU | 2004201496 | C1 | 8/2018 |
| CN | 107760761 | | 3/2018 |

(Continued)

OTHER PUBLICATIONS

Anthony (2008) "Nutrition Screening Tools for Hospitalized Patients" Nutr Clin Pract 23:373-382.
Baca et al. (1997) "Antibody Humanization Using Monovalent Phage Display" J Biol Chem 272(16):10678-10684.
Barbas (1995) "Synthetic Human Antibodies" Nat Med 1(8):837-839.
Brennan et al. (1985) "Preparation of Bispecific Antibodies by Chemical Recombination of Monoclonal Immunoglobulin G1 Fragments" Science 229:81-83.

(Continued)

*Primary Examiner* — Nelson B Moseley, II
*Assistant Examiner* — James Ryland Melchior
(74) *Attorney, Agent, or Firm* — FisherBroyles, LLP; Christy G. Rothwell; Gabriele Amodeo

(57) ABSTRACT

The present invention provides combinations including antagonists of leptin receptor, GDF8 and Activin A and methods of use thereof. Such compositions are effective for example for causing an increase in lean body mass, at least in part, at the expense of fat mass. Methods for treating malnutrition, cachexia and other conditions characterized by insufficient nutrition and weight loss are also provided.

4 Claims, No Drawings

Specification includes a Sequence Listing.

(56) References Cited

U.S. PATENT DOCUMENTS 7,635,760 B2 12/2009 Han et al.
7,659,442 B2 2/2010 Poueymirou et al.
7,807,159 B2 10/2010 Chin et al.
7,863,240 B2 1/2011 Ilan et al.
7,888,486 B2 2/2011 Walsh et al.
8,017,634 B2 9/2011 Sinclair et al.
8,318,666 B2 11/2012 DePaoli et al.
8,697,396 B2 4/2014 Dall'Acqua et al.
8,840,894 B2 * 9/2014 Stitt ........................ A61P 21/04 424/142.1
8,846,724 B2 9/2014 Sinclair et al.
8,871,209 B2 * 10/2014 Stitt ........................ A61P 21/06 530/388.23
8,969,291 B2 3/2015 Ilan et al.
9,221,902 B2 12/2015 Smider et al.
9,260,515 B2 * 2/2016 Stitt ........................ A61P 19/00
9,332,742 B2 5/2016 Mcwhirter et al.
9,334,331 B2 5/2016 Igawa et al.
9,421,257 B2 8/2016 Ilan et al.
9,718,881 B2 * 8/2017 Gromada .................. A61P 3/04
9,890,212 B2 * 2/2018 Stitt .......................... A61P 7/00
10,023,644 B2 7/2018 Gromada et al.
10,253,102 B2 4/2019 Gromada et al.
10,400,036 B2 * 9/2019 Stitt ........................ A61P 21/06
10,421,807 B2 9/2019 Gonzales et al.
10,526,403 B2 * 1/2020 Gromada ................ A61P 25/00
10,550,192 B2 * 2/2020 Gromada .................. A61P 3/00
10,618,968 B2 4/2020 Gromada et al.
10,934,349 B2 * 3/2021 Pordy ..................... A61P 29/00
11,248,044 B2 * 2/2022 Donahue ................... A61P 3/04
11,535,675 B2 * 12/2022 Gromada ........... A61K 39/3955
11,608,381 B2 3/2023 Gromada et al.
11,834,500 B2 12/2023 Gromada et al.
12,275,792 B2 4/2025 Gromada et al.
12,371,503 B2 7/2025 Gromada et al.
2002/0182676 A1 12/2002 Tartaglia et al.
2004/0202652 A1 10/2004 Karsenty et al.
2004/0253242 A1 12/2004 Bowdish et al.
2006/0068429 A1 3/2006 Bailleul et al.
2007/0178095 A1 8/2007 Smith et al.
2007/0280945 A1 12/2007 Stevens et al.
2008/0078000 A1 3/2008 Poueymirou et al.
2009/0148436 A1 6/2009 LaVallie et al.
2009/0234106 A1 9/2009 Han et al.
2010/0166764 A1 7/2010 Sayers et al.
2010/0260772 A1 10/2010 Karsenty
2011/0029630 A1 2/2011 Tosey
2011/0092417 A1 4/2011 Artymiuk et al.
2012/0204278 A1 8/2012 Bradley et al.
2012/0258073 A1 10/2012 Gerdes et al.
2014/0134162 A1 5/2014 Stavenhagen et al.
2014/0171623 A1 6/2014 Dall'Acqua et al.
2014/0243504 A1 8/2014 Davis et al.
2017/0101477 A1 4/2017 Gromada et al.
2018/0037648 A1 2/2018 Ilan et al.
2019/0002569 A1 1/2019 Belaid-Choucair et al.
2019/0185562 A1 6/2019 Gromada et al.
2019/0309079 A1 10/2019 Gromada et al.
2020/0031946 A1 1/2020 Gromada et al.
2020/0123264 A1 4/2020 Gromada et al.
2022/0098313 A1 3/2022 Oral et al.
2022/0112293 A1 4/2022 Gromada et al.
2022/0280641 A1 9/2022 Gromada et al.
2023/0235068 A1 7/2023 Gromada et al.
2024/0158497 A1 5/2024 Gromada et al.
2024/0247071 A2 7/2024 Altarejos et al.
2025/0051465 A1 2/2025 Gromada et al.

FOREIGN PATENT DOCUMENTS

EP 0981365 B1 12/2004
EP 0885299 B1 10/2005
EP 0730606 B1 11/2005
EP 0879286 B1 4/2008
EP 1619250 B1 11/2009
EP 1444516 B1 7/2010
EP 1019432 B1 1/2012
EP 2219031 B1 4/2013
EP 2780368 9/2014
EP 2649184 B1 7/2015
EP 3298889 B1 3/2018
EP 3538554 9/2019
EP 2989894 B1 8/2020
EP 3362477 B1 1/2022
JP 1991-219894 9/1991
WO WO 1996/005309 2/1996
WO WO 1996/08510 3/1996
WO WO 1997/019952 6/1997
WO WO 1997/025425 7/1997
WO WO 1997/26272 7/1997
WO WO 1997/26335 7/1997
WO WO 1997/26370 7/1997
WO WO 1997/26523 7/1997
WO WO 1997/27286 7/1997
WO WO 1997/41263 11/1997
WO WO 1998/22128 A1 5/1998
WO WO 1998/48831 11/1998
WO WO 2002/36789 8/2002
WO WO 2002/66630 8/2002
WO WO 2005/049655 6/2005
WO WO 2006/053883 5/2006
WO WO 2010/070094 6/2010
WO WO 2011/004192 1/2011
WO WO 2011/097603 8/2011
WO 2011/130499 A1 10/2011
WO WO 2011/150008 A1 12/2011
WO WO 2012/141798 10/2012
WO WO 2012/148873 11/2012
WO WO 2013/022782 2/2013
WO WO 2013/074557 5/2013
WO WO 2013/184761 12/2013
WO WO 2014/043361 A1 3/2014
WO WO 2015/017576 2/2015
WO WO 2015/124588 8/2015
WO 2016/039796 A2 3/2016
WO 2016/168613 A1 10/2016
WO WO 2017/066204 4/2017
WO WO 2018/089532 A1 5/2018
WO WO 2019/195796 10/2019
WO WO 2020/131910 A1 6/2020
WO WO 2022/060827 A3 4/2022

OTHER PUBLICATIONS

Carpenter et al. (2000) "Non-Fc Receptor-Binding Humanized Anti-CD3 Antibodies Induce Apoptosis of Activated Human T Cells" J Immunol 165(11):6205-6213.
Carter (2001) "Bispecific Human IgG by Design" J Immunol Meth 248:7-15.
Chothia et al. (1989) "Conformations of Immunoglobulin Hypervariable Regions" Nature 342:877-883.
Conrath et al. (2001) "Camel Single-Domain Antibodies as Modular Building Units in Bispecific and Bivalent Antibody Constructs" J Biol Chem 276(10):7346-7350.
De Bruin et al. (1999) "Selection of High-Affinity Phage Antibodies from Phage Display Libraries" Nat Biotech 17:397-399.
Dechiara et al. (2009) "VelociMouse: Fully ES Cell-Derived FO-Generation Mice Obtained from the Injection of ES Cells into Eight-Cell-Stage Embryos" Meth Mol Biol 530:311-24.
Dechiara et al. (2010) "Producing Fully ES Cell-Derived Mice from Eight-Cell Stage Embryo Injections" Meth Enzymol 476:285-94.
Desmyter et al. (2001) "Antigen Specificity and High Affinity Binding Provided by One Single Loop of a Camel Single-Domain Antibody" J Biol Chem 276(28):26285-26290.
Detsky et al. (1987) "What is Subjective Global Assessment of Nutritional Status?" J Parent Enteral Nutr 11(1):8-13.
Everts et al. (2002) "Selective Intracellular Delivery of Dexamethasone into Activated Endothelial Cells Using an E-Selection-Directed Immunoconjugate" J Immunol 168:883-889.

(56) References Cited

OTHER PUBLICATIONS

Fearon et al. (2011) "Definition and Classification of Cancer Cachexia: An International Consensus" Lancet Oncol 12:489-495.
Ferguson et al. (1999) "Validation of a Malnutrition Screening Tool for Patients Receiving Radiotherapy" Australas Radio 43:325-327.
Foote and Winter (1992) "Antibody Framework Residues Affecting the Conformation of the Hypervariable Loops" J Mol Biol 224:487-499.
Gibellini et al. (1998) "Extracellular HIV-1 Tat Protein Induces the Rapid Ser133 Phosphorylation and Activation of CREB Transcription Factor in Both Jurkat Lymphoblastoid T Cells and Primary Peripheral Blood Mononuclear Cells" J Immunol 160:3891-3898.
He et al. (1998) "Humanization and Pharmacokinetics of a Monoclonal Antibody with Specificity for Both E- and P-Selectin" J Immunol 160:1029-1035.
Hoogenboom and Chames (2000) "Natural and Designer Binding Sites Made by Phage Display Technology" Immunol Today 21(8):371-377.
Hsing and Bishop (1999) "Requirement for Nuclear Factor-kB Activation by a Distinct Subset of CD40-Mediated Effector Functions in B Lymphocytes" J Immunol 162:2804-2811.
Hudson and Kortt (1999) "High Avidity scFv Multimers; Diabodies and Triabodies" J Immunol Meth 231:177-189.
International Search Report and Written Opinion for PCT/US2019/066908 mailed Mar. 25, 2020.
Kaithamana et al. (1999) "Induction of Experimental Autoimmune Graves' Disease in BALB/c Mice" J Immunol 163:5157-5164.
Kruizenga et al. (2005) "Development and Validation of a Hospital Screening Tool for Malnutrition: The Short Nutritional Assessment Questionnaire (SNAQ)" Clin Nutr 24:75-82.
Kruizenga et al. (2010) "The SNAQRC, an Easy Traffic Light System as a First Step in the Recognition of Undernutrition in Residential Care" J Nutr Health Aging 14(2):83-89.
Latres et al. (2017) "Activin A More Prominently Regulates Muscle Mass in Primates Than Does GDF8" Nat Comm 8:15153.
Le Doussal et al. (1991) "Enhanced In Vivo Targeting of an Asymmetric Bivalent Hapten to Double-Antigen-Positive Mouse B Cells with Monoclonal Antibody Conjugate Cocktails" J Immunol 146(1):169-175.
Mack et al. (1995) "A Small Bispecific Antibody Construct Expressed as a Functional Single-Chain Molecule with High Tumor Cell Cytotoxicity" Proc Natl Acad Sci 92:7021-7025.
Malecki et al. (2002) "Molecular Immunolabeling with Recombinant Single-Chain Variable Fragment (scFv) Antibodies Designed with Metal-Binding Domains" Proc Natl Acad Sci 99(1):213-218.
Mendez et al. (1997) "Functional Transplant of Megabase Human Immunoglobulin Loci Recapitulates Human Antibody Response in Mice" Nat Gen 15:146-156.
Menne et al. (2000) "A Comparison of Signal Sequence Prediction Methods Using a Test Set of Signal Peptides" Bioinformatics 16(8):741-742.
Meyaard et al. (1997) "LAIR-1, a Novel Inhibitory Receptor Expressed on Human Mononuclear Leukocytes" Immunity 7:283-290.
Morrison (1985) "Transfectomas Provide Novel Chimeric Antibodies" Science 229:1202-1207.
Neelemaat et al. (2008) "Screening Malnutrition in Hospital Outpatients. Can the SNAQ Malnutrition Screening Tool Also be Applied to this Population?" Clin Nutr 27:439-446.
Park and Ahima (2014) "Leptin Signaling" F1000Prime Reports 6:73.
R&D Systems "Anti-Activin A Antibody MAB3381".
Raso et al. (1997) "Intracellular Targeting with Low pH-Triggered Bispecific Antibodies" J Biol Chem 272(44):27623-27628.
Segal et al. (2001) "Introduction: Bispecific Antibodies" J Immunol Meth 248:1-6.
Tang et al. (1999) "Use of a Peptide Mimotope to Guide the Humanization of MRK-16, an Anti-P-Glycoprotein Monoclonal Antibody" J Biol Chem 274(39):27371-27378.
Traunecker et al. (1991) "Bispecific Single Chain Molecules (Janusins) Target Cytotoxic Lymphocytes on HIV Infected Cells" EMBO J 10(12):3655-3659.
UniProtKB/Swiss-Prot accession No. 014793.
UniProtKB/Swiss-Prot accession No. P08476.
UniProtKB/Swiss-Prot Accession No. P48357.
Vaughan et al. (1996) "Human Antibodies with Sub-Nanomolar Affinities Isolated from a Large Non-Immunized Phage Display Library" Nat Biotechnol 14:309-314.
Villanueva and Myers (2008) "Leptin Receptor Signaling and the Regulation of Mammalian Physiology" Int J Obes 32:S8-S12.
Volkel et al. (2001) "Optimized Linker Sequences for the Expression of Monomeric and Dimeric Bispecific Single-Chain Diabodies" Prot Eng 14(10):815-823.
Von Heijne (1983) "Patterns of Amino Acids Near Signal-Sequence Cleavage Sites" Eur J Biochem 133:17-21.
Von Heijne (1986) "A New Method for Predicting Signal Sequence Cleavage Sites" Nucl Acids Res 14(11):4683-4690.
Wren et al. (2002) "SIGNAL-Sequence Information and GeNomic AnaLysis" Comp Meth Prog Biomed 68:177-181.
Wright et al. (2000) "Lymphoid/Neuronal Cell Surface OX2 Glycoprotein Recognizes a Novel Receptor on Macrophages Implicated in the Control of Their Function" Immunity 13:233-242.
Cheung (2014) "A Pegylated Leptin Antagonist Ameliorates CKD-Associated Cachexia in Mice," J Am Soc Nephrol, 25(1): 119-128.
"A Study to Examine the Safety, Tolerability and Biological Effects of REGN4461 in Healthy Volunteers [ClinicalTrials.gov posting, identifier NCT03530514]. Accessed May 21, 2018.".
"Expanded Access to REGN4461 for Patients With 1) Generalized Lipodystrophy, 2) Partial Lipodystrophy or 3) Monogenic Obesity Due to LEP or LEPR Loss of Function [ClinicalTrials.gov posting, identifier NCT04710056]. Accessed Jan. 13, 2021.".
"Study of REGN4461, a Leptin Receptor Agonist Antibody, in Patients with Generalized Lipodystrophy [ClinicalTrials.gov posting, identifier NCT04159415]. Accessed Nov. 12, 2019.".
"Trial of Leptin Replacement Therapy in Patients with Lipodystrophy" [online] Mar. 11, 2009 (retrieved on Aug. 4, 2021), Retrieved from ClinicalTrials.gov, Identifier: NCT00896298 (Year:2009).
2008 Guidance Document "Ethical Considerations for Clinical Trials on Medicinal Products Conducted with the Pediatric Population".
Accession No. NP_001003679.1 To:Protein [Internet]. Bethesda (MD): National Library of Medicine (US), National Center for Biotechnology Information; [2019]—Accession No. NP_001003679.1, ""Leptin Receptor Isoform 3 Precursor [*Homo sapiens*]"", cited on Mar. 12, 2019, [online], [retrieved on Mar. 20, 2019]. Retrieved from: https://www.ncbi.nlm.nih.gov/protein/51093379/, 6 pages.
Accession No. NP_002175.2 To:Protein [Internet]. Bethesda (MD): National Library of Medicine (US), National Center for Biotechnology Information; [2019]—Accession No. NP_002175.2, ""Interleukin-6 Receptor Subunit Beta Isoform 1 Precursor [*Homo sapiens*]"", cited on Mar. 12, 2019, [online], [retrieved on Mar. 20, 2019]. Retrieved from: https://www.ncbi.nlm.nih.gov/protein/NP_002175.2, 6 pages.
Accession No. NP_002294.2 To: Protein [Internet]. Bethesda (MD): National Library of Medicine (US), National Center for Biotechnology Information; [2016]—Accession No. NP_002294.2, "Leptin Receptor Isoform 1 Precursor [*Homo sapiens*]", cited on Oct. 6, 2016, [online], [retrieved on Feb. 15, 2017]. Retrieved from: https://www.ncbi.nlm.nihm.gov/protein/NP_002294.2, 5 pages.
Accession No. XP_005543194.1 Protein [Internet]. Bethesda (MD): National Library of Medicine (US), National Center for Biotechnology Information; [2016]—Accession No. XP_005543194.1, "Leptin Receptor Isoform X1 [Macaca fascicularis]", cited on Jan. 25, 2016, [online], [retrieved on Feb. 15, 2017]. Retrieved from: https://www.ncbi.nlm.nihm.gov/protein/XP_005543194.1, 2 pages.
Addy et al. (2008) "Safety, Tolerability, Pharmacokinetics, and Pharmacodynamic Properties of Taranabant, a Novel Selective Cannabinoid-1 Receptor Inverse Agonist, for the Treatment of Obesity: Results From a Double-blind, Placebo-controlled, Single Oral Dose Study in Healthy Volunteers", J Clin Pharmacol., 48(4): 418-427.

(56) References Cited

OTHER PUBLICATIONS

Ahmann, et al. (2015) "Efficacy and safety of liraglutide versus placebo added to basal insulin analogues (with or without metformin) in patients with type 2 diabetes: a randomized, placebo-controlled trial", Diabetes, Obesity and Metabolism, 17(11): 1056-1064.
Ajluni (2017) "Efficacy and Safety of Metreleptin in Patients with Partial Lipodystrophy: Lessons from an Expanded Access Program", Journal of Diabetes & Metabolism, 7(3): 1000659, 7 pages.
Ajluni et al. (2017) "Spectrum of Disease Associated with Partial Lipodystrophy: Lessons from A Trial Cohort", Clin Endocrinol (Oxf), 86(5): 698-707.
Akinci et al. (2017) "Clinical Presentations, Metabolic Abnormalities and End-Organ Complications in Patients with Familial Partial Lipodystrophy", Metabolism-Clin and Exp., 72: 109-119.
Akinci et al. (2018) "Update on Therapeutic Options in Lipodystrophy", Current Diabetes Reports, 18: 139, pp. 1-12.
Akinci et al. (2018) "Phenotypic and Genetic Characteristics of Lipodystrophy: Pathophysiology, Metabolic Abnormalities, and Comorbidities", Curr Diab Rep., 18(12):143, 1-12.
Akinci et al. (2018) "Renal Complications of Lipodystrophy: A Closer Look at The Natural History of Kidney Disease", Clin Endocrinol (Oxf), 89(1):65-75.
Akinci et al. (2020) "Adipose Tissue, Appetite, and Obesity, Mechanisms and Treatment of Obesity in Humans, The Treatment of Partial Lipodystrophy in the Setting of Neutralizing Antibody Against Metreleptin with Leptin Receptor Agonist REGN4461", Journal of the Endocrine Society, vol. 4, Abstract Supplement, A544 (OR33-02).
Akinci et al. (2020) "The Complicated Clinical Course in A Case of Atypical Lipodystrophy After Development of Neutralizing Antibody to Metreleptin: Treatment with Setmelanotide", Endocrinol Diabetes Metab Case Rep., 1-9.
Al Qaraghuli et al. (2020) "Antibody-Protein Binding and Conformational Changes: Identifying Allosteric Signaling Pathways to Engineer a Better Effector Response", Nature Scientific Reports, 10: 13969.
Al-Attar et al. (2007) "Quantitative and Qualitative Differences in Subcutaneous Adipose Tissue Stores Across Lipodystrophy Types Shown by Magnetic Resonance Imaging", BMC Med Imaging, 7: 3.
Al-Lazikani et al. (1997) "Standard Conformations for the Canonical Structures of Immunoglobulins", J. Mol. Biol. 273: 927-948.
Allen (1999) "The Art, Science and Technology of Pharmaceutical Compounding", in American Pharmacists Association (Washington, D.C., 1999), Introduction pp. xxxii-xxxvii.
Allison et al. (2014) "Connecting Leptin Signaling to Biological Function", Journal of Endocrinology 223: T25-T35.
Altschul et al. (1990) "Basic Local Alignment Search Tool", J. Mol. Biol. 215:403-410.
Altschul (1991) "Amino Acid Substitution Matrices from an Information Theoretic Perspective", J. Mol. Biol., 219: 555-565.
Altschul (1993) "A Protein Alignment Scoring System Sensitive at all Evolutionary Distances", J. Mol. Evol., 36:290-300.
Altschul et al. (1997) "Gapped BLAST and PSI-BLAST: a new generation of protein database search programs", Nucleic Acids Res. 25: 3389-402.
Altschul et al. (2005) "Protein Database Searches Using Compositionally Adjusted Substitution Matrices", FEBS J., 272(20): 5101-5109.
Angrisani et al. (2017) "Bariatric Surgery and Endoluminal Procedures: IFSO Worldwide Survey 2014", Obes Surg., 27(9): 2279-2289.
Anonymus (2019) "Study of REGN4461, a Leptin Receptor Agonist Antibody, in Patient with Generalized Lipodystrophy", Full Text View, ClinicalTrials.gov, Nov. 12, 2019, 10 pages.
Aronis et al. (2011) "Preadipocyte Factor-1 Levels Are Higher in Women with Hypothalamic Amenorrhea and Are Associated with Bone Mineral Content and Bone Mineral Density through a Mechanism Independent of Leptin", J. Clin. Endocrinol. Metab., 96(10): E1634-E1639.
Aslam et al. (2013) "Acquired Generalized Lipodystrophy Associated with Peripheral Tcell Lymphoma with Cutaneous Infiltration", International J. Dermatol., 54: 827-829.
Bahrenberg et al. (2002) "Identification of the Critical Sequence Elements in the Cytoplasmic Domain of Leptin Receptor Isoforms Required for Janus Kinase/Signal Transducer and Activator of Transcription Activation by Receptor Heterodimers", Molecular Endocrinology, 16(4): 859-872.
Barash et al. (1996) "Leptin Is a Metabolic Signal to the Reproductive System", Endocrinology, 137(7): 3144-3147.
Barr et al. (1999) "Subcellular Localization and Internalization of the Four Human Leptin Receptor Isoforms", J Biol Chem., 274(30): 21416-21424.
Barsh & Schwartz (2002) "Genetic Approaches to Studying Energy Balance: Perception and Integration", Nat Rev Genet., 3(8): 589-600.
Bates & Myers (2003) "The Role of Leptin Receptor Signaling in Feeding and Neuroendocrine Function", TRENDS in Endocrinology and Metabolism, 14(10): 447-452.
Bates et al. (2003) "STAT3 Signaling is Required for Leptin Regulation of Energy Balance but not Reproduction", Nature 421: 856-859.
Baumann et al. (1996) "The Full-length Leptin Receptor Has Signaling Capabilities of Interleukin 6-type Cytokine Receptors", Proc Natl Acad Sci USA, 93: 8374-8378.
Bendig (1995) "Humanization of Rodent Monoclonal Antibodies by CDR Grafting", Method3: A Companion to Methods in Enzymology, 8: 83-93.
Bhaskar et al. (2016) "An Allosteric Antibody to the Leptin Receptor Reduces Body Weight and Reverses the Diabetic Phenotype in the Lepob/Lepob Mouse", Obesity 00: (00) 1-8.
Bingham et al. (2008) "Predictors of Acquired Lipodystrophy in Juvenile- Onset Dermatomyositis and a Gradient of Severity", Medicine (Baltimore), 87(2): 70-86.
Bjornholm et al. (2007) "Mice Lacking Inhibitory Leptin Receptor Signals are Lean with Normal Endocrine Function", J. Clin. Invest., 117: 1354-1360.
Boden et al. (1996) "Effect of Fasting on Serum Leptin in Normal Human Subjects", J Clin Endocrinol Metab. 81(9): 3419-3423.
Boersma and Pluckthun (2011) "DARPins and Other Repeat Protein Scaffolds: Advances in Engineering and Applications", Curr. Opin. Biotechnol., 22: 849-857.
Bolan et al. (2002) "Intensive, Long-Term Plasma Exchange Therapy for Severe Hypertriglyceridemia in Acquired Generalized Lipoatrophy", J Clin Endocrinol Metab., 87(1): 380-384.
Bray and Wadden (2015) "Improving Long-Term Weight Loss Maintenance: Can We Do It?", Obesity, 23: 2-3.
Brown et al. (2016) "The Diagnosis and Management of Lipodystrophy Syndromes: A Multi-Society Practice Guideline", J Clin Endocrinol Metab., 101(12): 4500-4511.
Brown et al. (2016) "Lymphoma in Acquired Generalized Lipodystrophy", Leuk Lymphoma, 57(1): 45-50.
Brown et al. (2018) "Long-Term Effectiveness and Safety of Metreleptin in The Treatment of Patients with Generalized Lipodystrophy", Endocrine, 60(3): 479-489.
Buettner et al. (2002) "Definition and Characterization of Relative Hypo- and Hyperleptinemia in a Large Caucasian Population", J Endocrinol. 175(3): 745-756.
Bülbül et al. (2001) "Acute Pancreatitis in A Patient with Partial Lipodystrophy and Membranoproliferative Glomerulonephritis", Nephrol Dial Transplant., 16(9): 1930-1931.
Burakiewicz et al. (2017) "Quantifying Fat Replacement of Muscle by Quantitative MRI in Muscular Dystrophy", J Neurol., 264(10): 2053-2067.
Campfield et al. (1995) "Recombinant Mouse OB Protein: Evidence for a Peripheral Signal Linking Adiposity and Central Neural Networks", Science, 269: 546-549.
Carpenter et al. (1998) "Enhancing Leptin Response by Preventing SH2-containing Phosphate 2 Interaction with Ob Receptor", Proc. Natl. Acad. Sci. USA, 95: 6061-6066.
Carpenter et al. (2012) "Structure of the Human Obesity Receptor Leptin-Binding Domain Reveals the Mechanism of Leptin Antagonism by a Monoclonal Antibody", Structure, 20(3): 487-497.

(56) References Cited

OTHER PUBLICATIONS

Casset et al. (2003) "A Peptide Mimetic of an Anti-CD4 Monoclonal Antibody by Rational Design", Biochemical and Biophysical Research Communications, 307: 198-205.
Ceddia (2005) "Direct Metabolic Regulation in Skeletal Muscle and Fat Tissue by Leptin: Implications for Glucose and Fatty Acids Homeostasis", Int J Obes., 29(10): 1175-1183.
Chagnon et al. (2000) "Associations Between the Leptin Receptor Gene and Adiposity in Middle-Aged Caucasian Males from the HERITAGE Family Study", Journal of Clinical Endocrinology & Metabolism 85(1): 29-34.
Chan et al. (2003) "The Role of Falling Leptin Levels in the Neuroendocrine and Metabolic Adaptation to Short-term Starvation in Healthy Men," J Clin Invest., 111(9): 1409-1421.
Chan et al. (2016) "Immunogenicity Associated with Metreleptin Treatment in Patients with Obesity or Lipodystrophy", Clin Endocrinol., 85(1): 137-149.
Chehab et al. (1996) "Correction of the Sterility Defect in Homozygous Obese Female Mice by Treatment with The Human Recombinant Leptin", Nat Genet., 12: 318-320.
Chen et al. (1996) "Evidence That the Diabetes Gene Encodes the Leptin Receptor: Identification of a Mutation in the Leptin Receptor Gene in db/db Mice", Cell, 84(3): 491-495.
Chothia et al. (1987) "Canonical Structures for The Hypervariable Regions of Immunoglobulins", J. Mol. Biol., 196: 901-917.
Christiansen et al. (2014) "Increased Bone Mineral Content in Patients with Congenital Generalized Lipodystrophy is Unaffected by Metreleptin Replacement Therapy", Endocrine Reviews. 96th Annual Meeting and Expo of the Endocrine Society, ENDO Chicago, IL, USA., 35(3) Abstract No. OR43-6.
Ciofi et al. (2009) "Brain-endocrine Interactions: A Microvascular Route in The Mediobasal Hypothalamus", Endocrinology, 150: 5509-5519.
Clement et al. (1998) "A Mutation in the Human Leptin Receptor Gene Causes Obesity and Pituitary Dysfunction", Nature, 392(6674): 398-401.
Cohen et al. (2001) "Selective Deletion of Leptin Receptor in Neurons Leads to Obesity", J Clin Invest., 108: 1113-1121.
Considine et al. (1996) "Serum Immunoreactive-Leptin Concentrations in Normal-Weight and Obese Humans", N. Engl. J. Med., 334(5): 292-295.
Coppari & BjØrbÆk (2012) "The Potential of Leptin for Treating Diabetes and Its Mechanism of Action", Nat Rev Drug Discov., 11(9): 692-708.
Coppari et al. (2005) "The Hypothalamic Arcuate Nucleus: A Key Site for Mediating Leptin's Effects on Glucose Homeostasis and Locomotor Activity", Cell Metab., 1: 63-72.
Courteix et al. (2007) "Preserved Bone Health in Adolescent Elite Rhythmic Gymnasts Despite Hypoleptinemia", Hormone Research, 68: 20-27.
Cowley et al. (2001) "Leptin Activates Anorexigenic POMC Neurons Through a Neural Network in the Arcuate Nucleus", Nature, 411: 480-484.
Cron et al. (2016) "The Role of gp130 Receptor Cytokines in The Regulation of Metabolic Homeostasis", Journal of Experimental Biology, 219(2): 259-265.
Dalton et al. (2015) "Preliminary Validation and Principal Components Analysis of the Control of Eating Questionnaire (CoEQ) for the Experience of Food Craving", Eur J Clin Nutr., Nature Publishing Group, 69(12): 1313-1317.
Dardeno et al. (2010) "Leptin in Human Physiology and Therapeutics", Front Neuroendocrinol., 31(3): 377-393.
de Luca et al. (2005) "Complete Rescue of Obesity, Diabetes, and Infertility in db/db Mice by Neuron-specific LEPR-B Transgenes", J Clin Invest., 115: 3484-3493.
Deddish et al. (1990) "Carboxypeptidase M in Madin-Darby Canine Kidney Cells", J. Biological Chemistry, 265(25): 15083-15089.
Dembo et al. (1994) "Limit Distribution of Maximal Non-Aligned Two-Sequence Segmental Score", Ann. Prob., 22(4): 2022-2039.
Denroche et al. (2013) "Leptin Administration Enhances Islet Transplant Performance in Diabetic Mice", Diabetes 62: 2738-2746.
Dewall et al. (2008) "Collective and Individual Functions of Leptin Receptor Modulated Neurons Controlling Metabolism and Ingestion", Endocrinology, 149(4): 1773-1785.
Dubern et al. (2012) "Leptin and Leptin Receptor-related Monogenic Obesity", Biochimie., 94(10): 2111-2115.
Ducy et al. (2000) "Leptin Inhibits Bone Formation Through a Hypothalamic Relay: A Central Control of Bone Mass", Cell, 100: 197-207.
Ebihara et al. (2007) "Efficacy and Safety of Leptin-Replacement Therapy and Possible Mechanisms of Leptin Actions in Patients with Generalized Lipodystrophy", J Clin Endocrinol Metab., 92(2): 532-541.
Edwards, et al. (2003) "The Remarkable Flexibility of the Human Antibody Repertoire; Isolation of Over One Thousand Different Antibodies to a Single Protein", BLyS, Journal of Molecular Biology, 334: 103-118.
Ehring (1999) "Hydrogen Exchange/Electrospray Ionization Mass Spectrometry Studies of Structural Features of Proteins and Protein/Protein Interactions", Analytical Biochemistry, 267(2): 252-259.
Eldin et al. (2020) "Healthcare Delivery and Education, Expanding Clinical Considerations for Patient Testing and Care-Pain is a Major Driver of Quality of Life and Psychoemotional Health in Lipodystrophy Syndromes", Journal of the Endocrine Society, MON-121, vol. 4, Abstract Supplementation, A571.
El-Zayadi (2008) "Hepatic Steatosis: a Benign Disease or a Silent Killer", World J Gastroenterol., 14(26): 4120-4126.
Engen and Smith (2001) The Basics of lon Chromatography, Anal. Chem., 73: 256A-265A.
European Publication Notice received for EP Application No. 21207469.4, dated Sep. 14, 2022, 1 page.
Farooqi et al. (1999) "Effects of Recombinant Leptin Therapy in a Child with Congenital Leptin Deficiency", The New England Journal of Medicine, 341(12): 879-884.
Farooqi et al. (2002) "Beneficial Effects of Leptin on Obesity, T cell Hyporesponsiveness, and Neuroendocrine/Metabolic Dysfunction of Human Congenital Leptin Deficiency", The Journal of Clinical Investigation, 110(8): 1093-1103.
Farooqi et al. (2007) "Clinical and Molecular Genetic Spectrum of Congenital Deficiency of the Leptin Receptor", N. Engl. J. Med., 356: 237-247.
Fazeli et al. (2006) "Identification of a Monoclonal Antibody Against the Leptin Receptor that Acts as an Antagonist and Blocks Human Monocyte and T cell Activation", J. Immunol. Methods, 312: 190-200.
Febbraio (2007) "gp130 Receptor Ligands as Potential Therapeutic Targets for Obesity", Journal of Clinical Investigation, 117(4): 841-849.
Federico et al. (2006) "Treatment of Patients with Non-alcoholic Fatty Liver Disease: Current Views and Perspectives", Digestive & Liver Disease, 38(11): 789-801.
Feng et al. (2018) "Roles and Mechanisms of Leptin in Osteogenic Stimulation in Cervical Ossification of the Posterior longitudinal Ligament", Journal of Orthopaedic Surgery and Research, 13: 165, 8 pages.
Fenton et al. (2020) "Rheostat Positions: A New Classification of Protein Positions Relevant to Pharmacogenomics", Medicinal Chemistry Research, 29: 1133-1146.
Festi et al. (2004) "Hepatic Steatosis in Obese Patients: Clinical Aspects and Prognostic Significance", Obes Rev., 5(1): 27-42.
Flak and Myers (2016) "Minireview: CNS Mechanisms of Leptin Action", Mol Endocrinol., 30: 3-12.
Flegal et al. (2016) "Trends in Obesity Among Adults in the United States, 2005 to 2014", JAMA. American Medical Association, 315(21): 2284-2291.
Flint et al. (2000) "Reproducibility, Power and Validity of Visual Analogue Scales in Assessment of Appetite Sensations in Single Test Meal Studies", Int. J. Obes. Relat. Metab. Disord., 24(1): 38-48.

(56) References Cited

OTHER PUBLICATIONS

Foss-Freitas, et al. (2020) "Diagnostic Strategies and Clinical Management of Lipodystrophy", Expert Rev Endocrinol Metab, 15(2): 95-114.
Foster et al. (2003) "Body Weight Regulation by Selective MC4 Receptor Agonists and Antagonists", Ann N.Y. Acad Sci., 994: 103-110.
Franceschini, et al. (1995) "Pre-B Acute Lymphoblastic Leukemia in a Patient with Partial Lipodystrophy and Acanthosis Nigricans", Panminerva Med., 37(4): 248-251.
Friedman and Halaas (1998) "Leptin and the Regulation of Body Weight in Mammals", Nature, 395(6704): 763-770.
Friedman et al. (2014) "20 Years of Leptin: Leptin at 20: An Overview", J Endocrinol., 223(1): T1-T8.
Funcke et al. (2014) "Monogenic Forms of Childhood Obesity Due to Mutations in the Leptin Gene", Mol Cell Pediatr., 1(1): 3.
Garg (2000) "Gender Differences in The Prevalence of Metabolic Complications in Familial Partial Lipodystrophy (Dunnigan Variety)", J Clin Endocrinol Metab., 85(5): 1776-1782.
Garg (2011) "Lipodystrophies: Genetic and Acquired Body Fat Disorders", Journal of Clinical Endocrinology and Metabolism, 96(11): 3313-3325.
Gavrila et al. (2003) "Diurnal and Ultradian Dynamics of Serum Adiponectin in Healthy Men: Comparison with Leptin, Circulating Soluble Leptin Receptor, and Cortisol Patterns," J Clin Endocrinol Metab., 88(6): 2838-2843.
Ge et al. (2018) "Leptin in Depression: A Potential Therapeutic Agent", Cell Death & Disease, 9(11): 1096, 10 pages.
Ghazali et al. (2003) "Bone Mineral Density Directly Correlates with Elevated Serum Leptin in Hemodialysis Patients", Nephrology Dialysis Transplantation, 18: 1882-1890.
Ghorban-Sabbagh et al. (2016) "Correlation Between Serum Leptin and Bone Mineral Density in Hemodialysis Patients", J. Renal Inj. Prev., 5(3): 112-117.
Gibson et al. (2004) "Congenital Leptin Deficiency Due to Homozygosity for the Delta133G Mutation: Report of Another Case and Evaluation of Response to Four Years of Leptin Therapy", J Clin Endocrin. & Metab., 89(10): 4821-4826.
Gish & States (1993) "Identification of Protein Coding Regions by Database Similarity Search", Nature Genet., 3: 266-272.
Goel et al. (2004) "Plasticity Within the Antigen-Combining Site May Manifest as Molecular Mimicry in the Humoral Immune Response", J. Immunol., 173: 7358-7367.
Gonnet et al. (1992) "Exhaustive Matching of the Entire Protein Sequence Database", Science 256: 1443-1445.
Goodson (1984) "Dental Applications in: Medical Applications of Controlled Release vol. II Applications and Evaluation," Chapter 6, Langer and Wise (eds.), CRC Press, pp. 115-138.
Gorska et al. (2010) "Leptin Receptors", European Journal of Medical Research, 15(Supplemental II): 50-54.
Greenfield et al. (2009) "Modulation of Blood Pressure by Central Melanocortinergic Pathways", N Engl J Med., 360: 44-52.
Gromada et al. (2017) "New Isolated Antibody That Binds Human Leptin Receptor (LEPR) and Activates LEPR Signaling Used to Treat Disease Associated with or Caused by Leptin Deficiency or Leptin Resistance e.g. Lipodystrophy, Metabolic Syndrome, and Diabetes", XP55865322, Database Accession No. 2017-288676 Abstract and & US2017/101477 A1, Database WPI [Online Apr. 13, 2017], 3 pages.
Halaas et al. (1995) "Weight-reducing Effects of the Plasma Protein Encoded by the Obese Gene", Science, 269: 543-546.
Halaas et al. (1997) "Physiological Response to Long-term Peripheral and Central Leptin Infusion in Lean and Obese Mice", Proc Natl Acad Sci USA., 94: 8878-8883.
Hall et al. (1978) "Generalised Lipodystrophy, Scleroderma, and Hodgkin's Disease", Arch Intern Med., 138(8): 1303-1304.
Halpern et al. (2010) "Combinations of Drugs in the Treatment of Obesity", Pharmaceuticals, 3: 2398-2415.
Hancock et al. (1994) "SIMPLE34: An Improved and Enhanced Implementation for VAX and Sun Computers of the SIMPLE Algorithm for Analysis of Clustered Repetitive Motifs in Nucleotide Sequences", Comput. Appl. Biosci., 10(1): 67-70.
Handelsman et al. (2013) "The Clinical Approach to The Detection of Lipodystrophy—An AACE Consensus Statement", Endocr Pract., 19(1): 107-16.
Haniu et al. (1998) "Human Leptin Receptor, Determination of Disulfide Structure and N-Glycosylation Sites of the Extracellular Domain*" J Biol Chem., 273(44): 28691-28669.
Haque et al. (2002) "Serum Adiponectin and Leptin Levels in Patients with Lipodystrophies", The Journal of Clinical Endocrinology and Metabolism, 87(5): 2395-2398.
Haque et al. (2002) "Post-Mortem Findings in Familial Partial Lipodystrophy", Dunnigan Variety. Diabet Med., 19(12): 1022-1025.
Harris et al. (1998) "A Leptin Dose-response Study in Obese (ob/ob) and Lean (+/?) Mice", Endocrinology, 139: 8-19.
Hegele (2001) "Premature Atherosclerosis Associated with Monogenic Insulin Resistance", Circulation, 103(18): 2225-2229.
Henikoff et al. (1992) "Amino Acid Substitution Matrices from Protein Blocks", Proc. Natl. Acad. Sci. USA, 89: 10915-10919.
Herrick et al. (2016) "Leptin, Leptin Soluble Receptor, and the Free Leptin Index following a Diet and Physical Activity Lifestyle Intervention in Obese Males and Females", J Obes. Hindawi., 2016(2): 8375828, 5pages.
Heymsfield et al. (1999) "Recombinant Leptin for Weight Loss in Obese and Lean Adults, a Randomized, Controlled, Dose-Escalation Trial", JAMA, 282(16): 1568-1575.
Hochleitner (2000) "Characterization of a Discontinuous Epitope of the Human Immunodeficiency Virus (HIV) Core Protein p24 by Epitope Excision and Differential Chemical Modification Followed by Mass Spectrometric Peptide Mapping Analysis", Protein Science, 9: 487-496.
Hukshorn et al. (2000) "Weekly Subcutaneous Pegylated Recombinant Native Human Leptin (PEG-OB) Administration in Obese Men", J Clin Endocrinol Metab., 85(11): 4003-4009.
Hukshorn et al. (2003) "Pegylated Human Recombinant Leptin (PEG-OB) Causes Additional Weight Loss in Severely Energy-Restricted, Overweight Men", Am J Clin Nutr., 77: 771-776.
Iepsen et al. (2014) "Treatment With a GLP-1 Receptor Agonist Diminishes the Decrease in Free Plasma Leptin During Maintenance of Weight Loss", International Journal of Obesity, 39(5): 834-841.
Jakubke et al. (1985) "Amino Acids, Peptides, Proteins", M. Mir., pp. 93-94 (English translation of the Russian reference).
Jakubke et al. (1985) "Amino Acids, Peptides, Proteins", M. Mir., pp. 93-94 (Russian reference).
Janoschek et al. (2006) "gp130 Signaling in Proopiomelanocortin Neurons Mediates the Acute Anorectic Response to Centrally Applied Ciliary Neurotrophic Factor", PNAS, 103(28): 10707-10712.
Javor et al. (2004) "Proteinuric Nephropathy in Acquired and Congenital Generalized Lipodystrophy: Baseline Characteristics and Course During Recombinant Leptin Therapy", J Clin Endocrinol Metab., 89(7): 3199-3207.
Jing et al. (2016) "Mechanical Vibration Mitigates the Decrease of Bone Quantity and Bone Quality of Leptin Receptor-Deficient Db/Db Mice by Promoting Bone Formation and Inhibiting Bone Resorption", Journal of Bone and Mineral Research, 31(9): 1713-1724.
Junghans et al. (1990) "Anti-Tac-H, a Humanized Antibody to the Interleukin 2 Receptor with New Features for Immunotherapy in Malignant and Immune Disorders", Cancer Res. 50:1495-1502.
Justice et al. (2016) "Using the Mouse to Model Human Disease: Increasing Validity and Reproducibility", Disease, Models & Mechanisms., 9: 101-103.
Kabat et al. (1977) "Unusual Distributions of Amino Acids in Complementarity-Determining (Hypervariable) Segments of Heavy and Light Chains of Immunoglobulins and Their Possible Roles in Specificity of Antibody- Combining Sites", J. Biol. Chem., 252: 6609-6616.
Kabat (1978) "The Structural Basis for Antibody Complementary", Adv. Prot. Chem., 32: 1-75.

(56) References Cited

OTHER PUBLICATIONS

Karlin et al. (1990) "Methods for Assessing the Statistical Significance of Molecular Sequence Features by Using General Scoring Schemes", Proc. Natl. Acad. Sci. USA, 87: 2264-2268.
Karlin et al. (1993) "Applications and Statistics for Multiple High-Scoring Segments in Molecular Sequences", Proc. Natl. Acad. Sci. USA, 90: 5873-5877.
Kawahara et al. (2003) "Bypassing Antibiotic Selection: Positive Screening of Genetically Modified Cells with an Antigen-Dependent Proliferation Switch", Nucleic Acids Research, 31(No. 7 e32): 1-8.
Kawaji et al. (2001) "Anti-leptin Receptor Antibody Mimics the Stimulation of Lipolysis Induced by Leptin in Isolated Mouse Fat Pads", Journal of Lipid Research, 42(10): 1671-1677.
Kazane et al. (2012) "Synthesis of Bispecific Antibodies using Genetically Encoded Unnatural Amino Acids", J. Am. Chem. Soc., 134: 9918-9921 [Epub: Dec. 4, 2012].
Kazane et al. (2013) "Self-Assembled Antibody Multimers through Peptide Nucleic Acid Conjugation", Journal of the American Chemical Society, 135(1): 340-346 [Epub: Dec. 4, 2012]).
Khan et al. (2014) "Adjustable Locks and Flexible Keys: Plasticity of Epitope-Paratope Interactions in Germline Antibodies", J. Immunol. 192: 5398-5405.
Kievet et al. (2013) "Chronic Treatment with A Melanocortin-4 Receptor Agonist Causes Weight Loss, Reduces Insulin Resistance, and Improves Cardiovascular Function in Diet-Induced Obese Rhesus Macaques", Diabetes, 62: 490-497.
Klein et al. (2012) "Progress in overcoming the chain association issue in bispecific heterodimeric IgG antibodies", mAbs 4:6, 653-663.
Klopfenstein et al. (2012) "Comparison of 3 T MRI and CT for the Measurement of Visceral and Subcutaneous Adipose Tissue in Humans", Br J Radiol., 85(1018): e826-30.
Krishna et al. (2009) ""Potent and Selective Agonism of the MelanocortinReceptor 4 with MK-0493 Does Not Induce Weight Loss in Obese Human Subjects: Energy Intake Predicts Lack of Weight Loss Efficacy"", Clin Pharmacol Ther., 86(6): 659-666.
Kufer et al. (2004) "A Revival of Bispecific Antibodies", Trends Biotechnol., 22: 239-244.
Kühnen et al. (2016) "Proopiomelanocortin Deficiency Treated with a Melanocortin-4 Receptor Agonist", N Engl J Med, 375: 240-246.
Kyratsous et al. (2015) "Reply to Dimitrov et al.: VelociSuite Technologies are a Foundation for Rapid Therapeutic Antibody Development", PNAS 112(37): E5116.
Lambert et al. (2001) "Ciliary Neurotrophic Factor Activates Leptin-like Pathways and Reduces Body Fat, Without Cachexia or Rebound Weight Gain, Even in Leptin-Resistant Obesity", PNAS, 98(8): 4652-4657.
Lammert et al. (2001) "Soluble Leptin Receptor Represents the Main Leptin Binding Activity in Human Blood", Biochem Biophys Res Commun., 283(4): 982-988.
Langer (1990) "New Methods of Drug Delivery", Science 249: 1527-1533.
Li et al. (2016) "The Role of Leptin in Central Nervous System Diseases", NeuroReport 27(5): 350-355.
Licinio et al. (2004) "Phenotypic Effects of Leptin Replacement on Morbid Obesity, Diabetes Mellitus, Hypogonadism, and Behavior in Leptin-Deficient Adults", Proc Natl Acad Sci USA., 101(13): 4531-4536.
Lin et al. (2018) "Leptin Signaling Axis Specifically Associates with Clinical Prognosis and is Multifunctional in Regulating Cancer Progression", Oncontarget 9(24): 17210-17219.
Liu et al. (2010) "Acute Administration of Leptin Produces Anxiolytic-like Effects: A Comparison with Fluoxetine", Psychopharmacology, Springer, Berlin, DE, 207(4): 535-545.
Lloyd et al. (2009) "Modeling the Human Immune Response: Performance of a 10(11) Human Antibody Repertoire Against a Broad Panel of Therapeutically Relevant Antigens", Protein Engineering & Selection, 22(3): 159-168.
Lou et al. (2010) "Reduced Body Weight and Increased Energy Expenditure in Transgenic Mice Over-Expressing Soluble Leptin Receptor," PLoS One 5(7): e11669.
Lüdtke et al. (2005) "Hepatic Steatosis in Dunnigan-Type Familial Partial Lipodystrophy", Am J Gastroenterol., 100(10): 2218-2224.
Maccallum et al. (1996) "Antibody-Antigen Interactions: Contact Analysis and Binding Site Topography", J. Mol. Biol., 262: 732-745.
Madden et al. (1996) "Applications of Network BLAST Server", Meth. Enzymol., 266: 131-141.
Mak et al. (2014) "Exploiting the therapeutic potential of leptin signaling in cachexia", Current Opinion in Supportive and Palliative Care, 8(4): 352-357.
Mancour et al. (2012) "Ligand-Induced Architecture of the Leptin Receptor Signaling Complex", Molecular Cell, 48: 655-661.
Mantzoros et al. (2011) "Leptin in Human Physiology and Pathophysiology", Am J. Physiol. Endocrinol. Metab., 301(4): E567-584.
Marcic et al. (2000) "Replacement of the Transmembrane Anchor in Angiotensin I-converting Enzyme (ACE) with a Glycosylphosphatidylinositol Tail Affects Activation of the B2 Bradykinin Receptor by ACE Inhibitors", J. Biol Chem. 275(21):16110-8.
Marks & Cone (2001) "Central Melanocortins and The Regulation of Weight During Acute and Chronic Disease", Recent Prog Horm Res., 56: 359-375.
Marsh et al. (1999) "Effects of Neuropeptide Y Deficiency on Hypothalamic Agouti-Related Protein Expression and Responsiveness to Melanocortin Analogues", Brain Research, 848: 66-77.
Marsh et al. (1999) "Response of Melanocortin-4 Receptor-Deficient Mice to Anorectic and Orexigenic Peptides", Nature Genetics, 21: 119-122.
Martin et al. (1989) "Modeling antibody hypervariable loops: A combined algorithm", Proc. Natl. Acad. Sci. USA, 86: 9268-9272.
Martin et al. (1991) "Molecular Modeling of Antibody Combining Sites", Methods Enzymol., 203: 121-153.
Mashkovsky (2012) "Drugs" 16th ed., revised, corrected and supplemented, M.: New Wave pp. 12-13 (English translation of the Russian reference).
Mashkovsky (2012) "Drugs" 16th ed., revised, corrected and supplemented, M.: New Wave pp. 12-13 (Russian reference).
Mayo Clinic (2015) "Lipodystrophy Syndromes: New Treatment, Newer Questions", Published online Sep. 1, 2015, 4 pages.
Mazen, et al. (2011) "Homozygosity for a Novel Missense Mutation in the Leptin Receptor Gene (P316T) in two Egyptian Cousins with Severe Early Onset Obesity", Molecular Genetics and Metabolism, 102: 461-464.
McDuffie et al. (2004) "Effects of Exogenous Leptin on Satiety and Satiation in Patients with Lipodystrophy and Leptin Insufficiency", J. Clin. Endocrinol. Metab., 89(9): 4258-4263.
McMurphy et al., (2014) "The Anti-Tumor Activity of a Neutralizing Nanobody Targeting Leptin Receptor in a Mouse Model of Melanoma", PLOS One (2014) 9(2): e89895.
Meehan et al. (2016) "Metreleptin for Injection to Treat the Complications of Leptin Efficiency in Patients with Congenital or Acquired Generalized Lipodystrophy", Clinical Pharmacology, 9(1): 59-68.
Minicocci et al. (2012) "Mutations in the ANGPTL3 Gene and Familial Combined Hypolipidemia: A Clinical and Biochemical Characterization," J Clin Endocrinol Metab., 97(7): E1266-1275.
Mironov et al. (2012) "Guidelines for Conducting Preclinical Studies of Drugs, Part One", M.:Grif and K, pp. 858-860, table 2 (English translation of the Russian reference).
Mironov et al. (2012) "Guidelines for Conducting Preclinical Studies of Drugs, Part One", M.:Grif and K, pp. 858-860, table 2 (Russian reference).
Misra et al. (2003) "Clinical Features and Metabolic Derangements in Acquired Generalized Lipodystrophy: Case Reports and Review of The Literature", Medicine (Baltimore), 82(2): 129-146.
Misra et al. (2004) "Clinical Features and Metabolic and Autoimmune Derangements in Acquired Partial Lipodystrophy: Report Of 35 Cases and Review of The Literature", Medicine (Baltimore), 83(1): 18-34.

(56) References Cited

OTHER PUBLICATIONS

Molek, et al. ( 2014) "Screening of synthetic phage display scFv libraries yields competitive ligands of human leptin receptor", Biochemical and Biophysical Research Communications, 452(3): 479-483.
Molina et al. (2014) "Pressure Ulcers—Burns/Annals of Physical Rehavilitation Medicine", Lipoatrophia Semicircularis: A case report ABSTRACT P159-e, 57S : e212-e217.
Montague et al. (1997) "Congenital Leptin Deficiency is Associated with Severe Early-onset Obesity in Humans," Nature, 387(6636): 903-908.
Moon et al. (2013) "Leptin's Role in Lipodystrophic and Nonlipodystrophic Insulin-Resistant and Diabetic Individuals", Endocrine Reviews, 34(3): 377-412.
Mordenti et al. (1991) "Interspecies Scaling of Clearance and vol. of Distribution Data for Five Therapeutic Proteins", Pharmaceut. Res. 8:1351.
Mori et al. (2004) "Socs3 Deficiency in the Brain Elevates Leptin Sensitivity and Confers Resistance to Diet-Induced Obesity", Nature Medicine, 10(7): 739-743.
Morris & Rui (2009) "Recent Advances in Understanding Leptin Signaling and Leptin Resistance", Am J Physiol Endocrinol Metab., 297(6): E1247-59.
Morris et al. (1996) "Epitope Mapping of Protein Antigens by Competition ELISA", The Protein|Protocols Handbook, Humana Press, pp. 595-600.
Mould and Green (2010) "Pharmacokinetics and Pharmacodynamics of Monoclonal Antibodies," BioDrugs, 24(1): 29-39.
Muniyappa et al. (2017) "Metreleptin Therapy Lowers Plasma Angiopoietin-like Protein 3 in Patients with Generalized Lipodystrophy", Journal of Clin Lipidol., 11(2): 543-550.
Murphy et al. (2014) "Mice with Megabase Humanization of their Immunoglobulin Genes GenerateAntibodies as Efficiently as Normal Mice", PNAS, 111(14): 5153-5158.
Muzzin et al. (1996) "Correction of Obesity and Diabetes in Genetically Obese Mice by Leptin Gene Therapy", Proc Natl Acad Sci USA., 93: 14804-14808.
Ng et al. (2014) "Global, Regional, and National Prevalence of Overweight and Obesity in Children and Adults During 1980-2013: A Systematic Analysis for the Global Burden of Disease Study 2013", Lancet 384(9945): 766-781.
Nidhina Haridas (2015) "Regulation of Angiopoietin-Like Proteins (ANGPTLs) 3 and 8 by Insulin", J Clin Endocrinol Metab., 100(10): E1299-1307.
Nolis (2014) "Exploring the Pathophysiology Behind the More Common Genetic and Acquired Lipodystrophies", Journal of Human Genetics, 59 : 16-23.
Norsted et al. (2008) "Protein Components of the Blood-brain Barrier (BBB) in the Mediobasal Hypothalamus", Journal of Chemical Neuroanatomy, 36: 107-121.
Oral "Clinical Protocol to Investigate the Efficacy of Recombinant Human Leptin (Metreleptin) in Nonalcoholic Steatohepatitis (NASH) or Nonalcoholic Fatty Liver Disease (NAFLD) Associated With Lipodystrophy", University of Michigan, Oct. 8, 2012, 12 pages, [online]: U.S. National Library of Medicine, retrieved on Oct. 7, 2019, ClinicalTrials.gov Identified NCT01679197.
Oral "Clinical Protocol to Investigate the Long-term Safety and Efficacy of Metreleptin in Various Forms of Partial Lipodystrophy", University of Michigan, Sep. 29, 2015, 8 pages, [online] U.S. National Library of Medicine, retrieved on Oct. 28, 2021, ClinicalTrials.gov Identifier: NCT02654977.
Oral & Chan (2010) "Rationale for Leptin-Replacement Therapy for Severe Lipodystrophy", Endocr Pract., 16(2): 324-333.
Oral et al. (2002) "Leptin-Replacement Therapy for Lipodystrophy", N Engl J Med., 346(8): 570-578.
Oral et al. (2019) "Long-Term Effectiveness and Safety of Metreleptin in The Treatment of Patients with Partial Lipodystrophy", Endocrine, 64(3): 500-511.
Osorio (2014) "Leptin and Leptin Receptor Expressions in Prostate Tumors May Predict Disease Aggressiveness?", Acta Cirurgica Brasileira, 29(supl.3), 5pages.
O'Sullivan et al. (2007) "Cytokine Receptor Signaling Through the Jak-Stat-Socs Pathway in Disease," Mol. Immunol., 44(10): 2497-2506
Ottaway et al. (2015) "Diet-Induced Obese Mice Retain Endogenous Leptin Action", Cell Metabolism, 21:877-882.
Özen et al.(2020) "Current Diagnosis, Treatment and Clinical Challenges in the Management of|Lipodystrophy Syndromes in Children and Young People", J Clin Res Pediatr Endocrinol, 12(1):17-28.
Özsu et al. (2017) "Early-onset Severe Obesity Due to Complete Deletion of the Leptin Gene in a Boy", J Pediatr Endocrinol Metab., 30(11): 1227-1230.
Padlan (1994) "Anatomy of the Antibody Molecule", Molecular Immunology, 31(3): 169-217.
Park and Ahima (2014) "Leptin Signaling", F1000Prime Reports, 73(6), 8 pages.
Patni and Garg (2015) "Congenital Generalized Lipodystrophies—New Insights into Metabolic Dysfunction", Nat Rev Endocrinol., 11: 522-534.
Paul (1993) "Fundamental Immunology", 3rd Edition, Laboratory of Immunology National Institute of Allergy and Infection Diseases National Institutes of Health, pp. 292-295.
Paz-Filho et al. (2011) "Ten Years of Leptin Replacement Therapy", Obesity Reviews, 12: e315-e323.
Paz-Filho, et al. (2014) "Leptin treatment: Facts and expectations", Metabolism, pp. 1-11, http://dx.doi.org/10.1016/j.metabol.2014.07.014.
PCT International Search Report and Written Opinion for International application No. PCT/US2018/066075 mailed Feb. 25, 2019.
PCT International Search Report and Written Opinion received for PCT/US2016/056465, on Jan. 10, 2017.
PCT International Search Report and Written Opinion received for PCT/US2017/060690 on Jan. 10, 2018, 17 pages.
PCT International Search Report from PCT/US2019/026173 dated Jul. 30, 2019, 15 pages.
Pearson (1994) "Using the FASTA Program to Search Protein and DNA Sequence Databases", Methods Mol. Biol. 24: 307-331.
Pearson (2000) "Flexible Sequence Similarity Searching with the FASTA3 Program Package", Methods in Molecular Biology, 132: 185-219.
Pedersen et al. (1992) "Antibody Modeling: Beyond Homology", Immunomethods, 1(2): 126-136.
Peelman et al. (2014) "Insights into Signaling Assemblies of the Leptin Receptor", Journal of Endocrinology, 223: T9-T23.
Pelleymounter et al. (1995) "Effects of the Obese Gene Product on Body Weight Regulation in ob/ob Mice", Science, 269: 540-543.
Phillips (2001) "The Challenge of Gene Therapy and DNA Delivery", J. Pharm. Pharmacology, 53: 1169-1174.
Poosarla et al. (2017) "Computational De Novo Design of Antibodies Binding to a Peptide With HighAffinity", Biotechn. Bioeng., 114(6): 1331-1342.
Powell et al. (1998) "Compendium of Excipients for Parenteral Formulations", PDA (1998) J. Pharm. Sci. Technol., 52: 238-311.
Powell et al. (2011) "New Drug Targets for the Treatment of Obesity", Clin. Pharmacol. Ther., 90(1): 40-51.
Procaccini et al. (2015) "Leptin in Autoimmune Diseases", Metabolism Clinical and Experimental, 64: 92-104.
Purdham et al. (2007) "A Neutralizing Leptin Receptor Antibody Mitigates Hypertrophy and Hemodynamic Dysfunction in the Postinfarcted Rat Heart", Am. J. Physiol. Heart Circ. Physiol., 295(1): H441-H446.
Rabia et al. (2018) "Understanding and Overcoming Trade-Offs Between Antibody Affinity, Specificity, Stability and Solubility", Biochemical Engineer Journal, 137: 365-374.
Ravussin et al. (2009) "Enhanced Weight Loss with Pramlintide/Metreleptin: An IntegratedNeurohormonal Approach to Obesity Pharmacotherapy", Obesity, 17(9): 1736-1743.
Ravussin et al. (2014) "A Missing Link in Bodyweight Homeostasis: The Catabolic Signal of the Overfed State", Cell Metab., 20(4): 565-572.

(56) References Cited

OTHER PUBLICATIONS

Rebouissou et al. (2009) "Frequent In-Frame Somatic Deletions Activate GP130 in Inflammatory|Hepatocellular Tumours," Nature, 457(7226): 200-205.
Reddy et al., (2000) "Elimination of Fc Receptor-Dependent Effector Functions of a Modified IgG4 Monoclonal Antibody to Human CD4", J. Immunol. 164:1925-1933.
Reineke (2004) "Antibody Epitope Mapping Ussing Arrays of Synthetic Peptides," Methods Mol. Biol., 248: 443-463.
Rhythm Pharma. Press Release, PRNewswire, Rhythm Presents Cardiovascular Safety Data from Phase 1b/2a Clinical Trials of Setmelanotide in Obesity (Nov. 6, 2015).
Roemmich et al. (2003) "Relationship of Leptin to Bone Mineralization in Children and Adolescents", J. Clin. Endocrinol. Metab., 88(2): 599-604.
Rosenbaum et al. (2002) "Low Dose Leptin Administration Reverse Effects of Sustained Weight-Reduction on Energy Expenditure and Circulating Concentrations of Thyroid Hormones", The Journal of Clinical Endocrinology & Metabolism 87(5): 2391-2394.
Rosenbaum, et al. (2005) "Low-dose Leptin Reverses Skeletal Muscle, Autonomic, and Neuroendocrine Adaptations to Maintenance of Reduced Weight" The Journal of Clinical Investigation 115(12):3579-3586.
Ruhl and Everhart (2001) "Leptin Concentrations in the United States: Relations with Demographic and Anthropometric Measures", Am J Clin Nutr., 74(3): 295-301.
Savage et al. (2009) "Complement Abnormalities in Acquired Lipodystrophy Revisited", J Clin Endocrinol Metab., 94(1): 10-16.
Schoeller et al. (1997) "Entrainment of the Diurnal Rhythm of Plasma Leptin to Meal Timing", J Clin Invest., 100(7): 1882-1887.
Schurgin et al. (2004) "Endocrine and Metabolic Effects of Physiologic r-metHuLeptin Administration during Acute Caloric Deprivation in Normal-Weight Women", J Clin Endocrinol Metab., 89(11): 5402-5409.
Sefton (1987) "Implantable Pumps", Crc Crit. Ref. Biomed. Eng. 14: 201-240.
Selezneva et al. (2015) "Complex Approach to Study Pharmacological Agents In Vitro, Ex Vivo, In Vivo", International Research Journal, 6(37): 125-127 in Russian with English Abstract.
Shetty et al. (2011) "Leptin Administration to Overweight and Obese Subjects for Six Months Increases Free Leptin Concentrations but Does not Alter Circulating Hormones of the Thyroid and IGF Axes During Weight Loss Induced by a Mild Hypocaloric Diet", Eur. J Endocrinol., 165(2): 249-254.
Shields et al. (2002) "Lack of Fucose on Human IgG1 N-Linked Oligosaccharide Improves Binding to Human FcγRIII and Antibody-dependent Cellular Toxicity", JBC, 277: 26733-26740.
Shimomura et al. (1998) "Insulin Resistance and Diabetes Mellitus in Transgenic Mice Expressing Nuclear SREBP-1c in Adipose Tissue: Model for Congenital Generalized Lipodystrophy", Genes Dev., 12: 3182-3194.
Shimomura et al. (1999) "Leptin Reverses Insulin Resistance and Diabetes Mellitus in Mice with|Congenital Lipodystrophy", Nature 401: 73-76.
Sienkiewicz et al. (2011) "Long-term Metreleptin Treatment Increases Bone Mineral Density and Content at the Lumbar Spine of Lean Hypoleptinemic Women", Metabolism Clinical and Experimental, 60: 1211-1221.
Simha et al. (2002) "Effect of Subcutaneous Leptin Replacement Therapy on Bone Metabolism in Patients with Generalized Lipodystrophy", The Journal of Clinical Endocrinology and Metabolism, 87(11): 4942-4945.
Simha (2014) "Metreleptin for Metabolic Disorders Associated with Generalized or Partial Lipodystrophy", Expert Rev. Endocrinol. Metab., 9(3): 205-212.
Sinha et al. (1996) "Evidence of Free and Bound Leptin in Human Circulation", The Journal of Clinical Investigation, 98(6): 1277-1282.
Sjöström (1998) "Randomised Placebo-controlled Trial of Orlistat for Weight Loss and Prevention of Weight Regain in Obese Patients", Lancet 352(9123): 167-172.
Smith et al. (1975) "Lipodystrophy, Pancreatitis, And Eosinophilia", Gut., 16(3): 230-234.
Smith et al. (2010) "Multicenter, Placebo-Controlled Trial of Lorcaserin for Weight Management", N. Engl. J. Med., 363(3): 245-256.
States et al. (1991) "Improved Sensitivity of Nucleic Acid Database Searches Using Application-Specific Scoring Matrices", Methods, 3: 66-70.
Stears et al. (2014) "Diagnosis and Management of Lipodystrophy: a Practical Update", Clinical Lipidology, 9(2): 235-259.
Stefater et al. (2012) "The Anorectic Effect of CNTF Does Not Require Action in Leptin-Responsive Neurons", Endocrinology, 153(6): 2647-54.
Stoner "Setemelanotide in a Single Patient with Partial Lipodystrophy," Rhythm Pharmaceuticals, Inc., Ann Arbor, MI, Aug. 25, 2017, 5 pages, [online] U.S. National Library of Medicine, retrieved on Sep. 10, 2019, ClinicalTrials.gov Identifier: NCT03262610.
Suthaus et al. (2010) "Forced Homo- and Heterodimerization of all gp130-type Receptor Complexes Leads to Constitutive Ligand-Independent Signaling and Cytokine-Independent Growth", Mol. Biol. Cell., 1(15): 2797-807.
Sweeney (2002) "Leptin Signalling", Cell Signal, 14(8): 655-663.
Taga et al. (1997) "Gp130 and the interleukin-6 family of cytokines", Annu. Rev. Immunol, 15: 797-819.
Tartaglia et al., (1995) "Identification and Expression Cloning of a Leptin Receptor, OB-R", Cell, 83(7):1263-1271.
Tartaglia et al. (1996) "The Full-length Leptin Receptor Has Signaling Capabilities of Interleukin 6-type Cytokine Receptors", Proc Natl Acad Sci USA., 93: 8374-8378.
Tartaglia (1997) "The Leptin Receptor", J. Biol. Chem 7:272(10):6093-6096.
Taylor et al. (1992) "A Transgenic Mouse that Expresses a Diversity of Human Sequence Heavy and Light Chain Immunoglobulins", Nucl. Acids Res. 20: 6287-6295.
Tikka (2016) "The Role of ANGPTL3 in Controlling Lipoprotein Metabolism", Endocrine, 52(2): 187-193.
Tokuriki et al. (2009) "Stability Effects of Mutations and Protein Evolvability", Current Opinion Struc. Biol., 19: 596-604.
Tomer (2000) "Characterization of a Discontinuous Epitope of the Human Immunodeficiency Virus (HIV) Core Protein p24 by Epitope Excision and Differential Chemical Modification Followed by Mass Spectrometric Peptide Mapping Analysis", Protein Science, 9: 487-496.
Tutt et al. (1991) "Trispecific $F(ab')_3$ Derivatives that use Cooperative Signaling via the TCR/CD3 Complex and CD2 to Activate and Redirect Resting Cytotoxic T Cells", J. Immunol. 147:60-69.
Tyagi and Gupta (1998) "Chemical Modification and Chemical Crosslinking for Protein/Enzyme Stabilization", Biochemistry, 63(3): 395-407 (English Abstract).
Tyagi and Gupta (1998) "Chemical Modification and Chemical Crosslinking for Protein/EnzymeStabilization", Biochemistry, 63(3): 395-407 (Russian reference).
UK Working Party on Acute Pancreatitis (2005) "UK Guidelines for the Management of Acute Pancreatitis", Gut.; 54 (Suppl 3): iii1-iii9.
Ungerleider et al. (2013) "Increased Activin Bioavailability Enhances Hepatic Insulin Sensitivity While Inducing Haptic Steatosis in Male Mice", Endocrinology, 154(6): 2025-2033.
University of Utah Healthcare (2014) "Knowing the Difference Between Inherited and Acquired Cancers Can Save Lives", Published online Sep. 5, 2014, 3 pages.
Upadhyay (2015) "The Role of Leptin in Regulating Bone Metabolism", Metabolism, 64(1): 105-113.
Ussar et al. (2011) "Receptor Antibodies as Novel Therapeutics for Diabetes", Science Translational Medicine, 3(113): 22-24.
Vajdos et al. (2002) "Comprehensive Functional Maps of the Antigen-binding Site of an Anti-ErbB2 Antibody Obtained with Shotgun Scanning Mutagenesis", J. Mol. Biol., 320: 415-428.
Valenzuela et al. (2003) "High-throughput Engineering of the Mouse Genome Coupled with High-Resolution Expression Analysis", Nature Biotechnology, 21(6): 652-659.

(56) References Cited

OTHER PUBLICATIONS

Van Der Klaauw & Farooqi (2015) "The Hunger Genes: Pathways to Obesity", Cell., 161(1): 119-132.
Van Dielen et al. (2002) "Leptin and Soluble Leptin Receptor Levels in Obese and Weight-Losing Individuals", J Clin Endocrinol Metab., 87(4): 1708-1716.
Van Maldergem et al. (2002) "Genotype-Phenotype Relationships in Berardinelli-Seip Congenital Lipodystrophy", J Med Genet., 39(10): 722-733.
Wabitsch et al. (2015) "Severe Early-Onset Obesity Due to Bioinactive Leptin Caused by a p.N103K Mutation in the Leptin Gene", J Clin Endocrinol Metab., 100(9): 3227-3230.
Warren et al. (1999) "Functional Hypothalamic Amenorrhea: Hypoleptinemia and Disordered Eating", The Journal of Clinical Endocrinology & Metabolism, 84(3): 873-877.
Wauman & Tavernier (2011) "Leptin Receptor Signaling: Pathways to Leptin Resistance", Frontiers in Bioscience, 16: 2771-2793.
Welt et al. (2004) "Recombinant Human Leptin in Women with Hypothalamic Amenorrhea", N. Engl. J. Med., 351: 987-997.
White and Tartaglia (1996) "Leptin and OB-R: Body Weight Regulation by a Cytokine Receptor", Cytokine & Growth Factor Reviews, 7(4): 303-309.
Wikberg & Mutulis (2008) "Targeting Melanocortin Receptors: An Approach to Treat Weight Disorders and Sexual Dysfunction", Nat Rev Drug Discov., 7(4): 307-323.
Wootton et al. (1993) "Statistics of Local Complexity in Amino Acid Sequences and Sequence Databases", Comput. Chem., 17:149-163.
Wu et al. (1987) "Receptor-Mediated in Vitro Gene Transformation by a Soluble DNA Carrier System" J. Biol. Chem. 262:4429-4432.
Wu et al. (1999) "Humanization of a Murine Monoclonal Antibody by Simultaneous Optimization of Framework and CDR Residues", J. Mol. Biol., 294: 151-162.
Yadav and Pitchumoni (2003) "Issues in Hyperlipidemic Pancreatitis", J Clinical Gastroenterol., 36(1): 54-62.
Yiannias et al. (2006) "Peripheral T-Cell Lymphoma Presenting as Lipoatrophy and Nodules", Int J Dermatol., 45(12): 1415-1419.
Yue et al. (2016) "Leptin Receptor Promotes Adipogenesis and Reduces Osteogenesis by Regulating Mesenchymal Stromal Cells in Adult Bone Marrow", Cell Stem Cell, 18(6): 782-796.
Zabeau et al. (2003) "The Ins and Outs of Leptin Receptor Activation", FEBS Letters, 546: 45-50.
Zabeau et al. (2014) "Antagonizing Leptin: Current Status and Future Directions", Biol. Chem., 395(5): 499-514.
Zabeau et al. (2015) "Leptin: From Structural Insights to the Design of Antagonists", Life Sciences, 140: 49-56.
Zadeh et al. (2013) "The Liver Diseases of Lipodystrophy: The Long-term Effect of Leptin Treatment", J Hepatol., 59(1): 131-137.
Zhang et al. (1994) "Positional Cloning of the Mouse Obese Gene and Its Human Homologue", Nature, 372: 425-432.
Zhang et al. (1997) "PowerBLAST: A New Network BLAST Application for Interactive or Automated Sequence Analysis and Annotation", Genome Res., 7: 649-656.
Zhang et al. (2016) "Characteristics of Patients Potentially Eligible for Pharmacotherapy for Weight Loss in Primary Care Practice in the United States", Obes Sci Pract., 2(2): 104-114.
Zhao et al. (2014) "Leptin and IL-6 Family Cytokines Synergize to Stimulate Müller Glia Reprogramming and Retina Regeneration," Cell Reports, 9(1): 272-284.
Zuchero et al. (2016) "Discovery of Novel Blood-Brain Barrier Targets to Enhance Brain Uptake of Therapeutic Antibodies", Neuron, 89: 70-82.
Park et al. (2007) "Long-Term Efficacy of Leptin Replacement in Patients with Dunningan-Type Familial Partial Lipodystrophy," Metabolism Clinical and Experimental, 56:508-516.

* cited by examiner

SEQUENCE LISTING

<160> NUMBER OF SEQ ID NOS: 30

<210> SEQ ID NO 1
<211> LENGTH: 117
<212> TYPE: PRT
<213> ORGANISM: Homo sapiens

<400> SEQUENCE: 1

Glu Val Gln Leu Val Glu Ser Gly Gly Ser Val Val Arg Pro Gly Glu
1 5 10 15

Ser Leu Arg Leu Ser Cys Ala Ala Ser Gly Phe Thr Phe Asp Asp Tyr
20 25 30

Gly Met Ser Trp Val Arg Gln Ala Pro Gly Lys Gly Leu Glu Trp Val
35 40 45

Ser Gly Ile Ser Trp Asn Gly Gly Ile Thr Val Tyr Ala Asp Ser Val
50 55 60

Lys Gly Arg Phe Thr Val Ser Arg Asp Asn Ala Lys Asn Ser Leu Tyr
65 70 75 80

Leu Gln Met Asn Ser Leu Arg Ala Glu Asp Thr Ala Leu Tyr His Cys
85 90 95

Ala Arg Ala Arg Tyr Gly Gly Ala Asp Tyr Trp Gly Gln Gly Thr Leu
100 105 110

Val Thr Val Ser Ser
115

<210> SEQ ID NO 2
<211> LENGTH: 108
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Pro
85 90 95

Ile Thr Phe Gly Gln Gly Thr Arg Leu Glu Ile Lys
100 105

<210> SEQ ID NO 3
<211> LENGTH: 6
<212> TYPE: PRT
<213> ORGANISM: Homo sapiens

<400> SEQUENCE: 3

Gln Ser Ile Ser Ser Tyr
1 5

<210> SEQ ID NO 4
<211> LENGTH: 3
<212> TYPE: PRT
<213> ORGANISM: Homo sapiens

<400> SEQUENCE: 4

Ala Ala Ser
1

<210> SEQ ID NO 5
<211> LENGTH: 10
<212> TYPE: PRT
<213> ORGANISM: Homo sapiens

<400> SEQUENCE: 5

Gln Gln Ser Tyr Ser Thr Pro Pro Ile Thr
1 5 10

<210> SEQ ID NO 6
<211> LENGTH: 8
<212> TYPE: PRT
<213> ORGANISM: Homo sapiens

<400> SEQUENCE: 6

Gly Phe Thr Phe Asp Asp Tyr Gly
1 5

<210> SEQ ID NO 7
<211> LENGTH: 8
<212> TYPE: PRT
<213> ORGANISM: Homo sapiens

<400> SEQUENCE: 7

Ile Ser Trp Asn Gly Gly Ile Thr
1 5

<210> SEQ ID NO 8
<211> LENGTH: 10
<212> TYPE: PRT
<213> ORGANISM: Homo sapiens

<400> SEQUENCE: 8

Ala Arg Ala Arg Tyr Gly Gly Ala Asp Tyr
1 5 10

<210> SEQ ID NO 9
<211> LENGTH: 120
<212> TYPE: PRT
<213> ORGANISM: Homo sapiens

<400> SEQUENCE: 9

Glu Val Gln Val Leu Glu Ser Gly Gly Asp Leu Val Gln Pro Gly Gly
1 5 10 15

Ser Leu Arg Leu Ser Cys Ala Ala Ser Gly Phe Thr Phe Ser Ala Tyr
20 25 30

Ala Met Thr Trp Val Arg Gln Ala Pro Gly Lys Gly Leu Glu Trp Val
35 40 45

Ser Ala Ile Ser Gly Ser Gly Gly Ser Ala Tyr Tyr Ala Asp Ser Val
50 55 60

Lys Gly Arg Phe Thr Ile Ser Arg Asp Asn Ser Lys Asn Thr Val Tyr
65 70 75 80

Leu Gln Met Asn Ser Leu Arg Ala Glu Asp Thr Ala Val Tyr Tyr Cys
85 90 95

Ala Lys Asp Gly Ala Trp Lys Met Ser Gly Leu Asp Val Trp Gly Gln
100 105 110

```
Gly Thr Thr Val Ile Val Ser Ser
        115                 120


<210> SEQ ID NO 10
<211> LENGTH: 107
<212> TYPE: PRT
<213> ORGANISM: Homo sapiens

<400> SEQUENCE: 10

Asp Ile Gln Met Thr Gln Ser Pro Ala Ser Leu Ser Ala Ser Val Gly
1               5                   10                  15

Asp Arg Val Thr Ile Thr Cys Arg Ala Ser Gln Asp Ile Ser Asp Tyr
            20                  25                  30

Leu Ala Trp Tyr Gln Gln Lys Pro Gly Lys Ile Pro Arg Leu Leu Ile
        35                  40                  45

Tyr Thr Thr Ser Thr Leu Gln Ser Gly Val Pro Ser Arg Phe Arg Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asp Ser Ala Pro Leu
                85                  90                  95

Thr Phe Gly Gly Gly Thr Lys Val Glu Ile Lys
            100                 105


<210> SEQ ID NO 11
<211> LENGTH: 6
<212> TYPE: PRT
<213> ORGANISM: Homo sapiens

<400> SEQUENCE: 11

Gln Asp Ile Ser Asp Tyr
1               5


<210> SEQ ID NO 12
<211> LENGTH: 3
<212> TYPE: PRT
<213> ORGANISM: Homo sapiens

<400> SEQUENCE: 12

Thr Thr Ser
1


<210> SEQ ID NO 13
<211> LENGTH: 9
<212> TYPE: PRT
<213> ORGANISM: Homo sapiens

<400> SEQUENCE: 13

Gln Lys Tyr Asp Ser Ala Pro Leu Thr
1               5


<210> SEQ ID NO 14
<211> LENGTH: 8
<212> TYPE: PRT
<213> ORGANISM: Homo sapiens

<400> SEQUENCE: 14

Gly Phe Thr Phe Ser Ala Tyr Ala
1               5


<210> SEQ ID NO 15
<211> LENGTH: 8
```

<212> TYPE: PRT
<213> ORGANISM: Homo sapiens

<400> SEQUENCE: 15

Ile Ser Gly Ser Gly Gly Ser Ala
1               5

<210> SEQ ID NO 16
<211> LENGTH: 13
<212> TYPE: PRT
<213> ORGANISM: Homo sapiens

<400> SEQUENCE: 16

Ala Lys Asp Gly Ala Trp Lys Met Ser Gly Leu Asp Val
1               5                   10

<210> SEQ ID NO 17
<211> LENGTH: 126
<212> TYPE: PRT
<213> ORGANISM: Homo sapiens

<400> SEQUENCE: 17

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Ser His
            20                  25                  30

Phe Trp Ser Trp Ile Arg Gln Pro Pro Gly Lys Gly Leu Glu Trp Ile
        35                  40                  45

Gly Tyr Ile Leu Tyr Thr Gly Gly Thr Ser Phe Asn Pro Ser Leu Lys
    50                  55                  60

Ser Arg Val Ser Met Ser Val Gly Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Ser Gly Ile Thr Phe Thr Gly Ile Ile Val Pro Gly Ser
            100                 105                 110

Phe Asp Ile Trp Gly Gln Gly Thr Met Val Thr Val Ser Ser
        115                 120                 125

<210> SEQ ID NO 18
<211> LENGTH: 108
<212> TYPE: PRT
<213> ORGANISM: Homo sapiens

<400> SEQUENCE: 18

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 19
<211> LENGTH: 7
<212> TYPE: PRT
<213> ORGANISM: Homo sapiens

<400> SEQUENCE: 19

Gln Ser Val Ser Ser Ser Tyr
1               5

<210> SEQ ID NO 20
<211> LENGTH: 3
<212> TYPE: PRT
<213> ORGANISM: Homo sapiens

<400> SEQUENCE: 20

Gly Ala Ser
1

<210> SEQ ID NO 21
<211> LENGTH: 9
<212> TYPE: PRT
<213> ORGANISM: Homo sapiens

<400> SEQUENCE: 21

Gln Gln Tyr Gly Ser Ser Pro Trp Thr
1               5

<210> SEQ ID NO 22
<211> LENGTH: 8
<212> TYPE: PRT
<213> ORGANISM: Homo sapiens

<400> SEQUENCE: 22

Gly Gly Ser Phe Ser Ser His Phe
1               5

<210> SEQ ID NO 23
<211> LENGTH: 7
<212> TYPE: PRT
<213> ORGANISM: Homo sapiens

<400> SEQUENCE: 23

Ile Leu Tyr Thr Gly Gly Thr
1               5

<210> SEQ ID NO 24
<211> LENGTH: 20
<212> TYPE: PRT
<213> ORGANISM: Homo sapiens

<400> SEQUENCE: 24

Ala Arg Ala Arg Ser Gly Ile Thr Phe Thr Gly Ile Ile Val Pro Gly
1               5                   10                  15

Ser Phe Asp Ile
            20

<210> SEQ ID NO 25
<211> LENGTH: 444
<212> TYPE: PRT
<213> ORGANISM: Homo sapiens

<400> SEQUENCE: 25

Glu Val Gln Leu Val Glu Ser Gly Gly Ser Val Val Arg Pro Gly Glu

-continued 1 5 10 15

Ser Leu Arg Leu Ser Cys Ala Ala Ser Gly Phe Thr Phe Asp Asp Tyr
20 25 30

Gly Met Ser Trp Val Arg Gln Ala Pro Gly Lys Gly Leu Glu Trp Val
35 40 45

Ser Gly Ile Ser Trp Asn Gly Gly Ile Thr Val Tyr Ala Asp Ser Val
50 55 60

Lys Gly Arg Phe Thr Val Ser Arg Asp Asn Ala Lys Asn Ser Leu Tyr
65 70 75 80

Leu Gln Met Asn Ser Leu Arg Ala Glu Asp Thr Ala Leu Tyr His Cys
85 90 95

Ala Arg Ala Arg Tyr Gly Gly Ala Asp Tyr Trp Gly Gln Gly Thr Leu
100 105 110

Val Thr Val Ser Ser Ala Ser Thr Lys Gly Pro Ser Val Phe Pro Leu
115 120 125

Ala Pro Cys Ser Arg Ser Thr Ser Glu Ser Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Lys Thr Tyr Thr Cys Asn Val Asp His Lys Pro Ser Asn
195 200 205

Thr Lys Val Asp Lys Arg Val Glu Ser Lys Tyr Gly Pro Pro Cys Pro
210 215 220

Pro Cys Pro Ala Pro Glu Phe Leu Gly Gly Pro Ser Val Phe Leu Phe
225 230 235 240

Pro Pro Lys Pro Lys Asp Thr Leu Met Ile Ser Arg Thr Pro Glu Val
245 250 255

Thr Cys Val Val Val Asp Val Ser Gln Glu Asp Pro Glu Val Gln Phe
260 265 270

Asn Trp Tyr Val Asp Gly Val Glu Val His Asn Ala Lys Thr Lys Pro
275 280 285

Arg Glu Glu Gln Phe Asn Ser Thr Tyr Arg Val Val Ser Val Leu Thr
290 295 300

Val Leu His Gln Asp Trp Leu Asn Gly Lys Glu Tyr Lys Cys Lys Val
305 310 315 320

Ser Asn Lys Gly Leu Pro Ser Ser Ile Glu Lys Thr Ile Ser Lys Ala
325 330 335

Lys Gly Gln Pro Arg Glu Pro Gln Val Tyr Thr Leu Pro Pro Ser Gln
340 345 350

Glu Glu Met Thr Lys Asn Gln Val Ser Leu Thr Cys Leu Val Lys Gly
355 360 365

Phe Tyr Pro Ser Asp Ile Ala Val Glu Trp Glu Ser Asn Gly Gln Pro
370 375 380

Glu Asn Asn Tyr Lys Thr Thr Pro Pro Val Leu Asp Ser Asp Gly Ser
385 390 395 400

Phe Phe Leu Tyr Ser Arg Leu Thr Val Asp Lys Ser Arg Trp Gln Glu
405 410 415

Gly Asn Val Phe Ser Cys Ser Val Met His Glu Ala Leu His Asn His
420 425 430

Tyr Thr Gln Lys Ser Leu Ser Leu Ser Leu Gly Lys
        435                 440

<210> SEQ ID NO 26
<211> LENGTH: 215
<212> TYPE: PRT
<213> ORGANISM: Homo sapiens

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 27
<211> LENGTH: 447
<212> TYPE: PRT
<213> ORGANISM: Homo sapiens

<400> SEQUENCE: 27

Glu Val Gln Val Leu Glu Ser Gly Gly Asp Leu Val Gln Pro Gly Gly
1               5                   10                  15

Ser Leu Arg Leu Ser Cys Ala Ala Ser Gly Phe Thr Phe Ser Ala Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Gly Ser Ala Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Asp Gly Ala Trp Lys Met Ser Gly Leu Asp Val Trp Gly Gln
100 105 110

Gly Thr Thr Val Ile Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Phe Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser Gln Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Gly Leu Pro Ser Ser Ile Glu Lys Thr Ile
325 330 335

Ser Lys Ala Lys Gly Gln Pro Arg Glu Pro Gln Val Tyr Thr Leu Pro
340 345 350

Pro Ser Gln Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Arg Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Leu Gly Lys
435 440 445

<210> SEQ ID NO 28
<211> LENGTH: 214
<212> TYPE: PRT
<213> ORGANISM: Homo sapiens

<400> SEQUENCE: 28

Asp Ile Gln Met Thr Gln Ser Pro Ala Ser Leu Ser Ala Ser Val Gly
1 5 10 15

Asp Arg Val Thr Ile Thr Cys Arg Ala Ser Gln Asp Ile Ser Asp Tyr

```
            20                  25                  30

Leu Ala Trp Tyr Gln Gln Lys Pro Gly Lys Ile Pro Arg Leu Leu Ile
        35                  40                  45

Tyr Thr Thr Ser Thr Leu Gln Ser Gly Val Pro Ser Arg Phe Arg Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asp Ser Ala Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 29
<211> LENGTH: 453
<212> TYPE: PRT
<213> ORGANISM: Homo sapiens

<400> SEQUENCE: 29

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Ser His
            20                  25                  30

Phe Trp Ser Trp Ile Arg Gln Pro Pro Gly Lys Gly Leu Glu Trp Ile
        35                  40                  45

Gly Tyr Ile Leu Tyr Thr Gly Gly Thr Ser Phe Asn Pro Ser Leu Lys
    50                  55                  60

Ser Arg Val Ser Met Ser Val Gly Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Ser Gly Ile Thr Phe Thr Gly Ile Ile Val Pro Gly Ser
            100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175
```

```
His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly Lys
    450


<210> SEQ ID NO 30
<211> LENGTH: 215
<212> TYPE: PRT
<213> ORGANISM: Homo sapiens

<400> SEQUENCE: 30

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

-continued

```
Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

COMPOSITIONS AND METHODS FOR ENHANCING BODY WEIGHT AND LEAN MUSCLE MASS USING ANTAGONISTS AGAINST LEPTIN RECEPTOR, GDF8 AND ACTIVIN A

CROSS-REFERENCE TO RELATED APPLICATIONS

This application is a National Stage Application of PCT/US2019/066908, filed Dec. 17, 2019, which claims the benefit under 35 USC § 119(e) of U.S. Provisional Application No. 62/781,226, filed Dec. 18, 2018 each of which are incorporated herein by reference. To the extent appropriate, a claim of priority is made to each of the above-disclosed applications.

FIELD OF THE INVENTION

The present invention provides, in part, compositions, including inhibitors of LEPR, GDF8 and Activin A, and methods of treatment for enhancing body weight and lean muscle mass.

SEQUENCE LISTING

An official copy of the sequence listing is submitted concurrently with the specification electronically via EFS-Web as an ASCII formatted sequence listing with a file name of "10547WOseqlist_ST25.txt", a creation date of Dec. 17, 2019, and a size of about 26 KB. The sequence listing contained in this ASCII formatted document is part of the specification and is herein incorporated by reference in its entirety.

BACKGROUND OF THE INVENTION

Growth and differentiation factor-8 (GDF8, also known as myostatin) and Activin A are two important regulators of the development and maintenance of skeletal muscle and muscle mass.

GDF8 is a secreted ligand belonging to the transforming growth factor-β (TGF-β) superfamily of growth factors that acts as a negative regulator of muscle mass. GDF8 antagonists have been used in adult mice with significant positive effects on skeletal muscle mass. A receptor to which GDF8 binds and negatively regulates muscle mass is the activin receptor type IIB (ACVR2B). GDF8 is not the only negative regulator of muscle mass acting via ACVR2B. Activin A (ActA) also negatively regulates muscle mass via this receptor (Latres et al., Activin A more prominently regulates muscle mass in primates than does GDF8, Nature Comm. 8:15153 (2017)). ActRIIB binds ligands including Activin A, B, C and E, GDF11, bone morphogenetic protein 9 (BMP9) and BMP10. Data suggest that Activin A acts in concert with GDF8 to regulate skeletal muscle mass and that combined GDF8 and Activin A inhibition may be effective for the treatment of muscle atrophy in patients with wasting disorders of muscle (Latres et al. (2017)).

Leptin is a polypeptide hormone predominantly expressed by adipose tissue and skeletal muscle and is involved in the regulation of metabolism, energy balance and food intake. Leptin activity is mediated by interaction with, and signaling through, the leptin receptor. Leptin receptor, (also known as "LEPR," "WSX," "OB receptor," "OB-R," and "CD295") is a single-pass transmembrane receptor of the class I cytokine receptor family with a large extracellular domain. LEPR regulates body weight via JAK-STAT3 signaling. Altered signaling from leptin or LEPR or both can contribute to multiple disorders including, but not limited to, anorexia or other psychiatric eating disorders, cachexia, autoimmune disorders, cardiovascular diseases and neurodegenerative disorders.

SUMMARY OF THE INVENTION

The present invention relates to compositions that are useful not only for increasing overall body mass, but also for increasing body mass in a manner which leads to a more desirable overall body composition. As mentioned, administration of antagonistic anti-LEPR, anti-GDF8 and anti-ActA antibodies (triple combination) led to an increase in overall body weight over what was observed with anti-LEPR alone or anti-GDF8 with anti-ActA. Further beneficial effects were observed with respect to the lean mass of subjects who received the triple combination. The overall lean mass increased and the proportion of fat mass-to-lean decreased in these subjects (relative to anti-LEPR alone or anti-GDF8 with anti-ActA). For example, this increase in lean mass was confirmed insofar as subjects receiving the triple combination exhibited greater muscle mass and muscle fiber size (area) in some specific muscle structures assayed.

The present invention provides a combination comprising: a leptin receptor (e.g., human leptin receptor) antagonist in association with a GDF8 (e.g., human GDF8) antagonist in association with an Activin A (e.g., human Activin A) antagonist (e.g., H4H18457P2/H4H1657N2/H4H10446P2); and optionally, a pharmaceutically acceptable carrier. For example, such combinations may include a co-formulation including at least two antagonists selected from leptin receptor antagonist, GDF8 antagonist and Activin A antagonist; or the antagonists can be in separate compositions. The leptin receptor antagonist, GDF8 antagonist and/or Activin A antagonist is, in an embodiment of the invention, an antibody or antigen-binding fragment thereof that binds specifically to leptin receptor, GDF8 and/or Activin A, respectively. In an embodiment of the invention, the leptin receptor antagonist is an antibody or antigen-binding fragment which specifically binds to the receptor and does not compete with leptin for binding to the receptor. In an embodiment of the invention, the LEPR antagonist is an antibody or an antigen-binding fragment thereof that specifically binds to LEPR comprises a heavy chain variable region that comprises CDR-H1, CDR-H2, CDR-H3 of a heavy chain variable region selected from H4H17322P2, H4H18437P2, H4H18439P2, H4H18440P2, H4H18457P2, H4H18462P2, H4H18464P2, H4H18466P2 and H4H18508P2; and CDR-L1, CDR-L2, CDR-L3 of a light chain variable region selected from H4H17322P2, H4H18437P2, H4H18439P2, H4H18440P2, H4H18457P2, H4H18462P2, H4H18464P2, H4H18466P2 and H4H18508P2, or that binds to the same epitope on LEPR as said antibody or fragment and/or that competes for binding to LEPR as said antibody or fragment. In an embodiment of the invention, the GDF8 antagonist is an antibody or an antigen-binding fragment thereof that specifically binds to GDF8 that comprises a heavy chain variable region that comprises CDR-H1, CDR-H2, CDR-H3 of a heavy chain variable region selected from 21-E5; 21-B9; 21-E9; 21-A2; 22-D3; 22-E6; 22-G10; 1A2; 20B12; 58C8; 19F2; 8D12-1; 4E3-7; 9B11-12; 4B9; 1H4-5; 9B4-3; 3E2-1; 4G3-25; 4B6-6; H4H1657N2 or H4H1669P and H4H18508P2; and CDR-L1, CDR-L2, CDR-L3 of a light chain variable region selected from 21-E5; 21-B9; 21-E9;

21-A2; 22-D3; 22-E6; 22-G10; 1A2; 20B12; 58C8; 19F2; 8D12-1; 4E3-7; 9B11-12; 4B9; 1114-5; 9B4-3; 3E2-1; 4G3-25; 4B6-6; H4H1657N2 or H4H1669P and H4H18508P2, or that binds to the same epitope on GDF8 as said antibody or fragment and/or that competes for binding to GDF8 as said antibody or fragment. In an embodiment of the invention, the Activin A antagonist is an antibody or an antigen-binding fragment thereof that specifically binds to Activin A that comprises a heavy chain variable region that comprises CDR-H1, CDR-H2, CDR-H3 of a heavy chain variable region selected from H4H10423P, H4H10424P, H4H10426P, H4H10429P, H4H10430P, H4H10432P2, H4H10433P2, H4H10436P2, 1141110437P2, H4H10438P2, H4H10440P2, H4H10442P2, H4H10445P2, H4H10446P2, H4H10447P2, H4H10448P2, H4H10452P2, H4H10468P2 and H2aM10965N and CDR-L1, CDR-L2, CDR-L3 of a light chain variable region selected from H4H10423P, H4H10424P, H4H10426P, H4H10429P, H4H10430P, H4H10432P2, H4H10433P2, H4H10436P2, H4H10437P2, H4H10438P2, H4H10440P2, H4H10442P2, H4H10445P2, H4H10446P2, H4H10447P2, H4H10448P2, H4H10452P2, H4H10468P2 and H2aM10965N, or that binds to the same epitope on Activin A as said antibody or fragment and/or that competes for binding to Activin A as said antibody or fragment. In an embodiment of the invention, the LEPR antagonist is an antibody or an antigen-binding fragment thereof that comprises a heavy chain variable region selected from H4H17322P2, H4H18437P2, H4H18439P2, H4H18440P2, H4H18457P2, H4H18462P2, H4H18464P2, H4H18466P2 and H4H18508P2; and a light chain variable region selected from H4H17322P2, H4H18437P2, H4H18439P2, H4H18440P2, H4H18457P2, H4H18462P2, H4H18464P2, H4H18466P2 and H4H18508P2, or that binds to the same epitope on LEPR as said antibody or fragment and/or that competes for binding to LEPR as said antibody or fragment. In an embodiment of the invention, the GDF8 antagonist is an antibody or an antigen-binding fragment thereof that comprises a heavy chain variable region selected from 21-E5; 21-B9; 21-E9; 21-A2; 22-D3; 22-E6; 22-G10; 1A2; 20B12; 58C8; 19F2; 8D12-1; 4E3-7; 9B11-12; 4B9; 1114-5; 9B4-3; 3E2-1; 4G3-25; 4B6-6; H4H1657N2 or H4H1669P and H4H18508P2; and a light chain variable region selected from 21-E5; 21-B9; 21-E9; 21-A2; 22-D3; 22-E6; 22-G10; 1A2; 20B12; 58C8; 19F2; 8D12-1; 4E3-7; 9B11-12; 4B9; 1114-5; 9B4-3; 3E2-1; 4G3-25; 4B6-6; H4H1657N2 or H4H1669P and H4H18508P2 or that binds to the same epitope on GDF8 as said antibody or fragment and/or that competes for binding to GDF8 as said antibody or fragment. In an embodiment of the invention, the Activin A antagonist is an antibody or an antigen-binding fragment thereof that comprises a heavy chain variable region selected from H4H10423P, H4H10424P, H4H10426P, H4H10429P, H4H10430P, H4H10432P2, H4H10433P2, H4H10436P2, H4H10437P2, H4H10438P2, H4H10440P2, H4H10442P2, H4H10445P2, H4H10446P2, H4H10447P2, H4H10448P2, H4H10452P2, H4H10468P2 and H2aM10965N; and a light chain variable region selected from H4H10423P, H4H10424P, H4H10426P, H4H10429P, H4H10430P, H4H10432P2, H4H10433P2, H4H10436P2, H4H10437P2, H4H10438P2, H4H10440P2, H4H10442P2, H4H10445P2, H4H10446P2, H4H10447P2, H4H10448P2, H4H10452P2, H4H10468P2 and H2aM10965N, or that binds to the same epitope on Activin A as said antibody or fragment and/or that competes for binding to Activin A as said antibody or fragment. Such combinations optionally include one or more further therapeutic agents (e.g., an appetite stimulant, a cannabinoid, an angiotensin-converting enzyme (ACE) inhibitor, an angiotensin receptor blocker, a smooth muscle relaxant, a nitrate, a diuretic, iron, a bronchodilator, an anticholinergic, a corticosteroid, an antibiotic, a nonsteroidal anti-inflammatory drug (NSAID), an immunosuppressant, an HMG-CoA reductase inhibitor, an anti-depressant, an anti-cancer therapy and/or a topical agent).

The present invention provides an injection device (e.g., hypodermic needle and syringe, an autoinjector or a pre-filled syringe) or vessel (e.g., a vial) that includes a combination of the present invention (e.g., H4H18457P2/H4H1657N2/H4H10446P2). The present invention further provides methods for administering the combination of the present invention to a subject (e.g., a human) including the step of introducing the components of the combination into the body of the subject, e.g., parenterally, for example, by injection using an injection device according to the present invention. In an embodiment of the invention, the subject suffers from malnutrition, failure to thrive, insufficient food intake, an eating disorder, cachexia, muscle atrophy or wasting and muscle injury and/or is undergoing physical therapy.

The present invention also provides a method for inhibiting LEPR, GDF8 and Activin A in the body of a subject (e.g., a human) comprising administering a therapeutically effective amount of the combination of the present invention (e.g., H4H18457P2/H4H1657N2/H4H10446P2) to the subject e.g., parenterally, for example, by injection using an injection device according to the present invention. In an embodiment of the invention, the subject suffers from malnutrition, failure to thrive, insufficient food intake, an eating disorder, cachexia, muscle atrophy or wasting and muscle injury and/or is undergoing physical therapy.

The present invention also provides a method for increasing food intake, adiposity, body weight, muscle strength, muscle fiber size or lean mass (e.g., at the expense of fat mass), in a subject in need thereof, comprising administering a therapeutically effective amount of the combination of the present invention (e.g., H4H18457P2/H4H1657N2/H4H10446P2) to the subject (e.g., a human). In an embodiment of the invention, the subject suffers from malnutrition, failure to thrive, insufficient food intake, an eating disorder, cachexia, muscle atrophy or wasting and muscle injury and/or is undergoing physical therapy.

The present invention further provides a method for increasing athletic performance in a subject in need thereof (e.g., a human) comprising administering a therapeutically effective amount of the combination of the present invention (e.g., H4H18457P2/H4H1657N2/H4H10446P2) to the subject. In an embodiment of the invention, the subject suffers from malnutrition, failure to thrive, insufficient food intake, an eating disorder, cachexia, muscle atrophy or wasting and muscle injury and/or is undergoing physical therapy (e.g., stroke rehabilitation).

The present invention provides a method for mitigating increased liver triglyceride content in a subject administered an leptin receptor antagonist comprising administering, to the subject, in association with the leptin receptor antagonist, a GDF8 antagonist in association with an Activin A antagonist (e.g., H4H18457P2/H4H1657N2/H4H10446P2).

The present invention also provides a method for treating or preventing malnutrition, cachexia, failure to thrive, an eating disorder characterized by inadequate caloric intake, muscle atrophy, age-related sarcopenia or muscle injury in a subject (e.g., a human) in need thereof comprising administering a therapeutically effective amount of combination of the present invention (e.g., H4H18457P2/H4H1657N2/

H4H10446P2) to the subject. For example, in an embodiment of the invention, (i) the subject with malnutrition suffers from hospital malnutrition, failure to thrive in childhood, an eating disorder characterized by inadequate caloric intake, anorexia and/or bulimia; (ii) the subject with cachexia suffers from or is undergoing anorexia bulimia, an eating disorder, a pulmonary disease, chronic obstructive pulmonary disorder (COPD), chronic kidney disease, infectious disease, HIV-infection, acquired immune deficiency syndrome (AIDS), congestive heart failure, radiation treatment, cancer, hepatocellular carcinoma, melanoma, breast cancer, an autoimmune disorder, inflammatory bowel disease, lupus erythematosus, multiple sclerosis, rheumatoid arthritis, Crohn's disease, psoriasis, cystic fibrosis, cardiovascular disease, elevated blood pressure, depression and/or neurodegenerative disorders; and/or (iii) the subject with muscle atrophy or wasting suffers from or is experiencing sepsis, AIDS, renal failure, cardiac failure, excessive glucocorticoids, Cushing syndrome, trauma, muscular disuse, immobilization, bed rest, injury, hip fracture, hip replacement, knee replacement and/or mechanical ventilation.

Methods for making a combination of the present invention (e.g., H4H18457P2/H4H1657N2/H4H10446P2) comprising co-formulating the LEPR antagonist, the GDF8 antagonist and the Activin A antagonist and a pharmaceutically acceptable carrier are also part of the present invention.

The present invention also provides a method of making the device or vessel that comprises a combination of the present invention (e.g., H4H18457P2/H4H1657N2/H4H10446P2) comprising introducing the components of the combination into the vessel or device.

DETAILED DESCRIPTION OF THE INVENTION

"LEPR/GDF8/ActA" combinations of the present invention include compositions or kits, e.g., pharmaceutical compositions comprising a pharmaceutically acceptable carrier, and one or more LEPR antagonists, one or more GDF8 antagonists and one or more activin A antagonists in association with one another and, optionally, in association with one or more further therapeutic agents. In an embodiment of the invention, the LEPR/GDF8/ActA combination comprises the anti-LEPR antibody H4H18457P2 or an antigen-binding fragment thereof (or a variant thereof), the anti-GDF8 antibody H4H1657N2 or an antigen-binding fragment thereof (or a variant thereof) and the anti-ActA antibody H4H10446P2 or an antigen-binding fragment thereof (or a variant thereof) (H4H18457P2/H4H1657N2/H4H10446P2).

The term "in association with" indicates that the components of the LEPR/GDF8/ActA combinations of the present invention (e.g., H4H18457P2/H4H1657N2/H4H10446P2) are collocated. For example, the LEPR antagonist, the GDF8 antagonist and the Activin A antagonist can be formulated into a single composition, e.g., for simultaneous delivery, or formulated separately into two or more compositions (e.g., and included in a kit). The combination, for example, may be a first composition having the LEPR antagonist co-formulated with the GDF8 antagonist collocated with a second composition which has a separately formulated Activin A antagonist. Alternatively, the combination may be three separately formulated compositions—a first LEPR antagonist composition, a second GDF8 antagonist composition and a third Activin A antagonist composition. Each component of the combination, when formulated separately, can be administered to a subject at a different time than when the other component is administered; for example, each administration may be given non-simultaneously (e.g., separately or sequentially) at intervals over a given period of time in a treatment regimen. Moreover, the separate components may be administered to a subject by the same or by a different route.

Anti-LEPR, anti-GDF8 and/or anti-ActA antibodies or antigen-binding fragments thereof, whose sequences appear in prior publications, are referred to herein. In an embodiment of the invention, such antibodies or fragments comprise at least one heavy chain variable domain ($V_H$) and/or at least one light chain variable region ($V_L$) whose sequence is referred to herein except that each may independently have 1, 2, 3, 4, 5, 6, 7, 8, 9 or 10 point mutations and/or point deletions. Anti-LEPR, anti-GDF8 and/or anti-ActA antibodies or fragments may include the heavy chain CDRs of $V_H$s (HCDRs) whose sequences are referred to herein except that each may independently have 1, 2, 3, 4, 5, 6, 7, 8, 9 or 10 point mutations and/or point deletions; and/or anti-LEPR, anti-GDF8 and/or anti-ActA antibodies or fragments may include the light chain CDRs of $V_L$s (HCDRs) whose sequences are referred to herein except that each may independently have 1, 2, 3, 4, 5, 6, 7, 8, 9 or 10 point mutations and/or point deletions. Antibodies or fragments including such mutations may be referred to herein as "variants". A "variant" of a polypeptide (e.g., $V_L$, $V_H$, HCDRs or LCDRs) may comprise a sequence having at least about 70-99.9% (e.g., 70, 72, 74, 75, 76, 79, 80, 81, 82, 83, 84, 85, 86, 87, 88, 89, 90, 91, 92, 93, 94, 95, 96, 97, 98, 99, 99.5, 99.9%) identity or similarity to a referenced sequence; for example when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment).

Sequence identity refers to the degree to which the amino acids of two polypeptides are the same at equivalent positions when the two sequences are optimally aligned. Sequence similarity includes identical residues and nonidentical, biochemically related amino acids. Biochemically related amino acids that share similar properties and may be interchangeable are discussed above.

A leptin receptor (LEPR, OB receptor, OB-R, CD295 or WSX) is, in an embodiment of the invention, the human leptin receptor, comprising the amino acid sequence as set forth in UniProtKB/Swiss-Prot Accession No. P48357.

GDF8 (growth and differentiation factor-8, MSTN or myostatin) includes a protein having the amino acid sequence set forth under UniProtKB/Swiss-Prot accession no. 014793.

Activins are homo- and hetero-dimeric molecules comprising beta subunits, i.e., Inhibin βA, inhibin βB, inhibin βθ, and/or inhibin βE. Activin A is a homodimer of two βA subunits; Activin B is a homodimer of two βB subunits; Activin AB is a heterodimer of one βA subunit and one βB subunit; and Activin AC is a heterodimer of one βA subunit and one βθ subunit. In an embodiment of the invention, the inhibin beta A chain amino acid sequence is set forth in under UniProtKB/Swiss-Prot accession no. P08476.

Lean mass is, in an embodiment of the invention, as determined using micro-computed tomography (μCT) or dual-energy X-ray absorptiometry (DXA).

General Methods

Standard methods in molecular biology are described Sambrook, Fritsch and Maniatis (1982 & 1989 2nd Edition, 2001 3rd Edition) Molecular Cloning, A Laboratory Manual, Cold Spring Harbor Laboratory Press, Cold Spring Harbor, N.Y.; Sambrook and Russell (2001) Molecular Cloning, 3.sup.rd ed., Cold Spring Harbor Laboratory Press, Cold Spring Harbor, N.Y.; Wu (1993) Recombinant DNA, Vol. 217, Academic Press, San Diego, Calif.). Standard methods also appear in Ausbel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) Current Protocols in Protein Science, Vol. 1, John Wiley and Sons, Inc., New York). Chemical analysis, chemical modification, post-translational modification, production of fusion proteins, glycosylation of proteins are described (see, e.g., Coligan, et al. (2000) Current Protocols in Protein Science, Vol. 2, John Wiley and Sons, Inc., New York; Ausubel, et al. (2001) Current Protocols in Molecular Biology, Vol. 3, John Wiley and Sons, Inc., NY, NY, pp. 16.0.5-16.22.17; Sigma-Aldrich, Co. (2001) Products for Life Science Research, St. Louis, Mo.; pp. 45-89; Amersham Pharmacia Biotech (2001) BioDirectory, Piscataway, N.J., pp. 384-391). Production, purification, and fragmentation of polyclonal and monoclonal antibodies are described (Coligan, et al. (2001) Current Protocols in Immunology, Vol. 1, John Wiley and Sons, Inc., New York; Harlow and Lane (1999) Using Antibodies, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) Current Protocols in Immunology, Vol. 4, John Wiley, Inc., New York).

Monoclonal, polyclonal, and humanized antibodies can be prepared (see, e.g., Sheperd and Dean (eds.) (2000) Monoclonal Antibodies, Oxford Univ. Press, New York, N.Y.; Kontermann and Dubel (eds.) (2001) Antibody Engineering, Springer-Verlag, New York; Harlow and Lane (1988) Antibodies A Laboratory Manual, Cold Spring Harbor Laboratory Press, Cold Spring Harbor, N.Y., pp. 139-243; Carpenter, et al. (2000) J. Immunol. 165:6205; He, et al. (1998) J. Immunol. 160:1029; Tang et al. (1999) J. Biol. Chem. 274:27371-27378; Baca et al. (1997) J. Biol. Chem. 272:10678-10684; Chothia et al. (1989) Nature 342:877-883; Foote and Winter (1992) J. Mol. Biol. 224:487-499; U.S. Pat. No. 6,329,511).

An alternative to humanization is to use human antibody libraries displayed on phage or human antibody libraries in transgenic mice (Vaughan et al. (1996) Nature Biotechnol. 14:309-314; Barbas (1995) Nature Medicine 1:837-839; Mendez et al. (1997) Nature Genetics 15:146-156; Hoogenboom and Chames (2000) Immunol. Today 21:371-377; Barbas et al. (2001) Phage Display: A Laboratory Manual, Cold Spring Harbor Laboratory Press, Cold Spring Harbor, N.Y.; Kay et al. (1996) Phage Display of Peptides and Proteins: A Laboratory Manual, Academic Press, San Diego, Calif.; de Bruin et al. (1999) Nature Biotechnol. 17:397-399). Single chain antibodies and diabodies are described (see, e.g., Malecki et al. (2002) Proc. Natl. Acad. Sci. USA 99:213-218; Conrath et al. (2001) J. Biol. Chem. 276:7346-7350; Desmyter et al. (2001) J. Biol. Chem. 276:26285-26290; Hudson and Kortt (1999) J. Immunol. Methods 231:177-189; and U.S. Pat. No. 4,946,778). Bifunctional antibodies are provided (see, e.g., Mack, et al. (1995) Proc. Natl. Acad. Sci. USA 92:7021-7025; Carter (2001) J. Immunol. Methods 248:7-15; Volkel, et al. (2001) Protein Engineering 14:815-823; Segal, et al. (2001) J. Immunol. Methods 248:1-6; Brennan, et al. (1985) Science 229:81-83; Raso, et al. (1997) J. Biol. Chem. 272:27623; Morrison (1985) Science 229:1202-1207; Traunecker, et al. (1991) EMBO J. 10:3655-3659; and U.S. Pat. Nos. 5,932,448, 5,532,210, and 6,129,914). Fully human antibodies may also be developed in genetically engineered mice such as the VelociMouse. See e.g., DeChiara et al., Producing fully ES cell-derived mice from eight-cell stage embryo injections, Methods Enzymol, 476:285-94 (2010); Dechiara et al., VelociMouse: fully ES cell-derived FO-generation mice obtained from the injection of ES cells into eight-cell-stage embryos. Methods Mol Biol, 530:311-24 (2009); U.S. Pat. Nos. 7,576,259; 7,659,442; or 7294754, and US2008/0078000A1.

Purification of antigen is not typically necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) Immunity 7:283-290; Wright et al. (2000) Immunity 13:233-242; Preston et al., supra; Kaithamana et al. (1999) J. Immunol. 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) J. Immunol. 146:169-175; Gibellini et al. (1998) J. Immunol. 160:3891-3898; Hsing and Bishop (1999) J. Immunol. 162:2804-2811; Everts et al. (2002) J. Immunol. 168:883-889).

Methods for flow cytometry, including fluorescence activated cell sorting (FACS), are available (see, e.g., Owens, et al. (1994) Flow Cytometry Principles for Clinical Laboratory Practice, John Wiley and Sons, Hoboken, N.J.; Givan (2001) Flow Cytometry, 2.sup.nd ed.; Wiley-Liss, Hoboken, N.J.; Shapiro (2003) Practical Flow Cytometry, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) Catalogue, Molecular Probes, Inc., Eugene, Oreg.; Sigma-Aldrich (2003) Catalogue, St. Louis, Mo.).

Standard methods of histology of the immune system are described (see, e.g., Muller-Harmelink (ed.) (1986) Human Thymus: Histopathology and Pathology, Springer Verlag, New York, N.Y.; Hiatt, et al. (2000) Color Atlas of Histology, Lippincott, Williams, and Wilkins, Phila, Pa.; Louis, et al. (2002) Basic Histology: Text and Atlas, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) Bioinformatics 16: 741-742; Menne, et al. (2000) Bioinformatics Applications Note 16:741-742; Wren, et al. (2002) Comput.

Methods Programs Biomed. 68:177-181; von Heijne (1983) Eur. J. Biochem. 133:17-21; von Heijne (1986) Nucleic Acids Res. 14:4683-4690).

Leptin Receptor Antagonists

The present invention includes LEPR/GDF8/ActA combinations (e.g., H4H18457P2/H4H1657N2/H4H10446P2) which include one or more LEPR antagonists. In an embodiment of the invention, a LEPR antagonist is an anti-LEPR antibody or antigen-binding fragment thereof that does not compete with leptin for binding to LEPR.

LEPR antagonists include antibodies and antigen-binding fragments thereof and other substances (e.g., peptides and small molecules) that specifically bind to LEPR and antagonize one or more biological activities of LEPR. Molecules that specifically bind to LEPR may be referred to as "anti-LEPR". In an embodiment of the invention, a LEPR antagonist inhibits LEPR signaling, e.g., by binding human LEPR and antagonizing activation of the LEPR-dependent intracellular signaling cascade. Antagonism of LEPR may, in an embodiment of the invention, be achieved by blocking LEPR/leptin binding, e.g., by formation of a complex between the antagonist and leptin or LEPR or both. LEPR signaling antagonism includes, for example, reduction of LEPR-dependent transcriptional activation of STAT3. See e.g., Villanueva & Myers, Int. J. Obes. 32(Suppl 7): S8-12 (2008) and Park & Ahima, F1000Prime Reports 6:73 (2014).

In an embodiment of the invention, a LEPR antagonist is a mutant version of leptin, e.g., a PEGylated mutant leptin. For example, in an embodiment of the invention, the LEPR antagonist is a mammalian (e.g., human) leptin polypeptide in which the LDFI hydrophobic binding site is modified such that from two to four amino acid residues of said hydrophobic binding site are substituted with different amino acid residues such that the site becomes less hydrophobic, said modified, mammalian leptin polypeptide being a leptin antagonist; or a fragment of said modified mammalian leptin polypeptide comprising said altered hydrophobic binding site, wherein said fragment is itself a leptin antagonist. For example, wherein two or more amino acids of the LDFI motif are substituted with alanine, arginine, aspartic acid, glutamic acid, glycine, lysine or serine, e.g., having the mutations L39A/D40A/F41A/142A. Such a leptin mutant may be PEGylated, e.g., with one or more 4000-6000 dalton PEG molecules. See U.S. Pat. No. 7,307,142.

In an embodiment of the invention, the LEPR antagonist is an antibody or antigen-binding fragment selected from H4H17322P2, H4H18437P2, H4H18439P2, H4H18440P2, H4H18457P2, H4H18462P2, H4H18464P2, H4H18466P2 and H4H18508P2; or any other antibody or antigen-binding fragment set forth in WO2018/089532.

In an embodiment of the invention, the anti-LEPR antibody is H4H18457P2.

In an embodiment of the invention, the anti-LEPR antibody or fragment of the present invention comprises:

(i) the HCDRs (HCDR1, HCDR2 and HCDR3) of a heavy chain variable region (or having variants of one or more of the HCDRs) and/or the LCDRs (LCDR1, LCDR2 and LCDR3) of a light chain variable region (or having variants of one or more of the LCDRs) of an antibody selected from H4H17322P2, H4H18437P2, H4H18439P2, H4H18440P2, H4H18457P2, H4H18462P2, H4H18464P2, H4H18466P2 and H4H18508P2; and/or (ii) the heavy chain variable region (or a variant thereof) and/or the light chain variable region (or a variant thereof) of an antibody selected from H4H17322P2, H4H18437P2, H4H18439P2, H4H18440P2, H4H18457P2, H4H18462P2, H4H18464P2, H4H18466P2 and H4H18508P2;

and/or is characterized as:

(iii) competing for binding to LEPR (e.g., LEPR with a C-terminal myc-myc-$His_6$ tag) with H4H17322P2, H4H18437P2, H4H18439P2, H4H18440P2, H4H18457P2, H4H18462P2, H4H18464P2, H4H18466P2 and/or H4H18508P2;

and/or (iv) binding to LEPR at the same epitope as H4H17322P2, H4H18437P2, H4H18439P2, H4H18440P2, H4H18457P2, H4H18462P2, H4H18464P2, H4H18466P2 and/or H4H18508P2, e.g., wherein the epitope is the extracellular domain of LEPR, the LEPR CRH (cytokine receptor homology) domain 2, the CRH2 domain, the FNIII (fibronectin type III) domain or the Ig(D3) domain.

See international patent application publication no. WO2018/89532.

In an embodiment of the invention, such an antibody or fragment comprises a heavy chain constant domain selected from IgG1, IgG2, IgG3 and IgG4 and/or a light chain constant domain selected from kappa and lambda.

In an embodiment of the invention, the LEPR antagonist is the antibody H4H18457P2 or an antigen-binding fragment thereof.

In an embodiment of the invention the LEPR antagonist is an antibody or antigen-binding fragment thereof comprising:

(1)
a $V_H$ comprising the amino acid sequence:
(SEQ ID NO: 1; or a variant thereof)
EVQLVESGGSVVRPGESLRLSCAASGFTFDDYGMSWVRQAPGKGLEWVSG

ISWNGGITVYADSVKGRFTVSRDNAKNSLYLQMNSLRAEDTALYHCARAR

YGGADYWGQGTLVTVSS
and/or a $V_L$ comprising the amino acid sequence:
(SEQ ID NO: 2; or a variant thereof)
DIQMTQSPSSLSASVGDRVTITCRASQSISSYLNWYQQKPOKAPKLLIY

AASSLQSGVPSRFSGSGSGTDFTLTISSLQPEDFATYYCQQSYSTPPIT

FGQGTRLEIK;
and/or (2)
a $V_L$ comprising the CDR-Ls thereof, e.g.,:
CDR-L1 comprising the amino acid sequence:
(SEQ ID NO: 3; or a variant thereof)
Gln Ser Ile Ser Ser Tyr;

CDR-L2 comprising the amino acid sequence:
(SEQ ID NO: 4; or a variant thereof)
Ala Ala Ser;
and CDR-L3 comprising the amino acid sequence:
(SEQ ID NO: 5; or a variant thereof)
Gln Gln Ser Tyr Ser Thr Pro Pro Ile Thr;
and/or a $V_H$ comprising the CDR-Hs thereof, e.g.,:
CDR-H1 comprising the amino acid sequence:
(SEQ ID NO: 6; or a variant thereof)
Gly Phe Thr Phe Asp Asp Tyr Gly;

-continued

```
CDR-H2 comprising the amino acid sequence:
                    (SEQ ID NO: 7; or a variant thereof)
Ile Ser Trp Asn Gly Gly Ile Thr;
and

CDR-H3 comprising the amino acid sequence:
                    (SEQ ID NO: 8; or a variant thereof)
Ala Arg Ala Arg Tyr Gly Gly Ala Asp Tyr;
and/or

(3)
a heavy chain immunoglobulin comprising the amino
acid sequence:
                                      (SEQ ID NO: 25)
EVQLVESGGSVVRPGESLRLSCAASGFTFDDYGMSWVRQAPGKGLEWVSG

ISWNGGITVYADSVKGRFTVSRDNAKNSLYLQMNSLRAEDTALYHCARAR

YGGADYWGQGTLVTVSSASTKGPSVFPLAPCSRSTSESTAALGCLVKDYF

PEPVTVSWNSGALTSGVHTFPAVLQSSGLYSLSSVVTVPSSSLGTKTYTC

NVDHKPSNTKVDKRVESKYGPPCPPCPAPEFLGGPSVFLEPPKPKDTLMI

SRTPEVTCVVVDVSQEDPEVQFNWYVDGVEVHNAKTKPREEQFNSTYRVV

SVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGS

FFLYSRLTVDKSRWQEGNVESCSVMHEALHNHYTQKSLSLSLGK (or a

variant thereof)
and

a light chain immunoglobulin comprising the amino
acid sequence:
                                      (SEQ ID NO: 26)
DIQMTQSPSSLSASVGDRVTITCRASQSISSYLNWYQQKPOKAPKLLIYA

ASSLQSGVPSRFSGSGSGTDFTLTISSLQPEDFATYYCQQSYSTPPITEG

QGTRLEIKRTVAAPSVFIFPPSDEQLKSGTASVVCLLNNEYPREAKVQWK

VDNALQSGNSQESVTEQDSKDSTYSLSSTLTLSKADYEKHKVYACEVTHQ

GLSSPVTKSFNRGEC (or a variant thereof).
```

In an embodiment of the invention, such a $V_L$ is linked to a human kappa or lambda light chain immunoglobulin constant domain and/or such a $V_H$ is linked to a human IgG (e.g., IgG1, IgG2, IgG3 or IgG4 (for example, an S228P mutant IgG4)) heavy chain immunoglobulin constant domain.

GDF8 Antagonists

The present invention includes LEPR/GDF8/ActA combinations (e.g., H4H18457P2/H4H1657N2/H4H10446P2) which include one or more GDF8 antagonists.

GDF8 antagonists include antibodies and antigen-binding fragments thereof and other substances (e.g., peptides and small molecules) that specifically bind to GDF8 and antagonize one or more biological activities of GDF8. Molecules that specifically bind to GDF8 may be referred to as "anti-GDF8". For example, in an embodiment of the invention, the antagonist blocks interaction between GDF8 and Activin RIIB (or an Fc fusion thereof) or inhibits SMAD-dependent activation of A204 cells stably expressing Smad-dependent (CAGA12) luciferase.

In an embodiment of the invention, a GDF8 antagonist is a small molecule such as dorsomorphin (Millipore Sigma; St. Louis, Mo.) or LDN-193189 (Millipore Sigma; St. Louis, Mo.).

In an embodiment of the invention, a GDF8 antagonist specifically binds GDF8 but, for example, does not bind other ActRIIB ligands such as GDF3, BMP2, BMP4, BMP7, BMP9, BMP10, GDF11, Activin A, Activin B, Activin AB, and/or Nodal.

In an embodiment of the invention, the GDF8 antagonist is an anti-GDF8 antibody or antigen-binding fragment thereof. Anti-GDF8 antibodies are mentioned in, e.g., U.S. Pat. Nos. 6,096,506; 7,320,789; 7,261,893; 7,807,159; 7,888,486; 7,635,760; 7,632,499; in U.S. Patent Appl. Publ. Nos. 2007/0178095; 2010/0166764; and 2009/0148436; and International Patent Appl. Publ. No. WO2010/070094.

Anti-GDF8 antibodies are also described in U.S. patent application Ser. No. 13/115,170, filed on May 25, 2011, and published as US2011/0293630, now U.S. Pat. No. 8,840,894 or International Patent Application No. PCT/US2012/064911, filed Nov. 14, 2012 (WO2013/074557), including the antibodies designated 21-E5; 21-B9; 21-E9; 21-A2; 22-D3; 22-E6; 22-G10; 1A2; 20B12; 58C8; 19F2; 8D12-1 (or 8D12); 4E3-7; 9B11-12; 4B9; 1 H4-5; 9B4-3; 3E2-1; 4G3-25; 4B6-6; H4H1657N2 or H4H1669P or an antigen-binding fragment thereof.

In an embodiment of the invention, the GDF8 antagonist is an anti-GDF8 antibody or antigen-binding fragment selected from 21-E5; 21-B9; 21-E9; 21-A2; 22-D3; 22-E6; 22-G10; 1A2; 20B12; 58C8; 19F2; 8D12-1 (or 8D12); 4E3-7; 9B11-12; 4B9; 1H4-5; 9B4-3; 3E2-1; 4G3-25; 4B6-6; H4H1657N2 or H4H1669P; or any anti-GDF8 antibody or antigen-binding fragment set forth in US2011/0293630.

In an embodiment of the invention, the anti-GDF8 antibody is H4H1657N2.

In an embodiment of the invention, the anti-GDF8 antibody or fragment of the present invention comprises:

(i) the HCDRs (HCDR1, HCDR2 and HCDR3) of a heavy chain variable region (or having variants of one or more of the HCDRs) and/or the LCDRs (LCDR1, LCDR2 and LCDR3) of a light chain variable region (or having variants of one or more of the LCDRs) of an antibody selected from 21-E5; 21-B9; 21-E9; 21-A2; 22-D3; 22-E6; 22-G10; 1A2; 20B12; 58C8; 19F2; 8D12-1 (or 8D12); 4E3-7; 9B11-12; 4B9; 1H4-5; 9B4-3; 3E2-1; 4G3-25; 4B6-6; H4H1657N2 or H4H1669P; and/or (ii) the heavy chain variable region (or a variant thereof) and/or light chain variable region (or a variant thereof) of an antibody selected from 21-E5; 21-B9; 21-E9; 21-A2; 22-D3; 22-E6; 22-G10; 1A2; 20B12; 58C8; 19F2; 8D12-1 (or 8D12); 4E3-7; 9B11-12; 4B9; 1H4-5; 9B4-3; 3E2-1; 4G3-25; 4B6-6; H4H1657N2 or H4H1669P;

and/or is characterized as:

(iii) competing for binding to GDF8 with 21-E5; 21-B9; 21-E9; 21-A2; 22-D3; 22-E6; 22-G10; 1A2; 20B12; 58C8; 19F2; 8D12-1 (or 8D12); 4E3-7; 9B11-12; 4B9; 1H4-5; 9B4-3; 3E2-1; 4G3-25; 4B6-6; H4H1657N2 or H4H1669P;

and/or (iv) binding to GDF8 at the same epitope as 21-E5; 21-B9; 21-E9; 21-A2; 22-D3; 22-E6; 22-G10; 1A2; 20B12; 58C8; 19F2; 8D12-1 (or 8D12); 4E3-7; 9B11-12; 4B9; 1H4-5; 9B4-3; 3E2-1; 4G3-25; 4B6-6; H4H1657N2 or H4H1669P, e.g., wherein the epitope is GDF8 amino acids 1-14, 48-65, 48-69, 48-72, 52-65, 52-72, 56-65, 56-72 and/or 73-90; or a peptide consisting of such amino acids (e.g., comprising a C-terminal tag such as biotin).

See published US patent application no. US2011/0293630. In an embodiment of the invention, such an antibody or fragment comprises a heavy chain constant domain selected from IgG1, IgG2, IgG3 and IgG4 and/or a light chain constant domain selected from kappa and lambda.

Antibody H4H1657N2 may be referred to as REGN1033 or trevogrumab.

In an embodiment of the invention the GDF8 antagonist is an antibody or antigen-binding fragment thereof comprising:

(1)
a $V_H$ comprising the amino acid sequence:
(SEQ ID NO: 9; or a variant thereof)
EVQVLESGGDLVQPGGSLRLSCAASGFTFSAYAMTWVRQAPGKGLEWVSA

ISGSGGSAYYADSVKGRFTISRDNSKNTVYLQMNSLRAEDTAVYYCAKDG

AWKMSGLDVWGQGTTVIVSS;
and a $V_L$ comprising the amino acid sequence:
(SEQ ID NO: 10; or a variant thereof)
DIQMTQSPASLSASVGDRVTITCRASQDISDYLAWYQQKPOKIPRLLIY

TTSTLQSGVPSRFRGSGSGTDFTLTISSLQPEDVATYYCQKYDSAPLTF

GGGTKVEIK
and/or (2)
a $V_L$ comprising the CDR-Ls thereof, e.g.,:
CDR-L1 comprising the amino acid sequence:
(SEQ ID NO: 11; or a variant thereof)
Gln Asp Ile Ser Asp Tyr CDR-L2 comprising the amino acid sequence:
(SEQ ID NO: 12; or a variant thereof)
Thr Thr Ser CDR-L3 comprising the amino acid sequence:
(SEQ ID NO: 13; or a variant thereof)
Gln Lys Tyr Asp Ser Ala Pro Leu Thr
and/or a $V_H$ comprising the CDR-Hs thereof, e.g.,:
CDR-H1 comprising the amino acid sequence:
(SEQ ID NO: 14; or a variant thereof)
Gly Phe Thr Phe Ser Ala Tyr Ala CDR-H2 comprising the amino acid sequence:
(SEQ ID NO: 15; or a variant thereof)
Ile Ser Gly Ser Gly Gly Ser Ala CDR-H3 comprising the amino acid sequence:
(SEQ ID NO: 16; or a variant thereof)
Ala Lys Asp Gly Ala Trp Lys Met Ser Gly Leu Asp Val;
and/or (3)
a heavy chain immunoglobulin comprising the amino acid sequence:
(SEQ ID NO 27)
EVQVLESGGDLVQPGGSLRLSCAASGFTFSAYAMTWVRQAPGKGLEWVSA

ISGSGGSAYYADSVKGRFTISRDNSKNTVYLQMNSLRAEDTAVYYCAKDG

AWKMSGLDVWGQGTTVIVSSASTKGPSVFPLAPCSRSTSESTAALGCLVK

DYFPEPVTVSWNSGALTSGVHTFPAVLQSSGLYSLSSVVTVPSSSLGTKT

YTCNVDHKPSNTKVDKRVESKYGPPCPPCPAPEFLGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

-continued

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK (or a variant thereof),
and a light chain immunoglobulin comprising the amino acid sequence:
(SEQ ID NO 28)
DIQMTQSPASLSASVGDRVTITCRASQDISDYLAWYQQKPGKIPRLLIYT

TSTLQSGVPSRFRGSGSGTDFTLTISSLQPEDVATYYCQKYDSAPLTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC (or a variant thereof)

In an embodiment of the invention, such a $V_L$ is linked to a human kappa or lambda light chain immunoglobulin constant domain and/or such a $V_H$ is linked to a human IgG (e.g., IgG1, IgG2, IgG3 or IgG4 (for example, an S228P mutant IgG4)) heavy chain immunoglobulin constant domain.

Activin A Antagonists

The present invention includes LEPR/GDF8/ActA combinations (e.g., H4H18457P2/H4H1657N2/H4H10446P2) which include one or more Activin A antagonists.

Activin A antagonists include antibodies and antigen-binding fragments thereof and other substances (e.g., peptides and small molecules) that specifically bind to Activin A and antagonize one or more biological activities of Activin A. Molecules that specifically bind to Activin A may be referred to as "anti-Activin A" or "anti-ActA". In an embodiment of the invention, such an ActA antagonist:

(i) interferes with the interaction between Activin A and an Activin A receptor (e.g., Activin Type IIA receptor, Activin Type IIB receptor, Activin Type I receptor, etc.);
(ii) interferes with the formation of Activin-Activin receptor complexes; and/or
(iii) results in inhibition of at least one biological function of Activin A such as phosphorylation and activation of Type I Activin receptors and the phosphorylation of SMAD2 and 3 proteins.

Activin A antagonists, such as antibodies and antigen-binding fragments thereof and other substances (e.g., peptides) specifically bind to Activin A or the βA subunit thereof. An antigen-specific binding protein that specifically binds the βA subunit may recognize both Activin A (βA/βA homodimer) and Activin AB (βA/βB heterodimer). In an embodiment of the invention, an Activin A-specific binding protein binds both Activin A and Activin AB (but not Activin B). Anti-Activin A antibodies and antigen-binding fragments are mentioned in, e.g., US2009/0234106. A particular anti-Activin A antibody is designated "MAB3381," and is available commercially from R&D Systems, Inc, Minneapolis, Minn. MAB3381 specifically binds Activin A (homodimer) as well as Activin AB (heterodimer).

In an embodiment of the invention, the Activin A antagonist is an antibody or antigen-binding fragment selected from H4H10423P, H4H10424P, H4H10426P, H4H10429P, H4H10430P, H4H10432P2, H4H10433P2, H4H10436P2, H4H10437P2, H4H10438P2, H4H10440P2, H4H10442P2, H4H10445P2, H4H10446P2, H4H10447P2, H4H10448P2, H4H10452P2, H4H10468P2 and H2aM10965N; or any other antibody or antigen-binding fragment set forth in WO2015/017576.

In an embodiment of the invention, the anti-Activin A antibody is garetosmab.

In an embodiment of the invention, the anti-Activin A antibody or fragment of the present invention comprises:

(i) the HCDRs (HCDR1, HCDR2 and HCDR3) of a heavy chain variable region (or having variants of one or more of the HCDRs) and/or the LCDRs (LCDR1, LCDR2 and LCDR3) of a light chain variable region (or having variants of one or more of the LCDRs) of an antibody selected from H4H10423P, H4H10424P, H4H10426P, H4H10429P, H4H10430P, H4H10432P2, H4H10433P2, H4H10436P2, H4H10437P2, H4H10438P2, H4H10440P2, H4H10442P2, H4H10445P2, H4H10446P2, H4H10447P2, H4H10448P2, H4H10452P2, H4H10468P2 and H2aM10965N; and/or (ii) the heavy chain variable region (or a variant thereof) and/or light chain variable region (or a variant thereof) of an antibody selected from 1141110423P, 1141110424P, H4H10426P, H4H10429P, H4H10430P, H4H10432P2, H4H10433P2, H4H10436P2, H4H10437P2, H4H10438P2, H4H10440P2, H4H10442P2, H4H10445P2, H4H10446P2, H4H10447P2, H4H10448P2, H4H10452P2, H4H10468P2 or H2aM10965N;

and/or is characterized as:

(iii) competing for binding to Activin A with 1141110423P, 1141110424P, 1141110426P, H4H10429P, H4H10430P, H4H10432P2, H4H10433P2, H4H10436P2, H4H10437P2, H4H10438P2, H4H10440P2, H4H10442P2, H4H10445P2, H4H10446P2, H4H10447P2, H4H10448P2, H4H10452P2, H4H10468P2 and/or H2aM10965N;

and/or (iv) binding to Activin A at the same epitope as 1141110423P, 1141110424P, 1141110426P, H4H10429P, H4H10430P, H4H10432P2, H4H10433P2, H4H10436P2, H4H10437P2, H4H10438P2, H4H10440P2, H4H10442P2, H4H10445P2, H4H10446P2, H4H10447P2, H4H10448P2, H4H10452P2, H4H10468P2 and/or H2aM10965N.

See published international patent application publication no. WO2015/017576. In an embodiment of the invention, such an antibody or fragment comprises a heavy chain constant domain selected from IgG1, IgG2, IgG3 and IgG4 and/or a light chain constant domain selected from kappa and lambda.

Antibody H4H10446P2 may be referred to as REGN2477 or garetosmab.

In an embodiment of the invention the Activin A antagonist is an antibody or antigen-binding fragment thereof comprising:

(1)
a $V_H$ comprising the amino acid sequence:
(SEQ ID NO: 17; or a variant thereof)
QVQLQESGPGLVKPSETLSLTCTVSGGSFSSHFWSWIRQPPGKGLEWIGY
ILYTGGTSFNPSLKSRVSMSVGTSKNQFSLKLSSVTAADTAVYYCARARS
GITFTGIIVPGSFDIWGQGTMVTVSS;

-continued and a $V_L$ comprising the amino acid sequence:
(SEQ ID NO: 18; or a variant thereof)
EIVLTQSPOTLSLSPGERATLSCRASQSVSSSYLAWYQQKPGQAPRLLIY
GASSRATGIPDRFSGSGSGTDFTLTISRLEPEDFAVYYCQQYGSSPWTFG
QGTKVEIK;
and/or (2)
a $V_L$ comprising the CDR-Ls thereof, e.g.,:
CDR-L1 comprising the amino acid sequence:
(SEQ ID NO: 19; or a variant thereof)
Gln Ser Val Ser Ser Ser Tyr;

CDR-L2 comprising the amino acid sequence:
(SEQ ID NO: 20; or a variant thereof)
Gly Ala Ser;
and CDR-L3 comprising the amino acid sequence:
(SEQ ID NO: 21; or a variant thereof)
Gln Gln Tyr Gly Ser Ser Pro Trp Thr;
and a $V_H$ comprising the CDR-Hs thereof, e.g.,:
CDR-H1 comprising the amino acid sequence:
(SEQ ID NO: 22; or a variant thereof)
Gly Gly ser Phe Ser Ser His Phe;

CDR-H2 comprising the amino acid sequence:
(SEQ ID NO: 23; or a variant thereof)
Ile Leu Tyr Thr Gly Gly Thr;
and CDR-H3 comprising the amino acid sequence:
(SEQ ID NO: 24; or a variant thereof)
Ala Arg Ala Arg Ser Gly Ile Thr Phe Thr Gly
Ile Ile Val Pro Gly Ser Phe Asp Ile;
and/or (3)
a heavy chain immunoglobulin comprising the amino acid sequence:
(SEQ ID NO: 29)
QVQLQESGPGLVKPSETLSLTCTVSGGSFSSHEWSWIRQPPGKGLEWIGY
ILYTGGTSFNPSLKSRVSMSVGTSKNQFSLKLSSVTAADTAVYYCARARS
GITFTGIIVPGSFDIWGQGTMVTVSSASTKGPSVFPLAPCSRSTSESTAA
LGCLVKDYFPEPVTVSWNSGALTSGVHTFPAVLQSSGLYSLSSVVTVPSS
SLGTKTYTCNVDHKPSNTKVDKRVESKYGPPCPPCPAPEFLGGPSVFLFP
PKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPR
EPQVYTLPPSQEEMTKNQVSLTCLVKGFYPSDIAVEWESNGQPENNYKTT
PPVLDSDGSFFLYSRLTVDKSRWQEGNVESCSVMHEALHNHYTQKSLSLS
LGK (or a variant thereof)
and a light chain immunoglobulin comprising the amino acid sequence:
(SEQ ID NO: 30)
EIVLTQSPGTLSLSPGERATLSCRASQSVSSSYLAWYQQKPGQAPRLLIY
GASSRATGIPDRFSGSGSGTDFTLTISRLEPEDFAVYYCQQYGSSPWTFG
QGTKVEIKRTVAAPSVFIFPPSDEQLKSGTASVVCLLNNEYPREAKVQWK
VDNALQSGNSQESVTEQDSKDSTYSLSSTLTLSKADYEKHKVYACEVTHQ
GLSSPVTKSENRGEC (or a variant thereof).

In an embodiment of the invention, such a $V_L$ is linked to a human kappa or lambda light chain immunoglobulin constant domain and/or such a $V_H$ is linked to a human IgG (e.g., IgG1, IgG2, IgG3 or IgG4 (for example, an S228P mutant IgG4)) heavy chain immunoglobulin constant domain.

Pharmaceutical Compositions

The present invention includes pharmaceutical formulations of the LEPR/GDF8/ActA combinations of the present invention (e.g., H4H18457P2/H4H1657N2/H4H10446P2), including, for example, or one or more (e.g., 3) components thereof admixed with a pharmaceutically acceptable carrier or excipient. See, e.g., Remington's Pharmaceutical Sciences and U.S. Pharmacopeia: National Formulary, Mack Publishing Company, Easton, Pa. (1984). Methods for making such a pharmaceutical formulation comprising admixing a pharmaceutically acceptable carrier or excipient with the component(s) forms part of the present invention as do the pharmaceutical compositions that are produced by such methods.

The scope of the present invention includes desiccated, e.g., freeze-dried, LEPR/GDF8/ActA combinations of the present invention (e.g., H4H18457P2/H4H1657N2/H4H10446P2) or one or more components thereof or a pharmaceutical composition thereof that includes a pharmaceutically acceptable carrier but substantially lacks water. In an embodiment of the invention, the pharmaceutical formulation is aqueous (includes water). In an embodiment of the invention, the pharmaceutical formulation is sterile.

Pharmaceutical formulations of therapeutic agents may be prepared by mixing with acceptable carriers, excipients, or stabilizers in the form of, e.g., lyophilized powders, slurries, aqueous solutions or suspensions (see, e.g., Hardman et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

The mode of administration of LEPR/GDF8/ActA combinations can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

The present invention provided methods for administering pharmaceutical formulations comprising a LEPR/GDF8/ActA combination (e.g., H4H18457P2/H4H1657N2/H4H10446P2) to a subject (e.g., a human) comprising introducing the formulation into the body of the subject, e.g., into a vein, the subcutis or the muscular tissue of the subject. For example, the method comprises piercing the body of the subject with a needle of a syringe and injecting the formulation into the body of the subject. Such a method includes introducing a formulation comprising all three components of the combination, which are co-formulated, in the body of the subject; or, for example, introducing three separately formulated components of the combination in the body of the subject.

The present invention provides one or more vessels (e.g., a plastic or glass vial, e.g., with a cap, or a chromatography column, hollow bore needle or a syringe cylinder) comprising LEPR/GDF8/ActA combinations of the present invention (e.g., H4H18457P2/H4H1657N2/H4H10446P2) or a pharmaceutical composition thereof comprising a pharmaceutically acceptable carrier. The present invention includes methods for preparing one or more vessels comprising the combination comprising introducing the components of the combination into one or more vessels, e.g., a single vessel comprising a combination of components which are co-formulated. In an embodiment of the invention, the vessel(s) is/are then introduced into a kit.

The present invention also provides a device, e.g., an injection device, comprising LEPR/GDF8/ActA combinations of the present invention (e.g., H4H18457P2/H4H1657N2/H4H10446P2) or a pharmaceutical composition thereof and methods of use thereof. An injection device is a device that introduces a substance into the body of a patient via a parenteral route, e.g., intramuscular, subcutaneous or intravenous. For example, an injection device may be a syringe (e.g., pre-filled with the pharmaceutical composition, such as an auto-injector, or filled at the point of use, e.g., by the user or a clinician) which, for example, includes a cylinder or barrel for holding fluid to be injected (e.g., comprising the antibody or fragment or a pharmaceutical composition thereof), a needle for piercing skin and/or blood vessels for injection of the fluid; and a plunger for pushing the fluid out of the cylinder and through the needle bore.

The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556. Such needleless devices and methods of use thereof comprising the pharmaceutical composition are also part of the present invention.

The present invention includes methods for preparing one or more injection devices (e.g., pre-filled syringe or autoinjector) comprising the LEPR/GDF8/ActA combination (e.g., H4H18457P2/H4H1657N2/H4H10446P2) comprising introducing the components of the combination into one or more of such devices, e.g., a single device comprising the combination components which are co-formulated. In an embodiment of the invention, the injection device(s) is/are then introduced into a kit.

The present invention also includes kits comprising the a LEPR/GDF8/ActA combination of the invention (e.g., H4H18457P2/H4H1657N2/H4H10446P2). In an embodiment of the invention, the kit comprises each antagonist in a separate vessel or injection device (e.g., pre-filled syringe or autoinjector); or all three antagonists co-formulated in a single vessel or injection device. The kit can include a package insert including information concerning the pharmaceutical compositions and dosage forms in the kit. Generally, such information aids patients and physicians in using the enclosed pharmaceutical compositions effectively and safely. For example, any of the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

Treatment and Administration

The LEPR/GDF8/ActA combination has demonstrated an exceptional ability to bring about an increase in lean mass in subjects administered the combination. Such increases in lean mass possibly is at the expense of increases in fat mass. The LEPR/GDF8/ActA combination brings about greater increases in lean mass vs blockade of only GDF8 and ActA and there is less of an increase in fat mass as compared to what is observed with the LEPR antagonist alone. This may be due to calories from the fat now being used to build the extra muscle.

Methods for administering a LEPR/GDF8/ActA combination of the present invention (e.g., H4H18457P2/H4H1657N2/H4H10446P2) to a subject include introducing components of the combination, in association with one another, into the body of the subject. Such introduction may be done by any acceptable route, e.g., parenterally. Such components may be co-formulated into a single composition or formulated into separate compositions. Administration of one or more of the components in separate compositions may be separated in time if such administrations are done as part of a regimen. In an embodiment of the invention, the method comprises injecting all three components into the subject at once; in another embodiment of the invention, the GDF8 antagonist and the ActA antagonist are formulated together and are injected at once along with the LEPR antagonist in a separate injection; in another embodiment of the invention, all three antagonists are injected separately in three individual injections (e.g., subcutaneous, intravenous or intramuscular or a combination of two or three of such routes).

The scope of the present invention provides methods for increasing food intake, adiposity, body weight (e.g., at the expense of fat mass), muscle strength, muscle fiber size or lean mass (e.g., at the expense of fat mass) in a subject in need thereof comprising administering a therapeutically effective amount of LEPR/GDF8/ActA combinations (e.g., H4H18457P2/H4H1657N2/H4H10446P2) to the subject.

Moreover, LEPR/GDF8/ActA combinations of the present invention (e.g., H4H18457P2/H4H1657N2/H4H10446P2) may be used to:

- treat or prevent a disease or condition which would be cured or ameliorated to any degree by antagonism of (i) LEPR (e.g., hyperleptinemia or elevated expression of the OB-R leptin receptor that results in excess LEPR signaling), (ii) GDF8 (e.g., muscle atrophy/wasting) and/or (iii) ActA; and/or
- treat or prevent a disease or condition which would be cured or ameliorated to any degree by causing an increase or reversing decreases in food intake, adiposity, body weight (e.g., at the expense of fat mass), muscle fiber size muscle strength or lean mass (e.g., at the expense of fat mass);

by administering a therapeutically effective amount of LEPR/GDF8/ActA combinations (e.g., H4H18457P2/H4H1657N2/H4H10446P2) to the subject. Such diseases or conditions that can be treated or prevented include, for example, malnutrition, failure to thrive, insufficient food/caloric intake, eating disorders, cachexia, muscle atrophy/wasting, age-related sarcopenia, and muscle injury. Such conditions and diseases are discussed in detail herein.

Malnutrition is an example of a condition, in a subject, that would benefit from LEPR/GDF8/ActA combination therapy. Malnutrition is a term used to describe any imbalance in nutrition; from over-nutrition to under-nutrition e.g., as seen in hospitals and residential care facilities. For the purposes of the present invention, malnutrition refers to under-nutrition (unless otherwise stated). Thus, the present invention provides methods for treating or preventing malnutrition in a subject, e.g., who is in a hospital or residential care facility, by administering a therapeutically effective amount of LEPR/GDF8/ActA combination to the subject in need thereof.

Malnutrition can develop as a consequence of:

- deficiency in dietary intake;
- increased requirements associated with a disease state (e.g., HIV-infected subjects and subjects with AIDS (acquired immune deficiency syndrome) or cystic fibrosis may require increased dietary intake in order to maintain normal body weight) for which an increase in dietary intake is not sufficient to compensate; and/or
- complications of an underlying illness (e.g., patients suffering from cirrhosis, chronic pancreatitis, lactase deficiency, pancreatic cancer, amyloidosis, celiac disease, Crohn's disease, radiation enteritis and Addison's disease may suffer from malabsorption due to insufficient digestive agents; and patients suffering from cancer or infectious diseases (or other diseases) may develop cachexia secondary to the underlying illness (see below)) for which an increase in dietary intake is not sufficient to compensate.

Thus, the present invention includes methods for reversing or halting malnutrition in a subject which is the consequence of a deficiency in dietary intake, increased requirements associated with a disease state (e.g., HIV or AIDS), and/or complications of an underlying illness comprising administering a therapeutically effective amount of LEPR/GDF8/ActA combination (e.g., H4H18457P2/H4H1657N2/H4H10446P2) to the subject.

Malnutrition is associated with negative outcomes for patients, including higher infection and complication rates, increased muscle loss, impaired wound healing, longer length of hospital stay and increased morbidity and mortality. Thus, the present invention includes methods for reducing negative outcomes (e.g., for reducing the possibility of infection or for preventing impaired wound healing) for a subject which are associated with malnutrition comprising administering a therapeutically effective amount of LEPR/GDF8/ActA combinations (e.g., H4H18457P2/H4H1657N2/H4H10446P2) to the subject.

Numerous nutrition screening and assessment tools exist to identify the risk of malnutrition and to diagnose malnutrition. For example, The Malnutrition Screening Tool (MST) is a simple, three-question tool assessing recent weight and appetite loss validated for use in general medical, surgical and oncology patients (Anthony, Nutrition screening tools for hospitalized patients. Nutr. Clin. Pract. 2008; 23:373-382; Ferguson et al., Validation of a malnutrition screening tool for patients receiving radiotherapy. Australas. Radiol. 1999; 43:325-327). The Mini Nutrition Assessment (MNA) was developed specifically for use among elderly patients (65 years) in hospitals, nursing homes and the community and is thus limited to this demographic (Anthony, Nutrition screening tools for hospitalized patients, Nutr. Clin. Pract. 2008; 23:373-382; Gibson, Principles of Nutritional Assessment. 2$^{nd}$ ed. Oxford University Press, Inc; New York, N.Y., USA: 2005). Nutritional Risk Screening (NRS-2002) uses recent weight loss, decreased BMI and reduced dietary intake, combined with a subjective assessment of disease severity (based on increased nutrition requirements and/or metabolic stress), to generate a nutrition risk score (Anthony, Nutrition screening tools for hospitalized patients, Nutr. Clin. Pract. 2008; 23:373-382). The four item Short Nutrition Assessment Questionnaire (SNAQ) was developed to diagnose malnutrition in hospitalised patients and provides an indication for dietetic referrals as well as outlining a nutrition treatment plan (Anthony, Nutrition screening tools for hospitalized patients, Nutr. Clin. Pract. 2008; 23:373-382; Kruizenga et al., Development and validation of a hospital screening tool for malnutriton: the short nutritional assessment questionnaire (SNAQ) Clin. Nutr. 2005; 24:75-82). It has been validated for hospital inpatient and outpatient use, as well as residential patients and does not require calculation of BMI (Kruizenga et al. The SNAQ(RC), an easy traffic light system as a first step in the recognition of undernutrition in residential care. J. Nutr. Health Aging. 2010; 14:83-89; Neelemaat et al., Screening malnutrition in hospital outpatients. Can the SNAQ malnutrition screening tool also be applied to this population? Clin. Nutr. 2008; 27:439-446). Subjective Global Assessment (SGA) is one of the most commonly used nutrition assessment tools, and assesses nutrition status via completion of a questionnaire which includes data on weight change, dietary intake change, gastrointestinal symptoms, changes in functional capacity in relation to malnutrition as well as assessment of fat and muscle stores and the presence of oedema and ascites (Detsky et al., What is subjective global assessment of nutritional status? J Parenter Enteral Nutr. 1987; 11:8-13).

Hospital malnutrition is a condition experienced by a subject admitted to a hospital. The state of malnutrition may be pre-existing or develop during the subject's hospital stay. The present invention provides methods for treating or preventing hospital malnutrition in a subject comprising administering a therapeutically effective amount of LEPR/GDF8/ActA combinations (e.g., H4H18457P2/H4H1657N2/H4H10446P2) to the subject.

Malnutrition is also a common condition suffered by subjects with cystic fibrosis. A variety of complex factors, both related and unrelated, may give rise to energy imbalance in patients with cystic fibrosis. The net effect on growth potential varies considerably from patient to patient according to differences in disease expression and with progression of the disease. The present invention provides methods for treating or preventing malnutrition in a subject suffering from cystic fibrosis comprising administering a therapeutically effective amount of LEPR/GDF8/ActA combinations (e.g., H4H18457P2/H4H1657N2/H4H10446P2) to the subject.

Failure to thrive in childhood is a state of undernutrition due to inadequate caloric intake, inadequate caloric absorption, or excessive caloric expenditure. In newborns, failure to thrive may be associated with common underlying diseases such as short bowel following necrotizing enterocolitis, *volvulus* and intestinal resections, congenital resorption defects and structural defects of the small intestine and insufficient food intake. In infants (2-8 months of age), failure to thrive may be associated with common underlying diseases such as insufficient food intake, neglect, intestinal allergy to cow's milk protein, esophagitis with gastroesophogeal reflux, cystic fibrosis, eating disorders and/or increased energy requirements in case of underlying cardiac, neurological, oncological or renal disease, celiac disease, chronic diarrhea in case of immune-system defects, autoimmune enteropathy, postenteritis syndrome and malabsorption syndromes and munchausen syndrome by proxy. In small children (9-36 months), failure to thrive may be associated with common underlying diseases such as insufficient food intake, neglect, celiac disease, cystic fibrosis, eating disorders and/or increased energy requirements in case of underlying cardiac, neurological, oncological or renal disease, chronic diarrhea in case of immune-system defects and munchausen syndrome by proxy. In children (3-16 years), failure to thrive may be associated with common underlying diseases such as insufficient food intake, neglect, psychiatric disorders such as anorexia nervosa, chronic inflammatory intestinal disorders, celiac disease, cystic fibrosis, eating disorders and/or increased energy requirements in case of underlying cardiac, neurological, oncological or renal disease, chronic diarrhea in case of immune-system defects and lambliasis and other chronic intestinal infections. The present invention provides methods for treating or preventing childhood failure to thrive in a subject (e.g., in a newborn, infant, small child or child), for example, which is characterized by any one or more of the diseases or conditions discussed herein, comprising administering a therapeutically effective amount of LEPR/GDF8/ActA combinations (e.g., H4H18457P2/H4H1657N2/H4H10446P2) to the subject.

Insufficient food intake may be associated with the following symptoms: lack of appetite, chronic vomiting, swallowing and chewing disorders, esophageal dysmotility and shortness of breath e.g., associated with heart and lung disorders. The present invention provides methods for treating or preventing insufficient food intake, e.g., which is associated with the symptoms discussed herein, in a subject comprising administering a therapeutically effective amount of LEPR/GDF8/ActA combinations (e.g., H4H18457P2/H4H1657N2/H4H10446P2) to the subject.

Eating disorders characterized by inadequate caloric intake include anorexia and/or bulimia. The present invention provides methods for treating or preventing anorexia and/or bulimia in a subject comprising administering a therapeutically effective amount of LEPR/GDF8/ActA combinations (e.g., H4H18457P2/H4H1657N2/H4H10446P2) to the subject. In an embodiment of the invention, anorexia is anorexia nervosa, anorexia of aging, anorexia in a patient receiving hemodialysis.

Cachexia is a complex metabolic syndrome often associated with underlying illness and characterized by loss of muscle with or without loss of fat mass. The prominent clinical feature of cachexia is weight loss in adults (corrected for fluid retention) or growth failure in children (excluding endocrine disorders). Anorexia, inflammation, insulin resistance and increased muscle protein breakdown are symptoms frequently associated with cachexia. The present invention provides methods for treating or preventing cachexia (or any symptoms of cachexia), e.g., at any stage set forth herein (e.g., refractory cachexia) and/or as defined by any of the criteria set forth herein or in the art, in a subject comprising administering a therapeutically effective amount of LEPR/GDF8/ActA combinations (e.g., H4H18457P2/H4H1657N2/H4H10446P2) to the subject.

Cachexia secondary to other diseases, conditions or treatments includes cachexia secondary to anorexia or other psychiatric eating disorders, pulmonary disease (e.g., chronic obstructive pulmonary disorder (COPD)), chronic kidney disease, infectious disease (e.g., HIV-infection or acquired immune deficiency syndrome (AIDS)), congestive heart failure, radiation treatment, cancer (e.g., hepatocellular carcinoma, melanoma and/or breast cancer), chronic heart failure, autoimmune disorders (e.g., inflammatory bowel disease, lupus erythematosus, multiple sclerosis, rheumatoid arthritis, Crohn's disease or psoriasis), cystic fibrosis, cardiovascular diseases, elevated blood pressure, depression and/or neurodegenerative disorders. The present invention provides methods for treating or preventing cachexia which is secondary to any disease or condition, e.g., any of the disease or conditions set forth herein (e.g., cancer), in a subject comprising administering a therapeutically effective amount of LEPR/GDF8/ActA combinations (e.g., H4H18457P2/H4H1657N2/H4H10446P2) to the subject.

The international consensus statement on the definition and classification of cancer cachexia, published in May 2011 in Lancet Oncology, established these criteria for diagnosing cachexia in patients with cancer:

(i) Weight loss greater than 5 percent over the past 6 months; or (ii) BMI less than 20 and any degree of weight loss greater than 2 percent; or (iii) Appendicular skeletal muscle index consistent with sarcopenia (another wasting syndrome) and weight loss of more than 2 percent. Fearon et al., Lancet Oncol. 2011 May; 12(5):489-95.

The stages of cancer cachexia agreed upon by the panel are:

precachexia: weight loss of less than 5 percent, along with other symptoms such as impaired glucose tolerance or anorexia;

cachexia: weight loss greater than 5 percent or other symptoms and conditions consistent with the diagnostic criteria for cachexia; and refractory cachexia: patients experiencing cachexia who are no longer responsive to cancer treatment, have a low performance score, and have a life expectancy of less than 3 months.

Muscle atrophy or wasting occurs in muscles with denervation or inactivity, but is also a systemic response to fasting and various diseases and conditions. Muscle atrophy may be in the form of myopenia, a decline in muscle mass, and/or dynapenia, a decline in muscle strength. These diseases and conditions include sepsis, AIDS, renal and cardiac failure, excessive glucocorticoids (e.g., Cushing syndrome) and trauma, and muscle atrophy also occurs in 80% of patients with cancer. In addition, muscle atrophy or wasting may be caused by or associated with disuse, immobilization, bed rest, injury (e.g., hip fracture), neurodegenerative diseases associated with motoneuron loss, medical treatment or surgical intervention (e.g., hip replacement, knee replacement, etc.) or by necessity of mechanical ventilation. The present invention provides methods for treating or preventing muscle atrophy or wasting (e.g., which is secondary to a disease or condition such as, for example, AIDS or cancer), in a subject comprising administering a therapeutically effective amount of LEPR/GDF8/ActA combinations (e.g., H4H18457P2/H4H1657N2/H4H10446P2) to the subject. In an embodiment of the invention, the muscle atrophy is a sarcopenia such as age-related sarcopenia or sarcopenia in a subject receiving hemodialysis and/or suffering from chronic kidney disease cachexia. Age-related sarcopenia is the degenerative loss of skeletal muscle mass (e.g., about 0.5-1% loss per year after the age of 50), quality, and strength associated with aging. Thus, the present invention includes method for treating or preventing muscle atrophy due to age-related sarcopenia.

Muscle injury may be caused by strain from overexertion or a sudden twist, e.g., a strain or a tear. A muscle tear might cause swelling, pain, and severe bleeding, which can lead to a blood clot. Serious tears may require surgery. The muscle stimulating properties of the LEPR/GDF8/ActA combinations make them useful for the treatment or prevention of muscle injury. The present invention provides methods for treating or preventing muscle injury, in a subject, comprising administering a therapeutically effective amount of LEPR/GDF8/ActA combinations (e.g., H4H18457P2/H4H1657N2/H4H10446P2) to the subject.

Other conditions that may be treated or prevented using the LEPR/GDF8/ActA combinations of the present invention include amyotrophic lateral sclerosis, arthritis, autoimmune disorders, benign and malignant pheochromocytoma, breast cancer, cancer, cardiovascular diseases, chronic heart failure, chronic obstructive pulmonary disease, depression, diabetes, elevated blood pressure, glucocorticoid-induced myopathy, hepatocellular carcinoma, inflammatory bowel disease, keloids and hypertrophic scars, lupus erythematosus, melanoma, metabolic syndromes, multiple sclerosis, muscular dystrophy (e.g., Myotonic, Duchenne, Becker, Limb-girdle, Facioscapulohumeral (FSHD, also known as Landouzy-Dejerine disease), Congenital, Oculopharyngeal, Distal, Emery-Dreifuss, etc.), neurodegenerative disorders, organ atrophy, osteoarthritis, osteopenia, osteoporosis, Parkinson's disease, preeclampsia, psoriasis, pulmonary artery hypertension, sarcopenia, sepsis and uterine fibroids/leiomyomata.

LEPR/GDF8/ActA combinations (e.g., H4H18457P2/H4H1657N2/H4H10446P2) of the present invention are effective for increasing lean muscle mass and muscle strength and, thus, are effective for enhancing athletic performance. Thus, the present invention provides methods for enhancing athletic performance in a subject in need thereof comprising administering a therapeutically effective amount of LEPR/GDF8/ActA combinations (e.g., H4H18457P2/H4H1657N2/H4H10446P2) to the subject. Athletic performance includes walking speed, running speed, ability to sit and stand per unit time (e.g., over 30 seconds), walking distance per unit time (e.g., over 6 minutes), bicep curl weight, chest press weight, stair climb speed (e.g., time to climb 4 steps) and/or hand grip strength (e.g., as measured using manual dynamometry). In an embodiment of the invention, the subject is undergoing stroke rehabilitation (e.g., rehabilitation for stroke hemiparesis) or physical therapy. Thus, the LEPR/GDF8/ActA combinations of the present invention can be used as an adjunct to any therapeutic procedure wherein an increase in athletic performance would be desirable, e.g., physical therapy, for example, stroke rehabilitation or for recovery from surgery (e.g., knee surgery to repair tendon or ligament damage or knee replacement) or a physical injury.

Subjects (e.g., humans) administered leptin receptor antagonists (e.g., anti-LEPR antibodies) may experience increased liver triglyceride levels or serum triglyceride levels. One method for mitigating this increase is to administer, in association with the LEPR antagonist, an Activin A antagonist (e.g., anti-ActA antibody or antigen-binding fragment thereof) and a GDF8 antagonist (e.g., anti-GDF8 antibody or antigen-binding fragment thereof). For example, such a method may comprise administering a therapeutically effective amount of a LEPR/GDF8/ActA combination (e.g., H4H18457P2/H4H1657N2/H4H10446P2).

A "subject" is a mammal such as, for example, a human, dog, cat, horse, cow, mouse, rat, monkey (e.g., cynomolgous monkey, e.g., *Macaca fascicularis* or *Macaca* mulatta) or rabbit.

An effective or therapeutically effective dose of LEPR/GDF8/ActA combinations (e.g., H4H18457P2/H4H1657N2/H4H10446P2) of the present invention, is from about 0.1 to about 200 mg/kg (of all three antibodies or antigen-binding fragments), e.g., for treatment or prevention of any of the diseases or conditions discussed herein (e.g., cachexia).

In particular embodiments, the LEPR/GDF8/ActA combinations of the present invention (e.g., H4H18457P2/H4H1657N2/H4H10446P2) may be used alone or in association with any other, further therapeutic agents and/or therapeutic procedures, e.g., which are useful for increasing food intake, adiposity, body weight, lean mass (e.g., muscle mass) and/or strength in a subject and/or for treating or preventing any of the diseases or conditions discussed herein, e.g., cachexia.

In an embodiment of the invention, the therapeutic procedure is nasogastric tube feeding.

In an embodiment of the invention, the further therapeutic agent is any one or more of an appetite stimulant, a cannabinoid, an angiotensin-converting enzyme (ACE) inhibitor, an angiotensin receptor blocker, a smooth muscle relaxant, a nitrate, a diuretic, iron, a bronchodilator, an anticholinergic, a corticosteroid, an antibiotic, a nonsteroidal anti-inflammatory drug (NSAID), an immunosuppressant, an HMG-CoA reductase inhibitor, an anti-depressant, an anti-cancer therapy or a topical agent.

In an embodiment of the invention, the further therapeutic agent is any one or more of 5-fluorouracil (5-FU), 6-mercaptopurine, a combination of atorvastatin and amlodipine, a combination of lovastatin and niacin, a combination such as simvastatin and ezetimibe, atropine, adalimumab, albuterol, alefacept, alemtuzumab, amitriptyline, anamorelin, arformoterol, aspirin, aspirin, atorvastatin, atropine, azathioprine, azithromycin, benazepril, betamethasone, budesonide, bumetanide, buphenine, bupropion, captopril, carboplatin, celecoxib, certolizumab pegol, chlorothiazide, chlorthalidone, ciclosporin, citalopram, clenbuterol, coal tar, coconut oil, corticosteroids, cyproheptadine, cyclophosphamide, dabrafenib, daclizumab, desoximetasone, desvenlafaxine, dexamethasone, diclofenac, dicyclomine, diflunisal, dimebolin, dimethyl fumarate, dimethyl fumarate, dithranol, docetaxel, dopexamine, doxorubicin, dronabinol, duloxetine, efalizumab, enalapril, enobosarm, epinephrine, epirubicin, erythromycin, escitalopram, etanercept, ethacrynate, etodolac, fentoterol, fingolimod, flunisolide, fluocinonide, fluocortolone, fluoxetine, fluvastatin, formoterol, fosinopril, furosemide, glatiramer acetate, golimumab, hydralazine, hydrochlorothiazide, hydrocortisone, hydrocortisone-17-butyrate, hydrocortisone-17-valerate, hydroxycarbamide, hyoscyamine, hyoscyamine, ibuprofen, indapamide, indomethacin, infliximab, interferon beta-1a, interferon beta-1b, interleukin-2, ipilimumab, isoetarine, isoprenaline, isoproterenol, isosorbide dinitrate, JX-594, ketoprofen, levosalbutamol, lisinopril, lovastatin, megestrol, megestrol acetate, mepenzolate, mesalazine, methotrexate, methotrexate, methyclothiazide, metolazone, mevastatin, mitoxantrone, moexipril, nabilone, naproxen, natalizumab, nivolumab, nortriptyline, ocrelizumab, ofatumumab, oral nutritional supplements (e.g., Protibis cookies or dairy-based supplements), orciprenaline, oxaprozin, paclitaxel, para-aminobenzoic acid, parenteral iron, paroxetine, pembrolizumab, perindopril, phenobarbital, phenobarbital, phenobarbital and scopolamine, pirbuterol, piroxicam, pitavastatin, pravastatin, prednisolone, prednisone, prednisone, procaterol, proline-rich peptide (PRP)-1, psoralen, quinapril, ramapril, ritodrine, rituximab, rosuvastatin, salbutamol, salsalate, scopolamine, sertraline, simvastatin, sorafenib, sulindac, terbutaline, teriflunomide, theophylline, tiotropium, tolmetin, torsemide, trametinib, trandolapril, trazodone, triamcinolone acetonide, triamcinolone alcohol, vemurafenib, venlafacine, venlafaxine, vitamin D3 or a vitamin D analogue.

The present invention also encompasses embodiments wherein a LEPR/GDF8/ActA combination is not in association with a further therapeutic agent and/or procedure.

EXAMPLES

These examples are intended to exemplify the present invention are not a limitation thereof. Compositions e.g., LEPR/GDF8/ActA combinations, and methods set forth in the Examples form part of the present invention.

Example 1: In Vivo Efficacy Testing of LEPR Antagonist Antibodies (H4H17322P2, H4H18457P2 and H4H18464P2) in Humanized LEPR Mice The effects of three specific antagonist anti-LEPR antibodies of the invention, H4H17322P2, H4H18457P2 and H4H18464P2, on food intake, body weight and adiposity were determined in singly-housed genetically engineered LEPR$^{Hu/Hu}$ mice that express a leptin receptor which is composed of the human LEPR ectodomain sequence in place of the murine LEPR ectodomain sequence.

Baseline daily food intake was measured between 5 days and 1 day prior to treatment (days −5 and −1). Four days prior to treatment and 6 days post treatment (days −4 and 6) body composition, including adiposity, was quantified by μCT. At day 0, thirty-two 12- to 13-week old male LEPR$^{HuHu}$ mice were randomized to four groups of 8 mice based on body weight from 1-day pretreatment (day −1). At day 0, each group received via subcutaneous injection either a single dose of isotype control antibody at 30 mg/kg, H4H17322P2 at 30 mg/kg, H4H18457P2 at 30 mg/kg, or H4H18464P2 at 30 mg/kg. The isotype control antibody does not bind any known mouse protein. Body weight was measured for the duration of the study for each animal (Table 1A). The percent change in body weight from day 0 was calculated for each animal at each time point. Table 1B summarizes the average fat mass and lean mass for animals in each antibody treatment group quantified by μCT 6 days prior to and 6 days following antibody treatment. All results are expressed as mean±SEM. Moreover, plasma leptin, both pre-dose and at day 6 were quantitated (Table 10).

Mice treated with the anti-LEPR antagonist antibodies demonstrated increases in percent change in food intake (data not shown) and change in body weight (Table 1A). These increases were not observed with the isotype control antibody treatment. Mice treated with H4H17322P2 at 30 mg/kg exhibited significant increases in food intake starting at one day after treatment (day 1) and at the subsequent time points compared to mice injected with isotype control antibody. Mice treated with H4H18457P2 at 30 mg/kg exhibited a significant increase in food intake starting at day 2 and at the subsequent time points compared to mice injected with isotype control antibody. Mice treated with H4H18464P2 at 30 mg/kg exhibited a significant increase in food intake starting at day 2 and at the subsequent time points, but not day 4 compared to mice injected with isotype control antibody. Mice treated with H4H17322P2 at 30 mg/kg exhibited a significant increase in percent body weight change starting four days after treatment (day 4) and at the subsequent time points compared to mice injected with isotype control antibody. Mice treated with H4H18457P2 at 30 mg/kg exhibited a significant increase in percent body weight change starting at day 3 and at the subsequent time points compared to mice injected with isotype control antibody. Mice treated with H4H18464P2 at 30 mg/kg exhibited a significant increase in percent body weight change starting at day 4 and at subsequent time points compared to mice injected with isotype control antibody. As depicted in Table 1B, there were no differences in fat mass between the groups prior to treatment (day −4). Mice treated with H4H17322P2, H4H18457P2 and H4H18464P2 antibody at 30 mg/kg demonstrated a significant increase in fat mass and leptin levels at 6 days after treatment (day 6) as compared to isotype control antibody (Table 10). In conclusion, treatment with LEPR antagonist antibody, but not an isotype control antibody, increased food intake, body weight, adiposity and leptin levels in mice.

fat mass was quantified by NMR (nuclear magnetic resonance). On day 0, mice were stratified to four groups of 11 to 12 mice based on body composition from day −5 and body weight from day 0. Starting on day 0, each group received the respective antibody treatment dose via subcutaneous injection. REGN1033, REGN2477, and the respective IgG4P mAbs were dosed twice a week at 10 mg/kg; and

TABLE 1A

| Body Weight (g Difference from Baseline) | | | | | | | | | | | | |
|---|---|---|---|---|---|---|---|---|---|---|---|---|
| | REGN1945 30 mg/kg | | | H4H18457 30 mg/kg | | | H4H18464 30 mg/kg | | | H4H17322 30 mg/kg | | |
| | Mean | SEM | N | Mean | SEM | N | Mean | SEM | N | Mean | SEM | N |
| Day 0 | 0.000 | 0.000 | 12 | 0.000 | 0.000 | 12 | 0.000 | 0.000 | 12 | 0.000 | 0.000 | 12 |
| Day 1 | 0.088 | 0.137 | 12 | 0.597 | 0.149 | 12 | 0.300 | 0.153 | 12 | 0.331 | 0.142 | 12 |
| Day 4 | −0.052 | 0.322 | 12 | 2.505 | 0.158 | 12 | 2.215 | 0.212 | 12 | 1.169 | 0.181 | 12 |
| Day 5 | 0.405 | 0.144 | 12 | 2.679 | 0.204 | 12 | 2.433 | 0.239 | 12 | 1.178 | 0.194 | 12 |
| Day 6 | 0.093 | 0.171 | 12 | 2.563 | 0.282 | 12 | 2.062 | 0.229 | 12 | 1.021 | 0.180 | 12 |
| Day 8 | 0.563 | 0.128 | 12 | 3.243 | 0.323 | 12 | 2.959 | 0.360 | 12 | 1.710 | 0.364 | 12 |
| Day 11 | 0.289 | 0.283 | 12 | 3.604 | 0.367 | 12 | 2.927 | 0.434 | 12 | 2.165 | 0.299 | 12 |
| Day 13 | 0.356 | 0.233 | 12 | 3.091 | 0.413 | 12 | 2.116 | 0.317 | 12 | 1.678 | 0.336 | 12 |

REGN1945: Anti-Fel d1 (IgG4)
SEM: standard error of the mean

TABLE 1B

| Body Composition | | | | | | | | | | | | |
|---|---|---|---|---|---|---|---|---|---|---|---|---|
| | REGN1945 30 mg/kg | | | H4H18457 30 mg/kg | | | H4H18464 30 mg/kg | | | H4H17322 30 mg/kg | | |
| | Mean | SEM | N | Mean | SEM | N | Mean | SEM | N | Mean | SEM | N |
| Fat Mass (g Difference from Baseline) | 0.033 | 0.141 | 12 | 1.563 | 0.168 | 12 | 1.396 | 0.217 | 12 | 0.767 | 0.123 | 12 |
| Lean Mass (g Difference from Baseline) | 0.576 | 0.485 | 12 | 0.718 | 0.153 | 12 | 0.724 | 0.297 | 12 | 0.624 | 0.331 | 12 |

TABLE 1C

| Plasma Leptin (pg/mL) | | | | | | | | | | | | |
|---|---|---|---|---|---|---|---|---|---|---|---|---|
| | REGN1945 30 mg/kg | | | H4H18457 30 mg/kg | | | H4H18464 30 mg/kg | | | H4H17322 30 mg/kg | | |
| | Mean | SEM | N | Mean | SEM | N | Mean | SEM | N | Mean | SEM | N |
| Predose | 690.590 | 101.890 | 12 | 1202.452 | 293.789 | 12 | 1068.469 | 224.895 | 12 | 952.510 | 190.816 | 12 |
| Day 6 | 983.476 | 136.172 | 12 | 5956.415 | 977.674 | 12 | 4467.408 | 651.147 | 12 | 3630.862 | 442.252 | 12 |

Example 2: Combination Treatment of Anti-GDF8 mAb (REGN1033), Anti-Activin A mAb (REGN2477), and LEPR Antagonist mAb (H4H18457P2) in 20-24 Week Old Male Mice The effects of the specific antagonist anti-LEPR antibody, H4H18457P2, in combination with the anti-MSTN (also referred to as anti-GDF8) and anti-INHBA (also referred to as anti-Activin A) blocking antibodies, H4H1657N2 (REGN1033) and H4H10446P2 (REGN2477), respectively, of the invention, on food intake, body weight, body composition, individual tissue weights, and ex vivo muscle force generation were determined in singly-housed genetically engineered 20 to 24 week old male $LEPR^{HuHu}$ mice, that express a leptin receptor which is composed of the human LEPR ectodomain sequence in place of the murine LEPR ectodomain sequence.

Baseline daily food intake was measured between days −8 and 0. On day −5 or day −1, baseline whole body lean and H4H18457P2 and its respective IgG4P mAb were dosed once a week at 30 mg/kg; thus, any dose of test antibody given to a test mouse was given in parallel with a corresponding dose of control antibody in a control mouse. The isotype control (IgG4P) (P=denotes a S228P mutation, Eu numbering) antibody did not bind any known mouse protein. The isotype control antibody was REGN1945.

Treatment Groups a) IgG4P Control (10 mg/kg+10 mg/kg, 2×/week; 30 mg/kg, 1×/week), N=11
b) REGN1033+REGN2477 (10 mg/kg+10 mg/kg, 2×/week), N=11
c) H4H18457P2 (30 mg/kg, 1×/week), N=11
d) REGN1033+REGN2477+H4H18457P2 (10 mg/kg+10 mg/kg, 2×/week; 30 mg/kg, 1×/week)).

Food intake (Table 2A) and body weight (Table 2B) were measured for the duration of the study for each animal. Body composition (Tables 2C and 4A-4D) was quantified on day 6 or 7 and day 13 or 14. On day 22, 23 or 24, animals were euthanized and ex vivo force measurements on isolated tibialis anterior muscled were performed (Tables 3A and 3B). Individual organ and skeletal muscle weights were also quantified (Tables 5-7).

Mice treated with either H4H18457P2 alone or in combination with the REGN1033 and REGN2477 exhibited significant increases in cumulative food intake starting at seven days after treatment (day 7) and at the subsequent time points compared to mice injected with isotype control antibody (Table 2A). Mice treated with REGN1033 and REGN2477 showed similar cumulative food intake compared to mice injected with isotype control antibody (Table 2A). Mice treated with H4H18457P2 alone or in combination with REGN1033 and REGN2477, demonstrated increases in body weight beginning 7 days after dosing (day 7) and at the subsequent time points compared to mice treated with isotype control antibody and when compared to mice treated with REGN1033 and REGN2477 (Table 2B). Mice treated with REGN1033 and REGN2477 showed no significant changes in body weight compared to mice treated with isotype control antibody (Table 2B). A significant increase in lean mass from baseline (day −1) was exhibited by mice in each treatment group on days 6, 13 and 20 when compared to mice injected with isotype control (Table 4C). Mice treated with H4H18457P2, REGN1033 and REGN2477 exhibited increased lean mass gain from baseline on days 6, 13 and 20 compared to mice treated with REGN1033 and REGN2477 (Table 4C). Mice treated with REGN1033 and REGN2477 showed a significant decrease in fat mass change from baseline when compared to mice administered isotype control antibody. Mice treated with either H4H18457P2 alone or in combination with the REGN1033 and REGN2477 showed increased fat mass change from baseline at days 6, 13 and 20 when compared to mice administered isotype control antibody and when compared to mice treated with REGN1033 and REGN2477 (Table 4A). Mice treated with H4H18457P2 in combination with REGN1033 and REGN2477 showed a significant reduction in fat mass gain from baseline at days 6, 13 and 20 when compared to mice treated with REGN1033 and REGN2477 (Table 4A). In comparison to mice administered isotype control antibody, mice treated with REGN1033 and REGN2477, as well as mice treated with H4H18457P2, REGN1033 and REN2477 exhibited increased twitch force and peak tetanic force (Table 3A) of isolated tibialis anterior skeletal muscle. Accordingly, mice treated with REGN1033 and REGN2477 and mice treated with H4H18457P2, REGN1033 and REGN3477 exhibited increased skeletal muscle (quadriceps, tibialis anterior and gastrocnemius) weights (Table 5) when compared to mice administered isotype control antibody. Mice treated with H4H18457P2 alone and in combination with REGN1033 and REGN2477 showed increased inguinal, gonadal and brown adipose tissue weights (Table 5) compared to mice administered isotype control antibody. Brown adipose tissue weights (Table 5) were significantly increased in mice treated with H4H18457P2 in combination with REGN1033 and REGN2477 than mice treated with REGN1033 and REGN2477. No significant changes in heart and liver weights (Table 5) were detected amongst the treatment groups when compared to isotype control administration. In summary, these data demonstrate that the LEPR antagonist, H4H18457P2, increases food intake, body weight and increases fat mass in mice. In addition, treatment with the combination of LEPR antagonist, H4H18457P2, with anti-MSTN (REGN1033) and anti-ActA (REGN2477) blocking antibodies leads to increased food intake, body weight, lean mass, fat mass, adipose tissue weight, skeletal muscle weight, and skeletal muscle strength. When compared to REGN1033 and REGN2477 treatment, the combined treatment with H4H18457P2, REGN1033 and REGN2477 leads to additional lean mass increases from baseline and smaller increases in fat mass from baseline.

TABLE 2A

Food Intake (g)

| | Control mAb | | | αGDF8 + αActA | | | LEPR antagonist mAb | | | LEPR antagonist mAb + αGDF8 + αActA | | |
|---|---|---|---|---|---|---|---|---|---|---|---|---|
| | Mean | SEM | N | Mean | SEM | N | Mean | SEM | N | Mean | SEM | N |
| Day 0 | 0.000 | 0.000 | 11 | 0.000 | 0.000 | 11 | 0.000 | 0.000 | 11 | 0.000 | 0.000 | 12 |
| Day 1 | 3.858 | 0.274 | 11 | 3.987 | 0.158 | 11 | 4.554 | 0.380 | 11 | 4.264 | 0.204 | 12 |
| Day 2 | 7.958 | 0.444 | 11 | 8.154 | 0.294 | 11 | 9.784 | 0.679 | 11 | 9.224 | 0.371 | 12 |
| Day 3 | 12.148 | 0.573 | 11 | 12.330 | 0.422 | 11 | 15.246 | 0.919 | 11 | 14.618 | 0.502 | 12 |
| Day 7 | 28.465 | 1.132 | 11 | 28.667 | 0.887 | 11 | 36.752 | 2.059 | 11 | 35.921 | 1.052 | 12 |
| Day 8 | 32.434 | 1.299 | 11 | 32.585 | 1.039 | 11 | 42.095 | 2.394 | 11 | 41.094 | 1.109 | 12 |
| Day 9 | 36.393 | 1.427 | 11 | 36.773 | 1.131 | 11 | 47.590 | 2.737 | 11 | 46.163 | 1.143 | 12 |
| Day 10 | 40.386 | 1.566 | 11 | 40.853 | 1.221 | 11 | 52.779 | 2.874 | 11 | 51.400 | 1.263 | 12 |
| Day 14 | 56.776 | 1.935 | 11 | 57.395 | 1.640 | 11 | 73.535 | 3.966 | 11 | 71.676 | 1.586 | 12 |
| Day 15 | 60.708 | 2.059 | 11 | 61.353 | 1.802 | 11 | 78.424 | 4.353 | 11 | 76.398 | 1.604 | 12 |
| Day 16 | 64.485 | 2.092 | 11 | 65.544 | 1.868 | 11 | 83.396 | 4.662 | 11 | 81.271 | 1.646 | 12 |
| Day 17 | 68.394 | 2.182 | 11 | 69.716 | 1.951 | 11 | 88.506 | 4.993 | 11 | 86.352 | 1.730 | 12 |
| Day 20 | 80.272 | 2.547 | 11 | 82.074 | 2.267 | 11 | 103.698 | 5.970 | 11 | 101.008 | 1.918 | 12 |
| Day 21 | 83.961 | 2.518 | 11 | 85.904 | 2.326 | 11 | 108.243 | 6.360 | 11 | 105.226 | 2.016 | 12 |

TABLE 2B

Body Weight (g Difference from Baseline)

| | Control mAb (N = 11) | | | αGDF8 + αActA | | | LEPR antagonist mAb | | | LEPR antagonist mAb + αGDF8 + αActA | | |
|---|---|---|---|---|---|---|---|---|---|---|---|---|
| | Mean | SEM | N | Mean | SEM | N | Mean | SEM | N | Mean | SEM | N |
| Day 0 | 0.000 | 0.000 | 11 | 0.000 | 0.000 | 11 | 0.000 | 0.000 | 11 | 0.000 | 0.000 | 12 |
| Day 1 | −0.030 | 0.092 | 11 | 0.052 | 0.064 | 11 | 0.614 | 0.172 | 11 | 0.405 | 0.158 | 12 |
| Day 2 | 0.324 | 0.140 | 11 | 0.504 | 0.104 | 11 | 1.355 | 0.218 | 11 | 1.431 | 0.210 | 12 |
| Day 3 | 0.222 | 0.162 | 11 | 0.644 | 0.107 | 11 | 1.791 | 0.224 | 11 | 2.273 | 0.187 | 12 |
| Day 7 | −0.008 | 0.133 | 11 | 1.314 | 0.152 | 11 | 3.192 | 0.327 | 11 | 4.383 | 0.288 | 12 |
| Day 8 | 0.089 | 0.134 | 11 | 1.585 | 0.177 | 11 | 3.559 | 0.288 | 11 | 4.772 | 0.348 | 12 |
| Day 9 | 0.139 | 0.189 | 11 | 1.908 | 0.151 | 11 | 4.088 | 0.380 | 11 | 5.251 | 0.361 | 12 |
| Day 10 | −0.106 | 0.141 | 11 | 1.849 | 0.171 | 11 | 4.244 | 0.374 | 11 | 5.489 | 0.296 | 12 |
| Day 14 | 0.217 | 0.248 | 11 | 2.229 | 0.217 | 11 | 4.931 | 0.417 | 11 | 6.666 | 0.299 | 12 |
| Day 15 | 0.171 | 0.265 | 11 | 2.215 | 0.188 | 11 | 5.321 | 0.502 | 11 | 6.964 | 0.332 | 12 |
| Day 16 | 0.281 | 0.262 | 11 | 2.576 | 0.191 | 11 | 5.564 | 0.504 | 11 | 7.357 | 0.326 | 12 |
| Day 17 | 0.050 | 0.265 | 11 | 2.395 | 0.178 | 11 | 5.535 | 0.492 | 11 | 7.386 | 0.302 | 12 |
| Day 20 | 0.195 | 0.345 | 11 | 2.626 | 0.207 | 11 | 6.429 | 0.449 | 11 | 8.196 | 0.378 | 12 |
| Day 21 | −0.347 | 0.285 | 11 | 2.172 | 0.193 | 11 | 6.024 | 0.502 | 11 | 7.624 | 0.363 | 12 |

TABLE 2C

Change in Body Composition from Baseline

| | Lean Mass Change (g) | | | Fat Mass Change (g) | | |
|---|---|---|---|---|---|---|
| | Mean | SEM | N | Mean | SEM | N |
| Control mAb | −0.467 | 0.210 | 11 | 0.286 | 0.118 | 11 |
| αGDF8 + αActA | 3.432 | 0.117 | 11 | −1.118 | 0.205 | 11 |
| LEPR antagonist mAb | 0.532 | 0.195 | 11 | 4.897 | 0.551 | 11 |
| LEPR antagonist mAb + αGDF8 + αActA | 3.992 | 0.288 | 12 | 3.400 | 0.298 | 12 |

TABLE 3A

Twitch Force, Peak Tetanic Force, and Specific Force (mN)

| | Control mAb | | | αGDF8 + αActA | | | LEPR antagonist mAb | | | LEPR antagonist mAb + αGDF8 + αActA | | |
|---|---|---|---|---|---|---|---|---|---|---|---|---|
| | Mean | SEM | N | Mean | SEM | N | Mean | SEM | N | Mean | SEM | N |
| Twitch Force (mN) | 352.300 | 16.990 | 6 | 472.300 | 18.730 | 5 | 352.000 | 24.000 | 4 | 481.700 | 27.340 | 7 |
| Peak Tetanic Force (mN) | 997.300 | 47.510 | 6 | 1415.000 | 49.740 | 5 | 842.000 | 80.380 | 4 | 1282.000 | 59.600 | 7 |
| Specific Force (mN) | 19.770 | 0.317 | 6 | 20.500 | 0.150 | 5 | 15.770 | 1.661 | 4 | 19.200 | 1.092 | 7 |

TABLE 3B

Isometric Tetanic Force (mN)

| | Control mAb | | | αGDF8 + αActA | | | LEPR antagonist mAb | | | LEPR antagonist mAb + αGDF8 + αActA | | |
|---|---|---|---|---|---|---|---|---|---|---|---|---|
| | Mean | SEM | N | Mean | SEM | N | Mean | SEM | N | Mean | SEM | N |
| 40 Hz | 564.712 | 48.438 | 6 | 771.410 | 37.949 | 5 | 582.244 | 28.587 | 4 | 788.626 | 58.501 | 7 |
| 60 Hz | 882.634 | 43.772 | 6 | 1183.435 | 47.472 | 5 | 791.627 | 50.899 | 4 | 1142.551 | 51.231 | 7 |
| 80 Hz | 976.495 | 47.602 | 6 | 1357.974 | 50.474 | 5 | 833.329 | 73.525 | 4 | 1249.999 | 60.957 | 7 |
| 100 Hz | 995.798 | 47.934 | 6 | 1414.735 | 49.740 | 5 | 813.684 | 88.515 | 4 | 1282.284 | 59.602 | 7 |

TABLE 3B-continued

| Isometric Tetanic Force (mN) | Control mAb | | | αGDF8 + αActA | | | LEPR antagonist mAb | | | LEPR antagonist mAb + αGDF8 + αActA | | |
|---|---|---|---|---|---|---|---|---|---|---|---|---|
| | Mean | SEM | N | Mean | SEM | N | Mean | SEM | N | Mean | SEM | N |
| 125 Hz | 979.120 | 47.815 | 6 | 1393.443 | 45.717 | 5 | 778.318 | 97.194 | 4 | 1244.875 | 57.801 | 7 |
| 150 Hz | 926.029 | 45.454 | 6 | 1325.240 | 50.839 | 5 | 732.848 | 91.838 | 4 | 1174.292 | 59.950 | 7 |
| 200 Hz | 847.518 | 42.148 | 6 | 1199.041 | 50.727 | 5 | 678.718 | 84.987 | 4 | 1070.346 | 60.009 | 7 |

TABLE 4A

| Fat Mass (g) | Control mAb | | | aGDF8 + αActA | | | LEPR antagonist mAb | | | LEPR antagonist mAb + αGDF8 + αActA | | |
|---|---|---|---|---|---|---|---|---|---|---|---|---|
| | Mean | SEM | N | Mean | SEM | N | Mean | SEM | N | Mean | SEM | N |
| Week 0 | 5.227 | 0.477 | 11 | 5.779 | 0.558 | 11 | 5.626 | 0.461 | 11 | 5.425 | 0.415 | 12 |
| Week 1 | 5.149 | 0.503 | 11 | 5.199 | 0.528 | 11 | 7.476 | 0.626 | 11 | 6.583 | 0.510 | 12 |
| Week 2 | 5.395 | 0.544 | 11 | 4.858 | 0.484 | 11 | 9.389 | 0.759 | 11 | 8.008 | 0.401 | 12 |
| Week 3 | 5.514 | 0.491 | 11 | 4.661 | 0.458 | 11 | 10.524 | 0.800 | 11 | 8.825 | 0.411 | 12 |

TABLE 4B

| Fat Mass (g Difference from Baseline) | Control mAb | | | aGDF8 + αActA | | | LEPR antagonist mAb | | | LEPR antagonist mAb + αGDF8 + αActA | | |
|---|---|---|---|---|---|---|---|---|---|---|---|---|
| | Mean | SEM | N | Mean | SEM | N | Mean | SEM | N | Mean | SEM | N |
| Week 0 | 0.000 | 0.000 | 11 | 0.000 | 0.000 | 11 | 0.000 | 0.000 | 11 | 0.000 | 0.000 | 12 |
| Week 1 | −0.078 | 0.096 | 11 | −0.580 | 0.086 | 11 | 1.850 | 0.234 | 11 | 1.158 | 0.257 | 12 |
| Week 2 | 0.167 | 0.123 | 11 | −0.921 | 0.160 | 11 | 3.763 | 0.410 | 11 | 2.583 | 0.304 | 12 |
| Week 3 | 0.286 | 0.118 | 11 | −1.118 | 0.205 | 11 | 4.897 | 0.551 | 11 | 3.400 | 0.298 | 12 |

TABLE 4C

| Lean Mass (g) | Control mAb | | | aGDF8 + αActA | | | LEPR antagonist mAb | | | LEPR antagonist mAb + αGDF8 + αActA | | |
|---|---|---|---|---|---|---|---|---|---|---|---|---|
| | Mean | SEM | N | Mean | SEM | N | Mean | SEM | N | Mean | SEM | N |
| Week 0 | 23.507 | 0.476 | 11 | 23.075 | 0.493 | 11 | 23.213 | 0.637 | 11 | 23.420 | 0.486 | 12 |
| Week 1 | 23.390 | 0.517 | 11 | 24.701 | 0.554 | 11 | 23.805 | 0.613 | 11 | 25.693 | 0.492 | 12 |
| Week 2 | 23.307 | 0.547 | 11 | 25.968 | 0.590 | 11 | 23.681 | 0.547 | 11 | 26.865 | 0.565 | 12 |
| Week 3 | 23.040 | 0.495 | 11 | 26.507 | 0.507 | 11 | 23.745 | 0.539 | 11 | 27.412 | 0.545 | 12 |

TABLE 4D

| Lean Mass (g Difference from Baseline) | Control mAb | | | aGDF8 + αActA | | | LEPR antagonist mAb | | | LEPR antagonist mAb + αGDF8 + αActA | | |
|---|---|---|---|---|---|---|---|---|---|---|---|---|
| | Mean | SEM | N | Mean | SEM | N | Mean | SEM | N | Mean | SEM | N |
| Week 0 | 0.000 | 0.000 | 11 | 0.000 | 0.000 | 11 | 0.000 | 0.000 | 11 | 0.000 | 0.000 | 12 |
| Week 1 | −0.117 | 0.123 | 11 | 1.625 | 0.129 | 11 | 0.592 | 0.110 | 11 | 2.273 | 0.116 | 12 |
| Week 2 | −0.200 | 0.148 | 11 | 2.893 | 0.195 | 11 | 0.468 | 0.140 | 11 | 3.445 | 0.186 | 12 |
| Week 3 | −0.467 | 0.210 | 11 | 3.432 | 0.117 | 11 | 0.532 | 0.195 | 11 | 3.992 | 0.288 | 12 |

TABLE 5

| Organ Mass, Muscle Mass, Fat Mass (mg) | | | | | | | | | | | | |
|---|---|---|---|---|---|---|---|---|---|---|---|---|
| | Control mAb | | | aGDF8 + αActA | | | LEPR antagonist mAb | | | LEPR antagonist mAb + αGDF8 + αActA | | |
| | Mean | SEM | N | Mean | SEM | N | Mean | SEM | N | Mean | SEM | N |
| Heart | 144.70 | 4.86 | 11 | 149.50 | 2.67 | 11 | 151.90 | 3.13 | 11 | 152.10 | 2.99 | 12 |
| Liver | 1449.00 | 71.30 | 10 | 1432.00 | 55.00 | 11 | 1695.00 | 105.20 | 11 | 1637.00 | 45.11 | 12 |
| Quad | 203.10 | 4.45 | 11 | 270.80 | 7.69 | 11 | 210.10 | 6.95 | 11 | 263.10 | 8.05 | 12 |
| TA Muscle | 51.07 | 1.59 | 11 | 65.33 | 2.01 | 11 | 51.35 | 1.80 | 11 | 67.41 | 1.89 | 12 |
| GA Muscle | 161.90 | 4.02 | 11 | 212.00 | 5.29 | 11 | 166.10 | 5.90 | 11 | 213.10 | 4.87 | 12 |
| Inguinal WAT | 510.50 | 60.33 | 11 | 430.30 | 56.39 | 11 | 992.20 | 84.22 | 11 | 893.60 | 67.38 | 12 |
| Gonadal WAT | 771.30 | 84.83 | 11 | 652.20 | 67.24 | 11 | 1592.00 | 80.00 | 11 | 1414.00 | 73.00 | 12 |
| BAT | 103.50 | 10.32 | 11 | 97.96 | 6.19 | 11 | 186.10 | 15.47 | 11 | 146.00 | 7.19 | 12 |

TA: tibialis anteror; GA: gastrocnemius; WAT: white adipose tissue; BAT: brown adipose tissue.

TABLE 6

| Organ Mass, Muscle Mass, Fat Mass (% of Starting Body Weight) | | | | | | | | | | | | |
|---|---|---|---|---|---|---|---|---|---|---|---|---|
| | Control mAb | | | aGDF8 + αActA | | | LEPR antagonist mAb | | | LEPR antagonist mAb + αGDF8 + αActA | | |
| | Mean | SEM | N | Mean | SEM | N | Mean | SEM | N | Mean | SEM | N |
| Heart | 0.457 | 0.013 | 11 | 0.473 | 0.005 | 11 | 0.480 | 0.011 | 11 | 0.480 | 0.010 | 12 |
| Liver | 4.576 | 0.140 | 10 | 4.527 | 0.158 | 11 | 5.310 | 0.227 | 11 | 5.170 | 0.159 | 12 |
| Quad | 0.641 | 0.010 | 11 | 0.857 | 0.025 | 11 | 0.663 | 0.019 | 11 | 0.830 | 0.026 | 12 |
| TA Muscle | 0.161 | 0.005 | 11 | 0.206 | 0.005 | 11 | 0.162 | 0.005 | 11 | 0.212 | 0.005 | 12 |
| GA Muscle | 0.512 | 0.013 | 11 | 0.670 | 0.014 | 11 | 0.523 | 0.011 | 11 | 0.672 | 0.015 | 12 |
| Inguinal WAT | 1.590 | 0.169 | 11 | 1.341 | 0.155 | 11 | 3.130 | 0.253 | 11 | 2.826 | 0.224 | 12 |
| Gonadal WAT | 2.392 | 0.231 | 11 | 2.029 | 0.172 | 11 | 5.015 | 0.238 | 11 | 4.441 | 0.201 | 12 |
| BAT | 0.322 | 0.027 | 11 | 0.308 | 0.017 | 11 | 0.583 | 0.045 | 11 | 0.460 | 0.022 | 12 |

TABLE 7

| Organ Mass, Muscle Mass, Fat Mass (% Change from Control) | | | | | | | | | | | | |
|---|---|---|---|---|---|---|---|---|---|---|---|---|
| | Control mAb | | | aGDF8 + αActA | | | LEPR antagonist mAb | | | LEPR antagonist mAb + αGDF8 + αActA | | |
| | Mean | SEM | N | Mean | SEM | N | Mean | SEM | N | Mean | SEM | N |
| Heart | −3.182E−08 | 2.747 | 11 | 3.480 | 1.151 | 11 | 5.058 | 2.353 | 11 | 5.065 | 2.275 | 12 |
| Liver | −0.00000005 | 3.050 | 10 | −1.055 | 3.460 | 11 | 16.050 | 4.962 | 11 | 12.990 | 3.476 | 12 |
| Quad | −4.545E−09 | 1.520 | 11 | 33.670 | 3.827 | 11 | 3.426 | 2.984 | 11 | 29.490 | 4.132 | 12 |
| TA Muscle | −5.818E−08 | 2.851 | 11 | 27.880 | 2.986 | 11 | 0.460 | 3.097 | 11 | 31.610 | 3.035 | 12 |
| GA Muscle | −4.182E−08 | 2.595 | 11 | 30.940 | 2.757 | 11 | 2.073 | 2.241 | 11 | 31.250 | 2.866 | 12 |
| Inguinal WAT | 6.364E−08 | 10.660 | 11 | −15.660 | 9.761 | 11 | 96.900 | 15.940 | 11 | 77.740 | 14.100 | 12 |
| Gonadal WAT | 2.273E−08 | 9.652 | 11 | −15.170 | 7.197 | 11 | 109.600 | 9.929 | 11 | 85.620 | 8.399 | 12 |
| BAT | 2.455E−08 | 8.318 | 11 | −4.226 | 5.146 | 11 | 81.030 | 13.930 | 11 | 42.800 | 6.818 | 12 |

Example 3: Combination Treatment of Anti-GDF8 mAb (REGN1033), Anti-Activin A mAb (REGN2477), and LEPR Antagonist mAb (H4H18457P2) in 12 to 14 Week Old Male Mice (+Additional Treatment Groups)

The effects of the specific antagonist anti-LEPR antibody, H4H18457P2, in combination with the anti-MSTN (also referred to as anti-GDF8) and anti-INHBA (also referred to as anti-Activin A) blocking antibodies, H4H1657N2 (REGN1033) and H4H10446P2 (REGN2477), respectively, of the invention, on food intake, body weight, body composition, individual tissue weights, and ex vivo muscle force generation were determined in singly-housed genetically engineered 12 to 14 week old male LEPR$^{HuHu}$ mice, that express a leptin receptor which is composed of the human LEPR ectodomain sequence in place of the murine LEPR ectodomain sequence.

Baseline daily food intake was measured between days −8 and 0. On day −1, baseline whole body lean and fat mass was quantified by NMR. On day 0, mice were stratified to six groups of 7 to 8 mice based on body composition from day −1 and body weight from day 0. Starting on day 0, each group received the respective antibody treatment dose via subcutaneous injection. REGN1033, REGN2477, and the respective IgG4P mAbs are dosed twice a week at 10 mg/kg. H4H18457P2 and its respective IgG4P mAb are dosed once a week at 30 mg/kg. The isotype control (IgG4P) antibody (REGN1945) does not bind any known mouse protein.

Treatment Groups a) IgG4P Control (10 mg/kg+10 mg/kg, 2×/week; 30 mg/kg, 1×/week), N=7 b) REGN1033 (10 mg/kg, 2×/week), N=7 c) REGN1033+REGN2477 (10 mg/kg+10 mg/kg, 2×/week), N=7 d) H4H18457P2 (30 mg/kg, 1×/week), N=7 e) REGN1033+H4H18457P2 (10 mg/kg, 2×/week; 30 mg/kg, 1×/week), N=8 f) REGN1033+REGN2477+H4H18457P2 (10 mg/kg+10 mg/kg, 2×/week; 30 mg/kg, 1×/week), N=8

Food intake (Table 8B) and body weight (Table 8A) were measured for the duration of the study for each animal. Body composition was quantified on days 6, 13 and 20 (Tables 8C and 8D). On day 21 or 22, animals were euthanized for additional analyses including skeletal muscle fiber number and cross-sectional fiber area (Tables 9-11).

Compared to isotype control antibody, the LEPR antagonist, H4H18457P2, significantly increased body weight and cumulative food intake when administered alone or in combination with REGN1033 or REGN1033 and REGN2477. Mice treated with H4H18457P2 showed significant increases in body weight and cumulative food intake (Tables 8A and 8B) starting at days 13 and 8, respectively, and at subsequent time points, when compared to mice administered isotype control antibody. Body weight and cumulative food intake was significantly elevated with H4H18457P2 and REGN1033 treatment starting at day 7 and at subsequent time points, as compared to isotype control antibody administrations. Mice treated with H4H18457P2, REGN1033 and REGN2477 also showed increased body weight and food intake from days 8 and at 7, respectively, to the end of the study when compared to mice administered isotype control antibody. Mice treated with REGN1033 or REGN1033 and REGN2477 did not exhibit significant changes in body weight or cumulative food intake relative to mice administered control antibody.

Mice treated with H4H18457P2 alone or in combination with REGN1033 or REGN1033 and REGN2477, showed increases in fat mass from baseline at all measured time-points (days 6, 13 and 20) when compared to mice administered isotype control antibody (Table 8D). At days 13 and 20, mice treated with H4H18457P2, REGN1033 and REGN2477 showed less fat mass gain from baseline than mice treated with H4H18457P2 alone or in combination with REGN1033 (Table 8D). Mice treated with H4H18457P2, REGN1033 and REGN2477 also showed significant increase in lean mass gain from baseline at days 13 and 20 when compared to mice administered isotype control antibody (Table 8C).

Histological analyses revealed no significant effects of any treatment group compared to isotype control antibody administration on the number of muscle fibers in the tibialis anterior or gastrocnemius (Tables 9 and 10). Compared to isotype control antibody delivery, mice treated with REGN1033 in combination with REGN2477 or H4H18457P2 showed increased muscle fiber numbers in the soleus muscle (Table 11). In all three muscles (tibialis anterior, gastrocnemius and soleus) examined, H4H18457P2 treatment did not affect muscle fiber area when compared to isotype control antibody administration (Tables 9, 10 and 11). Mice treated with either REGN1033, REGN1033 and REGN2477, REGN1033 and H4H18457P2, or REGN1033 and REGN2477 and H4H18457P2 showed increased muscle fiber area in the tibialis anterior and gastrocnemius (Tables 9 and 10) when compared to mice administered isotype control antibody. In soleus muscle, only mice treated with the triple combination of H4H18457P2, REGN1033 and REN2477 showed increased muscle fiber area relative to mice administered isotype control antibody (Table 11).

In summary, LEPR antagonist antibody treatment alone increases body weight, food intake and adiposity, and in combination with anti-ActA and/or anti-MSTN blocking antibodies induces additional increases in muscle fiber area or number, respectively.

TABLE 8A

| Body Weight (g) | | | | | | | | | | | | | | | | | | |
|---|---|---|---|---|---|---|---|---|---|---|---|---|---|---|---|---|---|---|
| | IgG4$^{P}$ | | | REGN1033 | | | REGN1033 + REGN2477 | | | H4H18457P2 | | | REGN1033 + H4H18457P2 | | | REGN1033 + REGN2477 + H4H18457P2 | | |
| | Mean | SEM | N | Mean | SEM | N | Mean | SEM | N | Mean | SEM | N | Mean | SEM | N | Mean | SEM | N |
| Day 0 | 27.267 | 1.145 | 7 | 27.263 | 1.156 | 7 | 27.357 | 1.020 | 7 | 27.650 | 0.803 | 7 | 27.185 | 0.908 | 8 | 27.148 | 1.065 | 8 |
| Day 2 | 27.580 | 1.086 | 7 | 27.927 | 1.161 | 7 | 28.121 | 1.041 | 7 | 29.437 | 0.775 | 7 | 29.141 | 0.849 | 8 | 28.915 | 1.081 | 8 |
| Day 3 | 27.517 | 1.098 | 7 | 28.093 | 1.193 | 7 | 28.094 | 1.023 | 7 | 29.899 | 0.806 | 7 | 29.966 | 0.970 | 8 | 29.650 | 1.081 | 8 |
| Day 6 | 27.464 | 1.090 | 7 | 28.690 | 1.232 | 7 | 28.907 | 1.014 | 7 | 31.124 | 0.934 | 7 | 31.813 | 0.995 | 8 | 31.539 | 1.100 | 8 |
| Day 7 | 27.423 | 1.077 | 7 | 28.611 | 1.215 | 7 | 28.854 | 0.984 | 7 | 31.044 | 0.949 | 7 | 32.003 | 1.025 | 8 | 31.774 | 1.111 | 8 |
| Day 8 | 27.696 | 1.176 | 7 | 28.961 | 1.133 | 7 | 29.186 | 1.076 | 7 | 31.704 | 0.896 | 7 | 32.719 | 1.009 | 8 | 32.340 | 1.136 | 8 |
| Day 9 | 27.723 | 1.152 | 7 | 29.446 | 1.321 | 7 | 29.391 | 1.004 | 7 | 31.963 | 1.015 | 7 | 33.186 | 0.925 | 8 | 32.908 | 1.133 | 8 |
| Day 10 | 27.759 | 1.156 | 7 | 29.169 | 1.144 | 7 | 29.373 | 1.008 | 7 | 32.306 | 0.961 | 7 | 33.569 | 0.966 | 8 | 33.299 | 1.211 | 8 |
| Day 13 | 27.867 | 1.140 | 7 | 29.591 | 1.185 | 7 | 29.831 | 0.933 | 7 | 33.291 | 0.880 | 7 | 34.555 | 1.109 | 8 | 34.550 | 1.308 | 8 |

TABLE 8A-continued

| Body Weight (g) | IgG4$^P$ | | | REGN1033 | | | REGN1033 + REGN2477 | | | H4H18457P2 | | | REGN1033 + H4H18457P2 | | | REGN1033 + REGN2477 + H4H18457P2 | | |
|---|---|---|---|---|---|---|---|---|---|---|---|---|---|---|---|---|---|---|
| | Mean | SEM | N | Mean | SEM | N | Mean | SEM | N | Mean | SEM | N | Mean | SEM | N | Mean | SEM | N |
| Day 14 | 27.883 | 1.162 | 7 | 29.343 | 1.195 | 7 | 29.770 | 0.939 | 7 | 33.059 | 1.026 | 7 | 34.668 | 1.157 | 8 | 34.658 | 1.248 | 8 |
| Day 16 | 28.104 | 1.130 | 7 | 30.213 | 1.186 | 7 | 30.509 | 0.964 | 7 | 33.691 | 1.023 | 7 | 35.610 | 1.142 | 8 | 36.058 | 1.360 | 8 |
| Day 17 | 28.217 | 1.074 | 7 | 29.861 | 1.191 | 7 | 30.259 | 0.978 | 7 | 33.771 | 1.052 | 7 | 35.796 | 1.143 | 8 | 36.114 | 1.347 | 8 |
| Day 20 | 28.304 | 1.167 | 7 | 30.234 | 1.257 | 7 | 30.530 | 0.793 | 7 | 34.724 | 1.118 | 7 | 36.529 | 1.224 | 8 | 36.976 | 1.351 | 8 |
| Day 21 | 28.229 | 1.197 | 7 | 30.264 | 1.242 | 7 | 30.811 | 0.978 | 7 | 34.516 | 1.115 | 7 | 36.604 | 1.258 | 8 | 36.830 | 1.368 | 8 |

TABLE 8B

| Cumulative Food Intake | IgG4$^P$ | | | REGN1033 | | | REGN1033 + REGN2477 | | | H4H18457P2 | | | REGN1033 + H4H18457P2 | | | REGN1033 + REGN2477 + H4H18457P2 | | |
|---|---|---|---|---|---|---|---|---|---|---|---|---|---|---|---|---|---|---|
| | Mean | SEM | N | Mean | SEM | N | Mean | SEM | N | Mean | SEM | N | Mean | SEM | N | Mean | SEM | N |
| Day 0 | 0.000 | 0.000 | 7 | 0.000 | 0.000 | 7 | 0.000 | 0.000 | 7 | 0.000 | 0.000 | 6 | 0.000 | 0.000 | 7 | 0.000 | 0.000 | 8 |
| Day 2 | 9.050 | 0.379 | 7 | 8.993 | 0.601 | 7 | 9.070 | 0.284 | 7 | 10.548 | 0.407 | 6 | 10.527 | 0.400 | 7 | 10.433 | 0.298 | 8 |
| Day 3 | 13.421 | 0.639 | 7 | 13.491 | 0.753 | 7 | 13.533 | 0.434 | 7 | 16.620 | 0.637 | 6 | 16.636 | 0.564 | 7 | 16.754 | 0.477 | 8 |
| Day 6 | 26.191 | 1.373 | 7 | 26.673 | 1.326 | 7 | 26.543 | 0.839 | 7 | 32.998 | 1.303 | 6 | 34.169 | 1.278 | 7 | 34.114 | 0.605 | 8 |
| Day 7 | 30.711 | 1.500 | 7 | 31.011 | 1.476 | 7 | 30.684 | 1.036 | 7 | 38.523 | 1.498 | 6 | 39.857 | 1.364 | 7 | 39.715 | 0.799 | 8 |
| Day 8 | 34.877 | 1.689 | 7 | 35.223 | 1.665 | 7 | 34.610 | 1.258 | 7 | 43.735 | 1.580 | 6 | 45.370 | 1.504 | 7 | 45.015 | 0.918 | 8 |
| Day 9 | 39.234 | 1.955 | 7 | 39.561 | 1.792 | 7 | 38.820 | 1.401 | 7 | 48.983 | 1.831 | 6 | 50.886 | 1.591 | 7 | 50.593 | 1.107 | 8 |
| Day 10 | 43.473 | 2.260 | 7 | 43.599 | 1.934 | 7 | 42.959 | 1.542 | 7 | 54.487 | 1.946 | 6 | 56.586 | 1.615 | 7 | 56.254 | 1.246 | 8 |
| Day 13 | 55.691 | 2.936 | 7 | 56.084 | 2.509 | 7 | 55.276 | 1.921 | 7 | 70.253 | 2.310 | 6 | 73.181 | 1.959 | 7 | 72.801 | 1.886 | 8 |
| Day 14 | 60.170 | 3.083 | 7 | 60.543 | 2.776 | 7 | 59.541 | 1.966 | 7 | 75.147 | 2.497 | 6 | 78.610 | 2.026 | 7 | 78.475 | 2.036 | 8 |
| Day 16 | 68.284 | 3.526 | 7 | 68.890 | 3.181 | 7 | 68.131 | 2.319 | 7 | 84.507 | 2.676 | 6 | 88.901 | 2.155 | 7 | 89.314 | 2.248 | 8 |
| Day 17 | 72.526 | 3.721 | 7 | 72.721 | 3.367 | 7 | 72.154 | 2.450 | 7 | 89.543 | 2.855 | 6 | 93.999 | 2.203 | 7 | 94.939 | 2.429 | 8 |
| Day 20 | 84.754 | 4.432 | 7 | 85.340 | 3.774 | 7 | 85.024 | 2.630 | 7 | 105.160 | 3.373 | 6 | 109.866 | 2.730 | 7 | 111.293 | 2.916 | 8 |
| Day 21 | 88.433 | 4.661 | 7 | 89.089 | 3.962 | 7 | 88.910 | 2.770 | 7 | 109.127 | 3.478 | 6 | 114.414 | 2.916 | 7 | 116.163 | 3.025 | 8 |

TABLE 8C

| Lean Mass (g Difference from Baseline) | IgG4$^P$ | | | REGN1033 | | | REGN1033 + REGN2477 | | | H4H18457P2 | | | REGN1033 + H4H18457P2 | | | REGN1033 + REGN2477 + H4H18457P2 | | |
|---|---|---|---|---|---|---|---|---|---|---|---|---|---|---|---|---|---|---|
| | Mean | SEM | N | Mean | SEM | N | Mean | SEM | N | Mean | SEM | N | Mean | SEM | N | Mean | SEM | N |
| Day −1 | 0.000 | 0.000 | 7 | 0.000 | 0.000 | 7 | 0.000 | 0.000 | 7 | 0.000 | 0.000 | 7 | 0.000 | 0.000 | 8 | 0.000 | 0.000 | 8 |
| Day 6 | −0.026 | 0.107 | 7 | 1.321 | 0.119 | 7 | 1.704 | 0.088 | 7 | 1.227 | 0.242 | 7 | 2.288 | 0.123 | 8 | 2.576 | 0.171 | 8 |

TABLE 8C-continued

Lean Mass (g Difference from Baseline)

| | IgG4$^{P}$ | | | REGN1033 | | | REGN1033 + REGN2477 | | | H4H18457P2 | | | REGN1033 + H4H18457P2 | | | REGN1033 + REGN2477 + H4H18457P2 | | |
|---|---|---|---|---|---|---|---|---|---|---|---|---|---|---|---|---|---|---|
| | Mean | SEM | N | Mean | SEM | N | Mean | SEM | N | Mean | SEM | N | Mean | SEM | N | Mean | SEM | N |
| Day 13 | −0.016 | 0.210 | 7 | 1.930 | 0.151 | 7 | 2.997 | 0.108 | 7 | 1.490 | 0.227 | 7 | 3.201 | 0.197 | 8 | 4.281 | 0.282 | 8 |
| Day 20 | 0.274 | 0.299 | 7 | 2.573 | 0.188 | 7 | 3.873 | 0.336 | 7 | 1.777 | 0.388 | 7 | 3.899 | 0.268 | 8 | 5.716 | 0.328 | 8 |

TABLE 8D

Fat Mass (g Difference from Baseline)

| | IgG4$^{P}$ | | | REGN1033 | | | REGN1033 + REGN2477 | | | H4H18457P2 | | | REGN1033 + H4H18457P2 | | | REGN1033 + REGN2477 + H4H18457P2 | | |
|---|---|---|---|---|---|---|---|---|---|---|---|---|---|---|---|---|---|---|
| | Mean | SEM | N | Mean | SEM | N | Mean | SEM | N | Mean | SEM | N | Mean | SEM | N | Mean | SEM | N |
| Day −1 | 0 | 0 | 7 | 0 | 0 | 7 | 0 | 0 | 7 | 0 | 0 | 7 | 0 | 0 | 8 | 0 | 0 | 8 |
| Day 6 | −0.027 | 0.084 | 7 | −0.009 | 0.087 | 7 | −0.099 | 0.091 | 7 | 1.909 | 0.170 | 7 | 2.028 | 0.128 | 8 | 1.496 | 0.197 | 8 |
| Day 13 | 0.250 | 0.128 | 7 | 0.273 | 0.120 | 7 | −0.340 | 0.133 | 7 | 3.580 | 0.295 | 7 | 3.800 | 0.222 | 8 | 2.600 | 0.270 | 8 |
| Day 20 | 0.500 | 0.207 | 7 | 0.220 | 0.166 | 7 | −0.319 | 0.180 | 7 | 4.834 | 0.469 | 7 | 5.158 | 0.304 | 8 | 3.614 | 0.485 | 8 |

TABLE 9

TA Muscle Fiber Area and Number

| | IgG4$^{P}$ (N = 7) | | | REGN1033 (N = 7) | | | REGN1033 + REGN2477 (N = 7) | | | H4H18457P2 (N = 7) | | | REGN1033 + H4H18457P2 (N = 8) | | | REGN1033 + REGN2477 + H4H18457P2 (N = 8) | | |
|---|---|---|---|---|---|---|---|---|---|---|---|---|---|---|---|---|---|---|
| | Mean | SEM | N | Mean | SEM | N | Mean | SEM | N | Mean | SEM | N | Mean | SEM | N | Mean | SEM | N |
| Muscle Size (um^2) | 2004 | 56.01 | 7 | 2535 | 73.66 | 7 | 2841 | 150.5 | 7 | 2316 | 82.99 | 7 | 2491 | 87.98 | 8 | 3011 | 147.6 | 8 |
| Fiber Number (Number of Fibers) | 1982 | 117.1 | 7 | 1826 | 94.79 | 7 | 1839 | 115.7 | 7 | 1862 | 124.4 | 7 | 2018 | 163.2 | 8 | 1670 | 106.7 | 8 |

TABLE 10

GA Muscle Fiber Area and Number

| | Igg4$^{P}$ (N = 7) | | | REGN1033 (N = 7) | | | REGN1033 + REGN2477 (N = 7) | | | H4H18457P2 (N = 7) | | | REGN1033 + H4H18457P2 (N = 8) | | | REGN1033 + REGN2477 + H4H18457P2 (N = 8) | | |
|---|---|---|---|---|---|---|---|---|---|---|---|---|---|---|---|---|---|---|
| | Mean | SEM | N | Mean | SEM | N | Mean | SEM | N | Mean | SEM | N | Mean | SEM | N | Mean | SEM | N |
| Muscle Size (um^2) | 1903 | 69.1 | 7 | 2444 | 127.2 | 7 | 2319 | 42.42 | 7 | 1902 | 85.57 | 7 | 2340 | 52.31 | 8 | 2562 | 106.1 | 8 |
| Fiber Number (Number Of Fibers) | 4992 | 510 | 7 | 3864 | 368.7 | 7 | 4615 | 336.5 | 7 | 4830 | 576.7 | 7 | 4189 | 328.5 | 8 | 3748 | 460.1 | 8 |

TABLE 11

Soleus Muscle Fiber Area and Number

| | IgG4P (N = 7) | | | REGN1033 (N = 7) | | | REGN1033 + REGN2477 (N = 7) | | | H4H18457P2 (N = 7) | | | REGN1033 + H4H18457P2 (N = 8) | | | REGN1033 + REGN2477 + H4H18457P2 (N = 8) | | |
|---|---|---|---|---|---|---|---|---|---|---|---|---|---|---|---|---|---|---|
| | Mean | SEM | N | Mean | SEM | N | Mean | SEM | N | Mean | SEM | N | Mean | SEM | N | Mean | SEM | N |
| Muscle Size (um^2) | 1253 | 64.74 | 7 | 1590 | 188.8 | 7 | 1377 | 43.75 | 7 | 1235 | 79.26 | 7 | 1455 | 52.5 | 8 | 1696 | 84.62 | 8 |
| Fiber Number (Number of Fibers) | 539.4 | 71.96 | 7 | 650.3 | 87.98 | 7 | 797.3 | 34.8 | 7 | 729.9 | 41.15 | 7 | 811.4 | 24.63 | 8 | 726.4 | 54.47 | 8 |

Example 4: Combination Treatment of Anti-GDF8 mAb (REGN1033), Anti-Activin A mAb (REGN2477), and LEPR Antagonist mAb (H4H18457P2) in Male Mice The effects of the specific antagonist anti-LEPR antibody, H4H18457P2, in combination with the anti-MSTN (also referred to as GDF8) and anti-INHBA (also referred to as Activin A) blocking antibodies, H4H1657N2 (REGN1033) and H4H10446P2 (REGN2477), respectively, on food intake, body weight, body composition, individual tissue weights, and ex vivo muscle force generation were determined in singly-housed genetically engineered 12 to 14 week old male $LEPR^{Hu/Hu}$ mice, that express a leptin receptor which is composed of the human LEPR ectodomain sequence in place of the murine LEPR ectodomain sequence.

Baseline daily food intake was measured between days −8 and 0. On day −1, baseline whole body lean and fat mass was quantified by NMR. On day 0, mice were stratified to six groups of 7 to 8 mice based on body composition from day −1 and body weight from day 0. Starting on day 0, each group received the respective antibody treatment dose via subcutaneous injection. REGN1033, REGN2477, and the respective IgG4P mAbs were dosed twice a week at 10 mg/kg. H4H18457P2 and its respective IgG4P mAb were dosed once a week at 30 mg/kg. The isotype control (IgG4P) antibody does not bind any known mouse protein.

Treatment Groups a) IgG4P Control (10 mg/kg+10 mg/kg, 2×/week; 30 mg/kg, 1×/week), N=7
b) REGN1033 (10 mg/kg, 2×/week), N=7
c) REGN1033+REGN2477 (10 mg/kg+10 mg/kg, 2×/week), N=7
d) H4H18457P2 (30 mg/kg, 1×/week), N=7
e) REGN1033+H4H18457P2 (10 mg/kg, 2×/week; 30 mg/kg, 1×/week), N=8
f) REGN1033+REGN2477+H4H18457P2 (10 mg/kg+10 mg/kg, 2×/week; 30 mg/kg, 1×/week), N=8

Food intake and body weight were measured for the duration of the study for each animal. Body composition was quantified on days 6, 13 and 20. On day 21 or 22, animals were euthanized, individual organ and skeletal muscle tissues were weighed and collected for additional analyses including liver triglyceride quantification and skeletal muscle fiber number and cross-sectional fiber area.

Quantification of liver triglyceride content revealed that mice treated with H4H18457P2 alone or in combination with REGN1033, showed increased liver triglyceride content when compared to mice administered isotype control antibody (Table 12). In contrast, liver triglyceride content was not increased in mice treated with H4H18457P2 in combination with REGN1033 and REGN2477 when compared to mice administered isotype control antibody (Table 12). Mice treated with H4H18457P2 in combination with REGN1033 and REGN2477 exhibited decreased liver triglyceride content when compared with mice treated with H4H18457P2 in combination with REGN1033 (Table 12). In summary, LEPR antagonist antibody treatment increased liver triglyceride content that is mitigated in a combination treatment with LEPR antagonist, anti-ActA and anti-MSTN blocking antibodies.

TABLE 12

Liver Triglycerides

| | IgG4P | | | REGN1033 | | | REGN1033 + REGN2477 | | | H4H18457P2 | | | REGN1033 + H4H18457P2 | | | REGN1033 + REGN2477 + H4H18457P2 | | |
|---|---|---|---|---|---|---|---|---|---|---|---|---|---|---|---|---|---|---|
| | Mean | SEM | N | Mean | SEM | N | Mean | SEM | N | Mean | SEM | N | Mean | SEM | N | Mean | SEM | N |
| Liver Triglyceride (mg/g wet weight) | 8.927 | 6.163 | 7 | 9.687 | 6.552 | 5** | 8.093 | 5.782 | 7 | 19.09 | 8.495 | 6* | 19.18 | 13.53 | 8 | 12.53 | 5.846 | 8 |

**Data for 2 out of 7 mice not included in values shown

*Data for 1 out of 7 mice not included in values shown

We claim:

1. A method for increasing lean mass and decreasing the proportion of fat mass to lean mass, in a subject in need thereof, comprising administering a therapeutically effective amount of a combination comprising a leptin receptor antagonist in association with a GDF8 antagonist in association with an Activin A antagonist to the subject, wherein:

the leptin receptor (LEPR) antagonist is an antibody or antigen-binding fragment thereof that binds specifically to LEPR comprising a heavy chain variable region that comprises three heavy chain complementary determining regions (CDR-H1, CDR-H2, CDR-H3) of a heavy chain variable region comprising the amino acid sequence as set forth in SEQ ID NO:1, and a light chain variable region that comprises three light chain complementary determining regions (CDR-L1, CDR-L2, CDR-L3) of a light chain variable region comprising the amino acid sequence as set forth in SEQ ID NO:2, the growth and differentiation factor-8 (GDF8) antagonist is an antibody or antigen-binding fragment thereof that binds specifically to GDF8 comprising a heavy chain variable region that comprises three heavy chain complementarity determining regions (CDR-H1, CDR-H2, CDR-H3) of a heavy chain variable region comprising the amino acid sequence as set forth in SEQ ID NO: 9, and a light chain variable region that comprises three light chain complementary determining regions (CDR-L1, CDR-L2, CDR-L3) of a light chain variable region comprising the amino acid sequence as set forth in SEQ ID NO: 10; and the Activin A antagonist is an antibody or antigen-binding fragment thereof that binds specifically to Activin A comprising a heavy chain variable region that comprises three heavy chain complementarity determining regions (CDR-H1, CDR-H2, CDR-H3) of a heavy chain variable region comprising the amino acid sequence as set forth in SEQ ID NO:17, and a light chain variable region that comprises three light chain complementary determining regions (CDR-L1, CDR-L2, CDR-L3) of a light chain variable region comprising the amino acid sequence as set forth in SEQ ID NO:18;

wherein said increase in lean mass and said decrease in the proportion of fat mass to lean mass in said subject is compared to lean mass and proportion of fat mass to lean mass in said subject prior to said administering.

2. The method of claim 1, wherein:

the leptin receptor (LEPR) antibody or antigen-binding fragment thereof comprises a CDR-H1 amino acid sequence as set forth in SEQ ID NO: 6, a CDR-H2 amino acid sequence as set forth in SEQ ID NO: 7, a CDR-H3 amino acid sequence as set forth in SEQ ID NO: 8, a CDR-L1 amino acid sequence as set forth in SEQ ID NO: 3, a CDR-L2 amino acid sequence as set forth in SEQ ID NO: 4, and a CDR-L3 amino acid sequence as set forth in SEQ ID NO: 5;

the growth and differentiation factor-8 (GDF8) antibody or antigen-binding fragment thereof comprises a CDR-H1 amino acid sequence as set forth in SEQ ID NO: 14, a CDR-H2 amino acid sequence as set forth in SEQ ID NO: 15, a CDR-H3 amino acid sequence as set forth in SEQ ID NO: 16, a CDR-L1 amino acid sequence as set forth in SEQ ID NO: 11, a CDR-L2 amino acid sequence as set forth in SEQ ID NO: 12, a CDR-L3 amino acid sequence as set forth in SEQ ID NO: 13; and the Activin A antibody or antigen-binding fragment thereof comprises a CDR-H1 amino acid sequence as set forth in SEQ ID NO: 22, a CDR-H2 amino acid sequence as set forth in SEQ ID NO: 23, a CDR-H3 amino acid sequence as set forth in SEQ ID NO: 24, a CDR-L1 amino acid sequence as set forth in SEQ ID NO: 19, a CDR-L2 amino acid sequence as set forth in SEQ ID NO: 20, a CDR-L3 amino acid sequence as set forth in SEQ ID NO: 21.

3. The method of claim 1, wherein:

the leptin receptor (LEPR) antibody or antigen-binding fragment thereof that binds specifically to LEPR comprises a heavy chain variable region amino acid sequence as set forth in SEQ ID NO: 1 and a light chain variable region amino acid sequence as set forth in SEQ ID NO: 2;

the growth and differentiation factor-8 (GDF8) antibody or antigen-binding fragment thereof that binds specifically to GDF8 comprises a heavy chain variable region amino acid sequence as set forth in SEQ ID NO: 9 and a light chain variable region amino acid sequence as set forth in SEQ ID NO: 10; and the Activin A antagonist antibody or antigen-binding fragment thereof that binds specifically to Activin A comprises a heavy chain variable region amino acid sequence as set forth in SEQ ID NO: 17 and a light chain variable region amino acid sequence as set forth in SEQ ID NO: 18.

4. The method of claim 1, wherein the subject suffers from one or more selected from malnutrition, failure to thrive, insufficient food intake, an eating disorder, cachexia, muscle atrophy or wasting and muscle injury;

and/or, is undergoing stroke rehabilitation.

* * * * *